United States Patent
Maile et al.

(10) Patent No.: US 10,918,875 B2
(45) Date of Patent: Feb. 16, 2021

(54) IMPLANTABLE MEDICAL DEVICE WITH A FLUX CONCENTRATOR AND A RECEIVING COIL DISPOSED ABOUT THE FLUX CONCENTRATOR

(71) Applicant: CARDIAC PACEMAKERS, INC., St. Paul, MN (US)

(72) Inventors: Keith R. Maile, New Brighton, MN (US); William J. Linder, Golden Valley, MN (US); Moira B. Sweeney, St. Paul, MN (US); Ryan Peter Solstad, Minneapolis, MN (US)

(73) Assignee: CARDIAC PACEMAKERS, INC., St. Paul, MN (US)

(*) Notice: Subject to any disclaimer, the term of this patent is extended or adjusted under 35 U.S.C. 154(b) by 173 days.

(21) Appl. No.: 16/104,219

(22) Filed: Aug. 17, 2018

(65) Prior Publication Data
US 2019/0105500 A1   Apr. 11, 2019

Related U.S. Application Data

(60) Provisional application No. 62/547,423, filed on Aug. 18, 2017.

(51) Int. Cl.
*A61N 1/378* (2006.01)
*A61N 1/375* (2006.01)
(Continued)

(52) U.S. Cl.
CPC ......... *A61N 1/3787* (2013.01); *A61N 1/0587* (2013.01); *A61N 1/3756* (2013.01); *A61N 1/3956* (2013.01); *A61N 1/3975* (2013.01); *H02J 7/025* (2013.01); *A61N 1/362* (2013.01); *A61N 1/37205* (2013.01); *H02J 50/12* (2016.02)

(58) Field of Classification Search
CPC ............ A61N 1/37223; A61N 1/37229; A61N 1/3787
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2009231721 B2 | 10/2009 |
| AU | 2008279789 B2 | 10/2011 |

(Continued)

OTHER PUBLICATIONS

US 8,886,318 B2, 11/2014, Jacobson et al. (withdrawn)
(Continued)

*Primary Examiner* — Allen Porter
(74) *Attorney, Agent, or Firm* — Seager, Tufte & Wickhem LLP.

(57) ABSTRACT

An implantable medical device (IMD) with a receiving coil for wireless power transfer. The receiving coil may be disposed about a flux concentrator located in a housing of the IMD. The flux concentrator may concentrate non-radiative near-field energy through the receiving coil. In some cases, the near-field energy may be captured and converted into electrical energy that may be used to recharge a rechargeable power source of the IMD.

19 Claims, 40 Drawing Sheets

(51) Int. Cl.
*A61N 1/05* (2006.01)
*A61N 1/39* (2006.01)
*H02J 7/02* (2016.01)
*A61N 1/362* (2006.01)
*A61N 1/372* (2006.01)
*H02J 50/12* (2016.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,254,997 A | 10/1993 | Cohn |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,871,625 A | 2/1999 | Leddy et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,928,804 A | 7/1999 | Leddy et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,981,095 A | 11/1999 | Leddy et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |

(56) References Cited

U.S. PATENT DOCUMENTS

| | | |
|---|---|---|
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,207,313 B1 | 3/2001 | Leddy et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,322,676 B1 | 11/2001 | Leddy et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,355,166 B1 | 3/2002 | Amarasinghe et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,479,176 B2 | 11/2002 | Leddy et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,766,200 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,890,670 B2 | 5/2005 | Leddy et al. |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |

(56) References Cited

U.S. PATENT DOCUMENTS

| | | |
|---|---|---|
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,225,032 B2 | 5/2007 | Schmeling et al. |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,239,921 B2 | 7/2007 | Canfield et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,466 B2 | 5/2008 | He et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |

(56) References Cited

U.S. PATENT DOCUMENTS

| | | |
|---|---|---|
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,140,168 B2 | 3/2012 | Olson et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Mates |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,322 B2 | 10/2013 | Olson et al. |
| 8,554,333 B2 | 10/2013 | Wu et al. |
| 8,565,882 B2 | 10/2013 | Mates |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,630,717 B2 | 1/2014 | Olson et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |

(56) References Cited

U.S. PATENT DOCUMENTS

| | | |
|---|---|---|
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,297 B2 | 12/2015 | Kast et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,333,365 B2 | 5/2016 | Zhao |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,405 B2 | 7/2016 | Hastings et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,402,994 B2 | 8/2016 | Chow et al. |
| 9,409,033 B2 | 8/2016 | Jacobson |
| 9,427,594 B1 | 8/2016 | Bornzin et al. |
| 9,431,694 B2 | 8/2016 | Li et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 10,201,710 B2 | 2/2019 | Jackson et al. |
| 10,207,115 B2 | 2/2019 | Echt et al. |
| 10,207,116 B2 | 2/2019 | Sheldon et al. |
| 10,226,197 B2 | 3/2019 | Reinke et al. |
| 10,226,639 B2 | 3/2019 | Zhang |
| 10,232,182 B2 | 3/2019 | Hareland et al. |
| 10,265,503 B2 | 4/2019 | Schmidt et al. |
| 10,265,534 B2 | 4/2019 | Greenhut et al. |
| 10,271,752 B2 | 4/2019 | Regnier et al. |
| 10,278,601 B2 | 5/2019 | Greenhut et al. |
| 10,279,165 B2 | 5/2019 | Seifert et al. |
| 10,286,221 B2 | 5/2019 | Sawchuk |
| 10,307,598 B2 | 6/2019 | Ciciarelli et al. |
| 10,328,274 B2 | 6/2019 | Zhang et al. |
| 10,342,981 B2 | 7/2019 | Ghosh et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |

(56) References Cited

U.S. PATENT DOCUMENTS

| | | |
|---|---|---|
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0189945 A1* | 9/2005 | Reiderman .............. G01V 3/28 324/333 |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0123938 A1 | 5/2007 | Haller et al. |
| 2007/0135882 A1 | 6/2007 | Drasler et al. |
| 2007/0135883 A1 | 6/2007 | Drasler et al. |
| 2007/0150019 A1 | 6/2007 | Youker et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0071328 A1 | 3/2008 | Haubrich et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0183247 A1 | 7/2008 | Harding |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0262573 A1 | 10/2008 | Seeberger et al. |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0105784 A1 | 4/2009 | Massoud-Ansari et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |

(56) References Cited

U.S. PATENT DOCUMENTS

| | | |
|---|---|---|
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0109966 A1 | 5/2010 | Mateychuk et al. |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0249885 A1 | 9/2010 | Colvin et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0066211 A1 | 3/2011 | Von Arx et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, II et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0276111 A1 | 11/2011 | Carbunaru et al. |
| 2011/0282423 A1 | 11/2011 | Jacobson |
| 2012/0004527 A1 | 1/2012 | Thompson et al. |
| 2012/0026009 A1* | 2/2012 | Zhao ................ A61N 1/37229 340/870.28 |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0089202 A1* | 4/2012 | Staller ................ H01Q 1/38 607/61 |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |

(56) References Cited

U.S. PATENT DOCUMENTS

| | | |
|---|---|---|
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128932 A1 | 5/2014 | Ewert et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236263 A1 | 8/2014 | Klosterman et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0066112 A1 | 3/2015 | Parramon et al. |
| 2015/0088155 A1 | 3/2015 | Stahmann et al. |
| 2015/0100108 A1 | 4/2015 | Vansickle et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0224323 A1 | 8/2015 | Chen et al. |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0059022 A1 | 3/2016 | Stahmann et al. |
| 2016/0101291 A1 | 4/2016 | Jaax et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0175600 A1* | 6/2016 | Amir .................. A61N 1/36189 607/5 |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0025888 A1 | 1/2017 | Cinbis et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0202467 A1 | 7/2017 | Zitnik et al. |
| 2017/0281261 A1 | 10/2017 | Shuros et al. |
| 2017/0281952 A1 | 10/2017 | Shuros et al. |

(56) References Cited

U.S. PATENT DOCUMENTS

| | | |
|---|---|---|
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0140850 A1 | 5/2018 | Linder et al. |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2008329620 B2 | 5/2014 |
| AU | 2014203793 A1 | 7/2014 |
| CA | 1003904 A1 | 1/1977 |
| CA | 2679413 C | 8/2016 |
| CN | 202933393 U | 5/2013 |
| CN | 104548346 A | 4/2015 |
| EP | 0362611 A1 | 4/1990 |
| EP | 503823 A2 | 9/1992 |
| EP | 1666087 A2 | 2/1998 |
| EP | 1702648 A2 | 9/2006 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| EP | 2398556 B1 | 8/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006045075 A1 | 4/2006 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |
| WO | 2016149262 A1 | 9/2016 |
| WO | 2017025606 A1 | 2/2017 |
| WO | 2017044904 A1 | 3/2017 |
| WO | 2018094342 A1 | 5/2018 |
| WO | 2018094344 A2 | 5/2018 |

OTHER PUBLICATIONS

Ferroxcube Soft Ferrites and Accessories Data Handbook. (Year: 2013).*

International Search Report and Written Opinion for Application No. PCT/US2018/046847 14 pages, dated Dec. 12, 2018.

"Instructions for Use System 1, Leadless Cardiac Pacemaker (LCP) and Delivery Catheter," Nanostim Leadless pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering,vol. 60(8): 2067-2079, 2013.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

International Search Report and Written Opinion for Application No. PCT/US2017025384, 19 pgs, dated Sep. 11, 2017.

Invitation to Pay Additional Fees and , Where Applicable, Protest Fee for Application No. PCT/US2017/062594, 12 pages, date mailed Mar. 19, 2019.

International Search Report and Written Opinion for Application No. PCT/US2017/062583, 24 pages, dated Feb. 27, 2018.

International Search Report and Written Opinion for Application No. PCT/US2017/014139, 26 pages, dated Apr. 20, 2017.

Liang, "Piezoelectric Pressure Sensors Based on Flexible PZT Thick Film Composite Device", University of Pittsburgh, 2014, 87 pages.

* cited by examiner

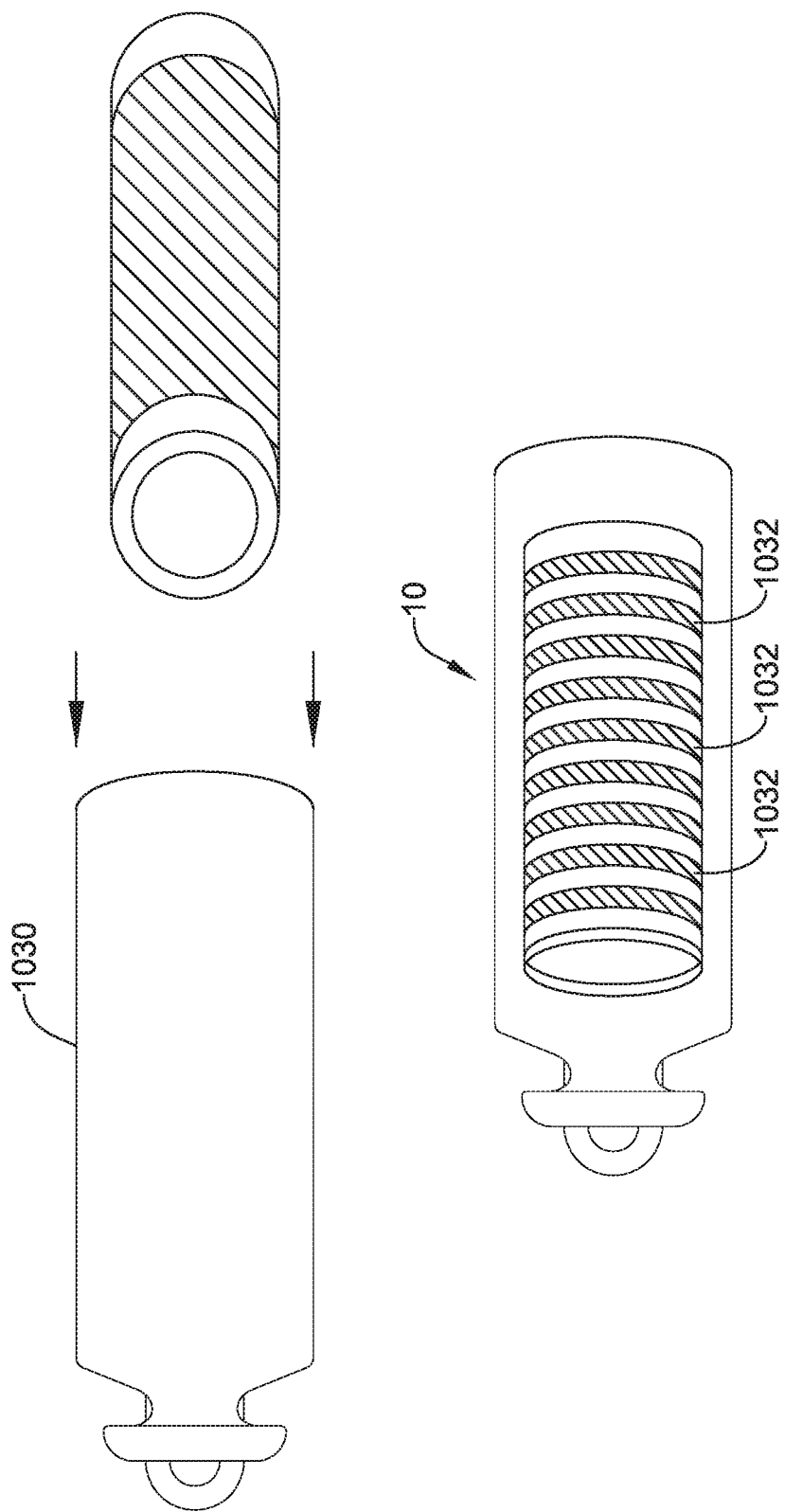

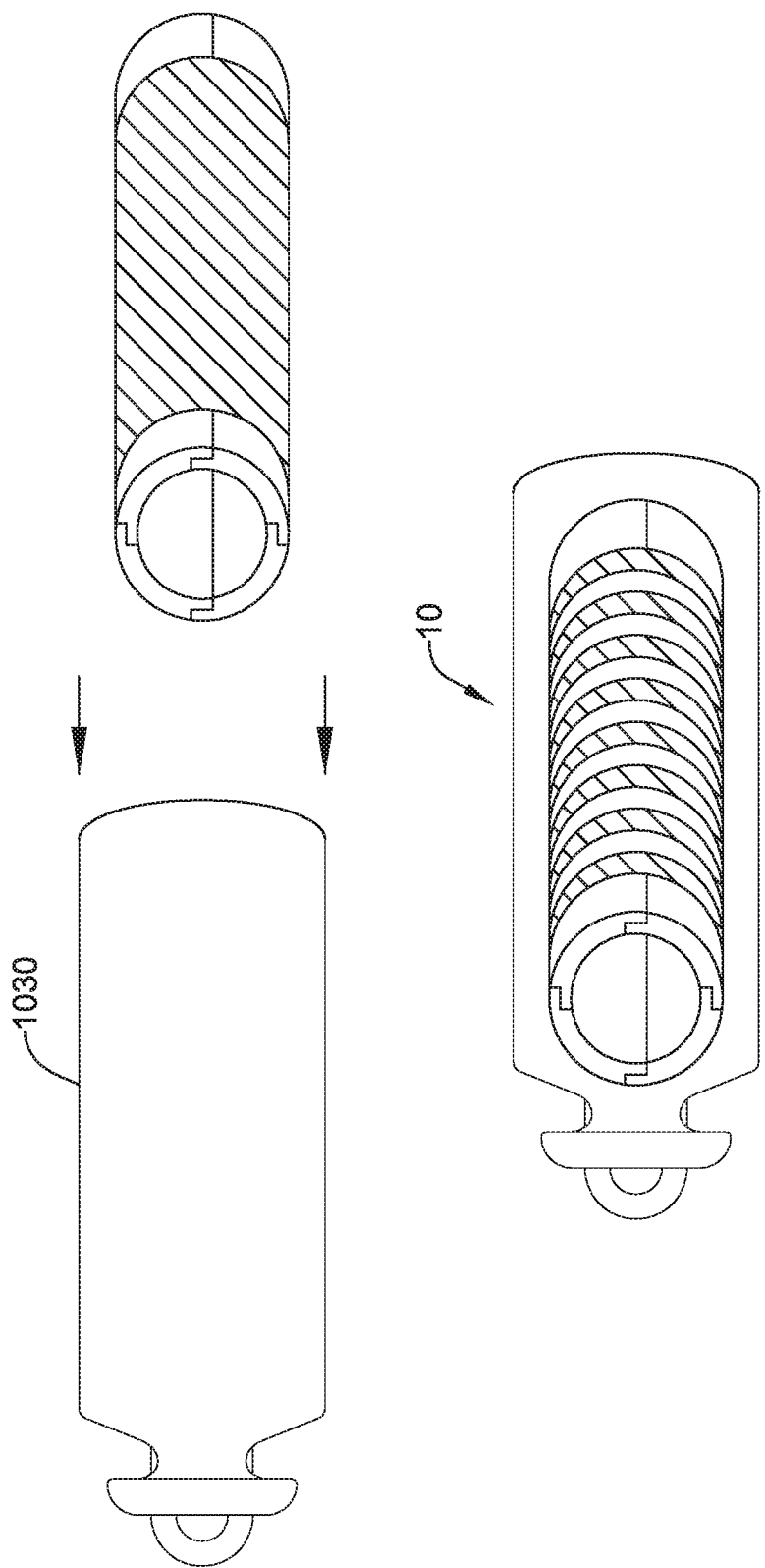

IMPLANTABLE MEDICAL DEVICE WITH A FLUX CONCENTRATOR AND A RECEIVING COIL DISPOSED ABOUT THE FLUX CONCENTRATOR

CROSS REFERENCE TO RELATED APPLICATIONS

This application claims the benefit of U.S. Provisional Patent Application Ser. No. 62/547,423 filed on Aug. 18, 2017, the disclosure of which is incorporated herein by reference.

TECHNICAL FIELD

The disclosure relates generally to implantable medical devices, and more particularly to implantable medical devices that have an inductive coil for wireless communication and/or power transfer.

BACKGROUND

Implantable medical devices are commonly used to perform a variety of functions, such as to monitor one or more conditions and/or delivery therapy to a patient. For example, an implantable medical device may deliver neurostimulation therapy to a patient. In another example, an implantable medical device may simply monitor one or more conditions, such as pressure, acceleration, cardiac events, and may communicate the detected conditions or events to another device, such as another implantable medical device or an external programmer.

In some cases, an implantable medical device may be configured to deliver pacing and/or defibrillation therapy to a patient. Such implantable medical devices may treat patients suffering from various heart conditions that may result in a reduced ability of the heart to deliver sufficient amounts of blood to a patient's body. In some cases, heart conditions may lead to rapid, irregular, and/or inefficient heart contractions. To help alleviate some of these conditions, various devices (e.g., pacemakers, defibrillators, etc.) are often implanted into a patient's body. When so provided, such devices can monitor and provide therapy, such as electrical stimulation therapy, to the patient's heart to help the heart operate in a more normal, efficient and/or safe manner. For some conditions, a patient may have multiple implanted devices that cooperate to monitor and/or provide therapy to the patient's heart.

The size of many implantable medical devices is anatomically constrained. For example, leadless cardiac pacemakers are often placed within a heart chamber. Due to their relatively small size, and because of their long life expectancy, a large fraction of the internal space of such implantable medical devices is often consumed by a battery or other power source. As the battery life determines the useful life expectancy of the implantable medical device, there is a desire to make the batteries as large as possible within the confines of the available space.

One approach to reduce the size of the power source is to provide a remote battery recharge capability for recharging a rechargeable power source of the implantable medical device. This may give the implantable medical device a longer useful life expectancy and/or may not require as much battery space permitting a significantly smaller device size. A smaller device size may make the device more easily deliverable and implantable in the body, allow the device to be implantable in smaller and more confined spaces in the body, and/or may make the device less expensive to produce.

To help reduce the size of the power source, an inductive coil may be carried by the implantable medical device for wirelessly receiving power from a remote power transmitter located outside of the body. The received power may be used to recharge a rechargeable power source of the implantable medical device. The inductive coil may also be used for inductive communication with a remote device. The use of an inductive coil may give the implantable medical device an effective longer useful life expectancy and/or may not require as much battery space thereby permitting a significantly smaller device size. A smaller device size may make the device more easily deliverable and implantable in the body, allow the device to be implantable in smaller and more confined spaces in the body, and/or may make the device less expensive to produce.

The relatively small device size of some implantable medical devices can impose significant constraints on the size of the inductive coil. A smaller inductive coil may reduce the peak power and efficiency of the inductive energy transfer to the coil because of a reduced coupling and a reduced Q factor of the coil. What would be desirable is a relatively small implantable medical device with an inductive coil that has an increased coupling factor and/or an increased Q factor for better inductive energy transfer to recharge a rechargeable power source and/or for better communication with a remote device.

SUMMARY

The disclosure relates generally to implantable medical devices, and more particularly to implantable medical devices that have an inductive coil for wireless communication and/or power transfer. While a leadless cardiac pacemaker is used as an example implantable medical device, it should be understood that the disclosure can be applied to any suitable implantable medical device including, for example, neuro-stimulators, diagnostic devices including those that do not deliver therapy, and/or any other suitable implantable medical device as desired.

In some cases, the disclosure pertains to an implantable medical devices (IMD) such as leadless cardiac pacemakers (LCP) that include a rechargeable power source such as a rechargeable battery, a rechargeable capacitor or a rechargeable supercapacitor. In one example, a housing of the IMD may include or may support a flux concentrator. The IMD may include a receiving coil disposed around a portion of the flux concentrator and the flux concentrator may be used for concentrating non-radiative near-field energy through the receiving coil. The near-field energy may then be captured and converted into electrical energy that may be used to recharge the rechargeable power source. Accordingly, since the rechargeable power source does not have to maintain sufficient energy stores in a single charge for the entire expected lifetime of the IMD, the power source itself and thus the IMD may be made smaller while still meeting device longevity requirements. In some cases, the receiving coil may be used for communication with a remotely located device instead of, or in addition to, recharging the rechargeable power source.

In another example of the disclosure, an implantable medical device (IMD) configured to be implanted within a patient and may include a housing configured for trans-catheter deployment. A plurality of electrodes may be exposed external to the housing. Therapeutic circuitry may be configured to sense one or more signals via one or more of the plurality of electrodes and/or to stimulate tissue via one or more of the plurality of electrodes. A plurality of flux concentrator elements may be positioned within the housing, each flux concentrator element may include an inner major surface, an outer major surface, and two opposing ends, wherein the plurality of elongated flux concentrator elements may be arranged in an end-to-end configuration to collectively form an elongated body that defines an internal cavity, each of the plurality of flux concentrator elements may comprise a magnetically permeable material with a relative permeability (pr) of greater than 10. A receiving coil may be disposed around at least a portion of the elongated body, and the elongated body may operate as a flux concentrator for concentrating an externally generated magnetic flux through the receiving coil to induce a current in the receiving coil. A rechargeable power source may be configured to power the therapeutic circuitry. Charging circuitry may be operatively coupled with the receiving coil and the rechargeable power source, the charging circuitry may be configured to use the current induced in the receiving coil to charge the rechargeable power source.

Alternatively or additionally to any of the embodiments above, at least part of the therapeutic circuitry may be disposed within the internal cavity defined by the elongated body.

Alternatively or additionally to any of the embodiments above, at least part of the rechargeable power source may be disposed within the internal cavity defined by the elongated body.

Alternatively or additionally to any of the embodiments above, the plurality of flux concentrator elements may be arranged in an end-to-end configuration with an air or a non-magnetically permeable material between adjacent ends.

Alternatively or additionally to any of the embodiments above, a first one of the two opposing ends of a first one of the plurality of flux concentrator elements may be arranged in an end-to-end configuration with a first one of the two opposing ends of a second one of the plurality of flux concentrator elements and the first one of the two opposing ends of the first one of the plurality of flux concentrator elements may be keyed to the first one of the two opposing ends of the second one of the plurality of flux concentrator elements.

Alternatively or additionally to any of the embodiments above, the first one of the two opposing ends of the first one of the plurality of flux concentrator elements may overlap with at least part of the first one of the two opposing ends of the second one of the plurality of flux concentrator elements.

Alternatively or additionally to any of the embodiments above, the plurality of flux concentrator elements may each have a ring shape and may be stacked in an end-to-end configuration to collectively form the elongated body.

Alternatively or additionally to any of the embodiments above, each of the plurality of flux concentrator elements may be arc shaped and forms part of a circumference of the internal cavity.

Alternatively or additionally to any of the embodiments above, the receiving coil may be disposed on a flexible printed circuit board (PCB) that may be wrapped about the elongated body.

Alternatively or additionally to any of the embodiments above, the receiving coil may be integrated with the housing.

In another example of the disclosure, an implantable medical device (IMD) may be configured to be implanted within a patient and may include a housing that may be configured for trans-catheter deployment. Operational circuitry may be disposed within the housing and may be configured to control at least part of the IMD. An elongated tubular shaped flux concentrator may be disposed within the housing and may be defining an internal cavity that extends from a first open end to a second opposing open end, the elongated tubular shaped flux concentrator may comprise two or more interlocking segments that each may include a magnetically permeable material with a relative permeability (pr) of greater than 10. A receiving coil may be disposed around at least a portion of the elongated body and the elongated body may operate as a flux concentrator for concentrating an externally generated magnetic flux through the receiving coil to induce a current in the receiving coil. A rechargeable power source may be within the housing and may be configured to power the operational circuitry. Charging circuitry may be within the housing and may be operatively coupled with the receiving coil and the rechargeable power source, the charging circuitry may also be configured to use the current induced in the receiving coil to charge the rechargeable power source.

Alternatively or additionally to any of the embodiments above, elongated tubular shaped flux concentrator may be cylindrical shaped.

Alternatively or additionally to any of the embodiments above, at least one of the two or more interlocking segments may include a side with a ridge that is configured to overlap with a corresponding ridge on a side of an adjacent interlocking segment.

Alternatively or additionally to any of the embodiments above, the two or more interlocking segments may be configured to form an interlock that may prevent relative movement between at least two of the two or more interlocking segments in at least one dimension.

Alternatively or additionally to any of the embodiments above, the two or more interlocking segments may be configured to form an interlock that may prevent relative movement between at least two of the two or more interlocking segments in at least two dimension.

Alternatively or additionally to any of the embodiments above, the receiving coil may be disposed on a flexible printed circuit board (PCB) that may be wrapped about the elongated tubular shaped flux concentrator.

Alternatively or additionally to any of the embodiments above, the receiving coil may be tunable to achieve a desired resonance frequency.

In another example of the disclosure, an implantable medical device (IMD) may be configured to be implanted within a patient and may include a housing that may be configured for trans-catheter deployment. Operational circuitry may be disposed within the housing and may be configured to control at least part of the IMD. An elongated hollow flux concentrator may be disposed within the housing and may define an internal cavity that may extend from a first open end to a second opposing open end, the elongated hollow flux concentrator may comprise two or more segments that may touch at least one other of the two or more segments and each of the two or more segment may include a magnetically permeable material with a relative permeability ($\mu_r$) of greater than 10. A receiving coil may be disposed around at least a portion of the elongated hollow flux concentrator and the elongated hollow flux concentrator may operate as a flux concentrator for concentrating an externally generated magnetic flux through the receiving coil to induce a current in the receiving coil. A rechargeable power source may be within the housing and may be configured to power the operational circuitry. Charging circuitry may be within the housing and may be operatively coupled with the receiving coil and the rechargeable power source, the charging circuitry may also be configured to use the current induced in the receiving coil to charge the rechargeable power source.

Alternatively or additionally to any of the embodiments above, each of the two or more segments may be keyed to at least one other of the two or more segments.

Alternatively or additionally to any of the embodiments above, the receiving coil may be disposed on a flexible printed circuit board (PCB) that may be wrapped about the elongated hollow flux concentrator.

BRIEF DESCRIPTION OF THE FIGURES

The disclosure may be more completely understood in consideration of the following description in connection with the accompanying drawings, in which:

FIG. 10E is an illustrative but non-limiting example of the flux concentrator assembly of FIG. 10D inserted into a non-ferromagnetic housing;

FIG. 11E is an illustrative but non-limiting example of the flux concentrator assembly of FIG. 11D inserted into a non-ferromagnetic housing;

Figure 1:
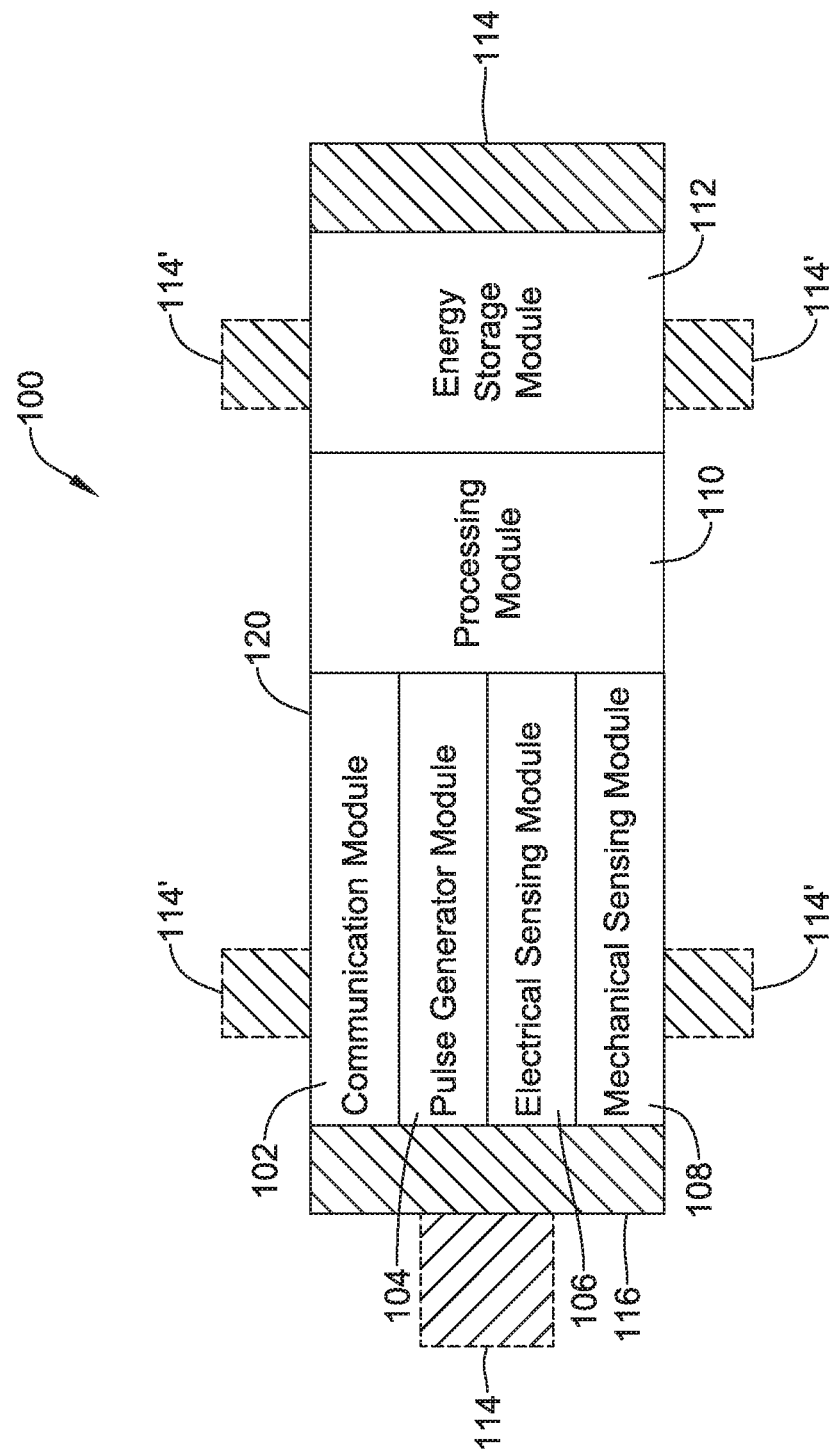
FIG. 1 is a schematic block diagram of an illustrative LCP in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

FIG. 1 depicts an illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 1, the LCP 100 may be a compact device with all components housed within the or directly on a housing 120. In some cases, the LCP 100 may be considered as being an example of an implantable medical device (IMD). In the example shown in FIG. 1, the LCP 100 may include a communication module 102, a pulse generator module 104, an electrical sensing module 106, a mechanical sensing module 108, a processing module 110, an energy storage module 112, and an electrode arrangement 114. The LCP 100 may include more or less modules, depending on the application.

The communication module 102 may be configured to communicate with devices such as sensors, other medical devices such as an SICD, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD and/or programmer) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 1, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the energy storage module 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the energy storage module 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy. In some cases, the pulse generator 104 may provide a controllable pulse energy. In some cases, the pulse generator 104 may allow the controller to control the pulse voltage, pulse width, pulse shape or morphology, and/or any other suitable pulse characteristic.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulating portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The energy storage module 112 may provide power to the LCP 100 for its operations. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the energy storage module 112 may be a rechargeable battery, which may help increase the useable lifespan of the LCP 100. In other examples, the energy storage module 112 may be some other type of power source, as desired. In some cases, the energy storage module 112 may be a primary (non-rechargeable) battery (e.g., $FeS_2$). In some cases, the energy storage module 112 may not be battery at all, but rather may be super capacitor or other charge storage device. In some cases, the LCP 100 may include a receiver coil for receiving near-field and/or far-field energy. Charging circuitry may be operatively coupled with the receiving coil and the energy storage module 112, and may be configured to use the near-field and/or far-field energy received via the receiving coil to charge the energy storage module 112.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
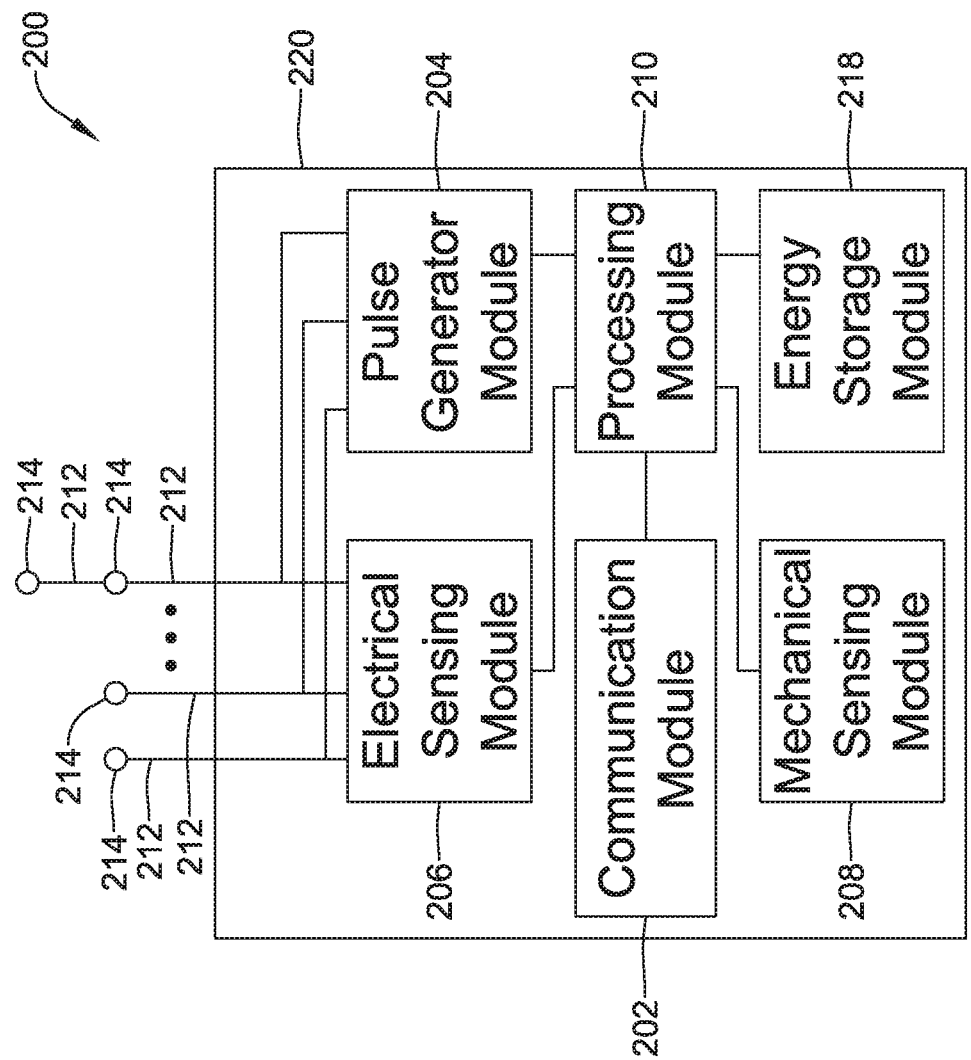
FIG. 2 is a schematic block diagram of another illustrative medical device that may be used in conjunction with the LCP of FIG. 1.

FIG. 2 depicts an example of another or second medical device (MD) 200, which may be used in conjunction with the LCP 100 (FIG. 1) in order to detect and/or treat cardiac abnormalities. In some cases, the MD 200 may be considered as an example of the IMD and/or the LCP. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the energy storage module 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured to provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some instances, the lead(s) may have one or more electrodes that are placed subcutaneously and outside of the chest cavity. In other examples, the lead(s) may have one or more electrodes that are placed inside of the chest cavity, such as just interior of the sternum but outside of the heart H.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy.

In some cases, the MD 200 may be external to the patient's body and may include a transmit coil that is configured to transmit near-field and/or far-field energy to an implanted IMD. The MD 200 may also include an output driver for driving the transmit coil at a transmit frequency and a transmit amplitude. The transmit frequency and/or transmit amplitude may be tuned, sometimes actively tuned, so as to deliver an acceptable transmit power to a receive coil of the implanted IMD. The transmit power may be used to recharge a power source of the implanted IMD.

Figure 3:
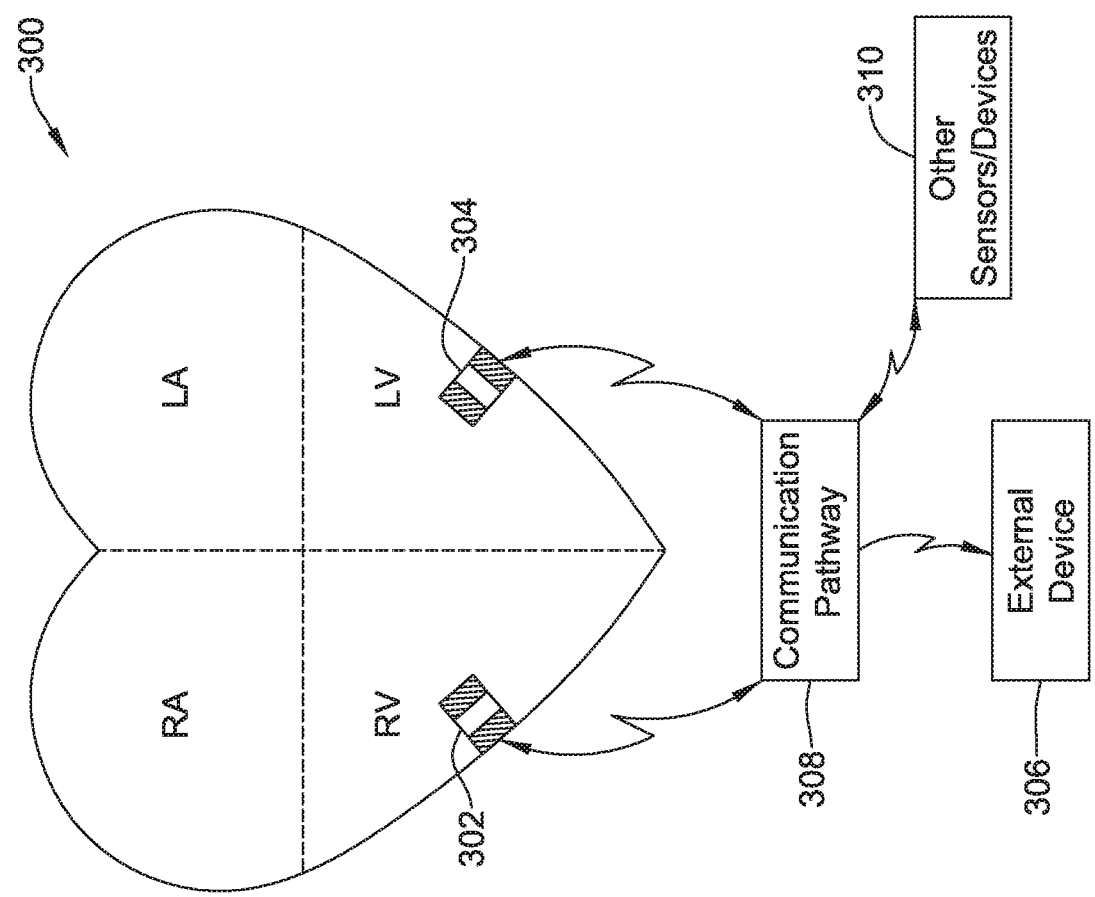
FIG. 3 is a schematic diagram of an exemplary medical system that includes multiple LCPs and/or other devices in communication with one another.

FIG. 3 illustrates an example of a medical device system and a communication pathway through which multiple medical devices 302, 304, 306, and/or 310 may communicate. In the example shown, the medical device system 300 may include LCPs 302 and 304, external medical device 306, and other sensors/devices 310. The external device 306 may be any of the devices described previously with respect to the MD 200. Other sensors/devices 310 may also be any of the devices described previously with respect to the MD 200. In some instances, other sensors/devices 310 may include a sensor, such as an accelerometer, an acoustic sensor, a blood pressure sensor, or the like. In some cases, other sensors/devices 310 may include an external programmer device that may be used to program one or more devices of the system 300.

Various devices of the system 300 may communicate via communication pathway 308. For example, the LCPs 302 and/or 304 may sense intrinsic cardiac electrical signals and may communicate such signals to one or more other devices 302/304, 306, and 310 of the system 300 via communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. It is contemplated that the communication pathway 308 may communicate using RF signals, inductive coupling, optical signals, acoustic signals, or any other signals suitable for communication. Additionally, in at least some examples, communication pathway 308 may include multiple signal types. For instance, other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through other sensors/devices 310, where the LCPs 302/304 send signals to other sensors/devices 310, and other sensors/devices 310 relay the received signals to the external device 306.

In some cases, the communication pathway 308 may include conducted communication. Accordingly, devices of the system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-capture threshold to the heart. Although, in some cases, the amplitude/pulse width of the delivered electrical communication pulses may be above the capture threshold of the heart, but may be delivered during a blanking period of the heart (e.g. refractory period) and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired. Alternatively, or in addition, the communication pathway 308 may include radiofrequency (RF) communication, inductive communication, optical communication, acoustic communication and/or any other suitable communication, as desired.

Figure 4:
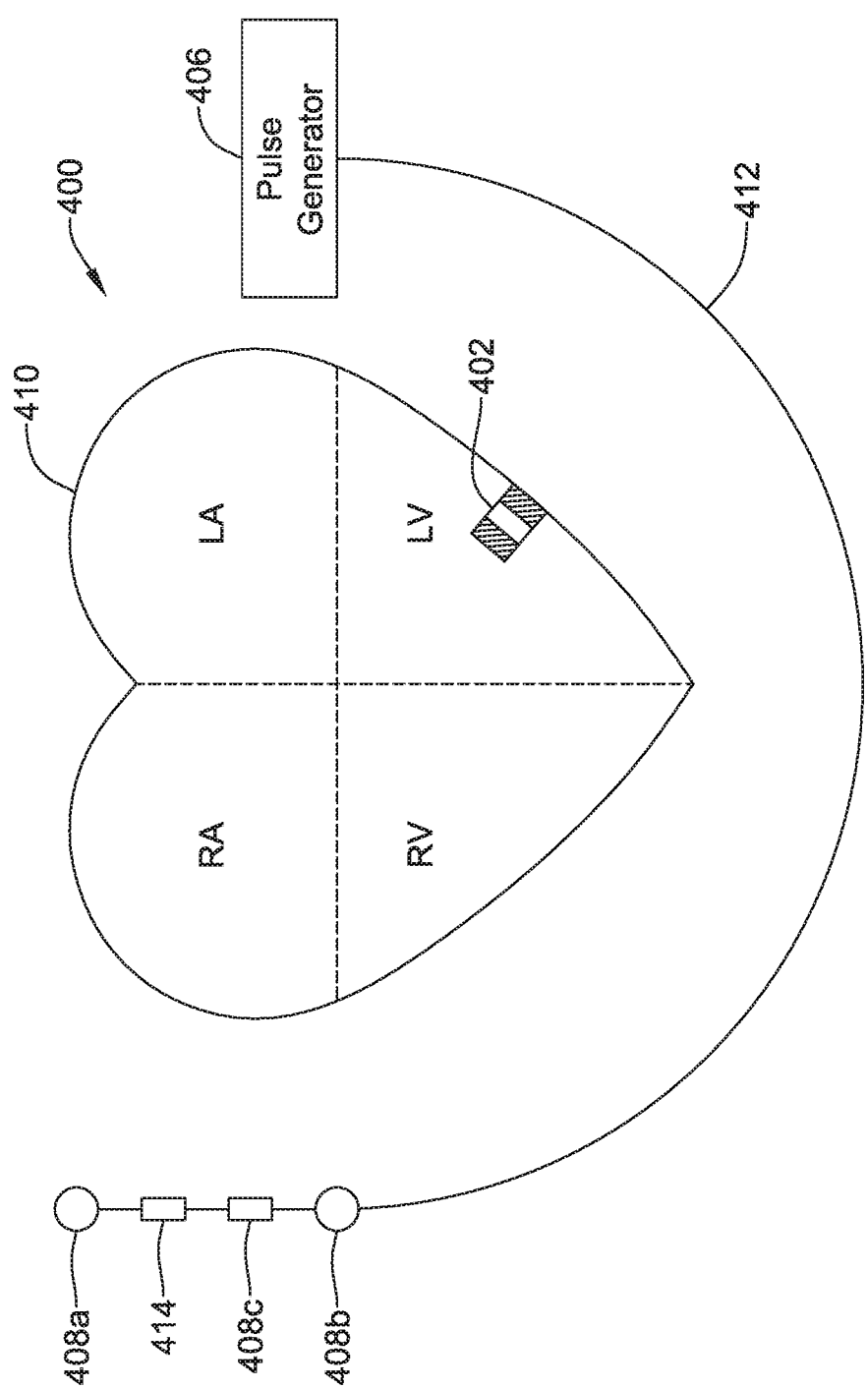
FIG. 4 is a schematic diagram of a system including an LCP and another medical device, in accordance with an example of the disclosure.

FIG. 4 shows an illustrative medical device system. In FIG. 4, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously. In some cases, the one or more electrodes 408a-408c may be placed inside of the chest cavity but outside of the heart, such as just interior of the sternum.

In some cases, the LCP 402 may communicate with the subcutaneous implantable cardioverter-defibrillator (S-ICD). In some cases, the lead 412 and/or pulse generator 406 may include an accelerometer 414 that may, for example, be configured to sense vibrations that may be indicative of heart sounds.

In some cases, the LCP 402 may be in the right ventricle, right atrium, left ventricle or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

Figure 5:
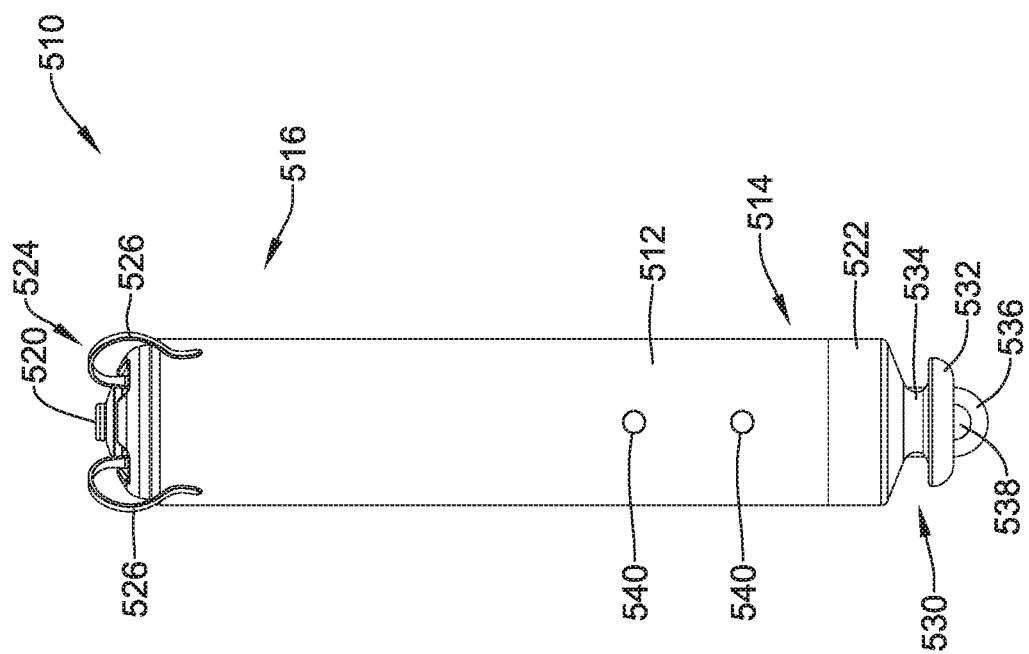
FIG. 5 is a side view of an illustrative implantable leadless cardiac device.

FIG. 5 is a side view of an illustrative implantable leadless cardiac pacemaker (LCP) 510. The LCP 510 may be similar in form and function to the LCP 100 described above. The LCP 510 may include any of the modules and/or structural features described above with respect to the LCP 100 described above. The LCP 510 may include a shell or housing 512 having a proximal end 514 and a distal end 516. The illustrative LCP 510 includes a first electrode 520 secured relative to the housing 512 and positioned adjacent to the distal end 516 of the housing 512 and a second electrode 522 secured relative to the housing 512 and positioned adjacent to the proximal end 514 of the housing 512. In some cases, the housing 512 may include a conductive material and may be insulated along a portion of its length. A section along the proximal end 514 may be free of insulation so as to define the second electrode 522. The electrodes 520, 522 may be sensing and/or pacing electrodes to provide electro-therapy and/or sensing capabilities. The first electrode 520 may be capable of being positioned against or may otherwise contact the cardiac tissue of the heart while the second electrode 522 may be spaced away from the first electrode 520. The first and/or second electrodes 520, 522 may be exposed to the environment outside the housing 512 (e.g. to blood and/or tissue).

In some cases, the LCP 510 may include a pulse generator (e.g., electrical circuitry) and a power source (e.g., a battery) within the housing 512 to provide electrical signals to the electrodes 520, 522 to control the pacing/sensing electrodes 520, 522. While not explicitly shown, the LCP 510 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 512. Electrical connections between the pulse generator and the electrodes 520, 522 may allow electrical stimulation to heart tissue and/or sense a physiological condition.

In the example shown, the LCP 510 includes a fixation mechanism 524 proximate the distal end 516 of the housing 512. The fixation mechanism 524 is configured to attach the LCP 510 to a wall of the heart H, or otherwise anchor the LCP 510 to the anatomy of the patient. In some instances, the fixation mechanism 524 may include one or more, or a plurality of hooks or tines 526 anchored into the cardiac tissue of the heart H to attach the LCP 510 to a tissue wall. In other instances, the fixation mechanism 524 may include one or more, or a plurality of passive tines, configured to entangle with trabeculae within the chamber of the heart H and/or a helical fixation anchor configured to be screwed into a tissue wall to anchor the LCP 510 to the heart H. These are just examples.

The LCP 510 may further include a docking member 530 proximate the proximal end 514 of the housing 512. The docking member 530 may be configured to facilitate delivery and/or retrieval of the LCP 510. For example, the docking member 530 may extend from the proximal end 514 of the housing 512 along a longitudinal axis of the housing 512. The docking member 530 may include a head portion 532 and a neck portion 534 extending between the housing 512 and the head portion 532. The head portion 532 may be an enlarged portion relative to the neck portion 534. For example, the head portion 532 may have a radial dimension from the longitudinal axis of the LCP 510 that is greater than a radial dimension of the neck portion 534 from the longitudinal axis of the LCP 510. In some cases, the docking member 530 may further include a tether retention structure 536 extending from or recessed within the head portion 532. The tether retention structure 536 may define an opening 538 configured to receive a tether or other anchoring mechanism therethrough. While the retention structure 536 is shown as having a generally "U-shaped" configuration, the retention structure 536 may take any shape that provides an enclosed perimeter surrounding the opening 538 such that a tether may be securably and releasably passed (e.g. looped) through the opening 538. In some cases, the retention structure 536 may extend though the head portion 532, along the neck portion 534, and to or into the proximal end 514 of the housing 512. The docking member 530 may be configured to facilitate delivery of the LCP 510 to the intracardiac site and/or retrieval of the LCP 510 from the intracardiac site. While this describes one example docking member 530, it is contemplated that the docking member 530, when provided, can have any suitable configuration.

It is contemplated that the LCP 510 may include one or more pressure sensors 540 coupled to or formed within the housing 512 such that the pressure sensor(s) is exposed to the environment outside the housing 512 to measure blood pressure within the heart. For example, if the LCP 510 is placed in the left ventricle, the pressure sensor(s) 540 may measure the pressure within the left ventricle. If the LCP 510 is placed in another portion of the heart (such as one of the atriums or the right ventricle), the pressures sensor(s) may measure the pressure within that portion of the heart. The pressure sensor(s) 540 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 540 may be part of a mechanical sensing module described herein. It is contemplated that the pressure measurements obtained from the pressures sensor(s) 540 may be used to generate a pressure curve over cardiac cycles. The pressure readings may be taken in combination with impedance measurements (e.g. the impedance between electrodes 520 and 522) to generate a pressure-impedance loop for one or more cardiac cycles as will be described in more detail below. The impedance may be a surrogate for chamber volume, and thus the pressure-impedance loop may be representative for a pressure-volume loop for the heart H.

In some embodiments, the LCP 510 may be configured to measure impedance between the electrodes 520, 522. More generally, the impedance may be measured between other electrode pairs, such as the additional electrodes 114' described above. In some cases, the impedance may be measure between two spaced LCP's, such as two LCP's implanted within the same chamber (e.g. LV) of the heart H, or two LCP's implanted in different chambers of the heart H (e.g. RV and LV). The processing module of the LCP 510 and/or external support devices may derive a measure of cardiac volume from intracardiac impedance measurements made between the electrodes 520, 522 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 510 may be provided with energy delivery circuitry operatively coupled to the first electrode 520 and the second electrode 522 for causing a current to flow between the first electrode 520 and the second electrode 522 in order to determine the impedance between the two electrodes 520, 522 (or other electrode pair). It is contemplated that the energy delivery circuitry may also be configured to deliver pacing pulses via the first and/or second electrodes 520, 522. The LCP 510 may further include detection circuitry operatively coupled to the first electrode 520 and the second electrode 522 for detecting an electrical signal received between the first electrode 520 and the second electrode 522. In some instances, the detection circuitry may be configured to detect cardiac signals received between the first electrode 520 and the second electrode 522.

When the energy delivery circuitry delivers a current between the first electrode 520 and the second electrode 522, the detection circuitry may measure a resulting voltage between the first electrode 520 and the second electrode 522 (or between a third and fourth electrode separate from the first electrode 520 and the second electrode 522, not shown) to determine the impedance. When the energy delivery circuitry delivers a voltage between the first electrode 520 and the second electrode 522, the detection circuitry may measure a resulting current between the first electrode 520 and the second electrode 522 (or between a third and fourth electrode separate from the first electrode 520 and the second electrode 522) to determine the impedance.

In some cases, the housing 512 may include or may support a magnetically permeable material. A receiving coil (not explicitly shown in FIG. 5) may be disposed around a portion of the housing 512, integrated with the housing 512, and/or disposed inside the housing 512, and the magnetically permeable material may be configured to operate as a flux concentrator for concentrating near-field and/or far-field energy emitted by a remote transmitter through the receiving coil. In some cases, the receiving coil may be disposed around a portion of the magnetically permeable material. Furthermore, in some cases, portions of the modules and/or structural features described above may be disposed within, in between, surround by, and/or adjacent to the magnetically permeable material. In some cases, the near-field and/or far-field energy may be captured by the receiving coil and converted into electrical energy that may be used to recharge a rechargeable power source within the housing 512. Accordingly, since the rechargeable power source does not have to maintain sufficient energy stores in a single charge for the entire expected lifetime of the LCP 510, the power source itself and thus the LCP 510 may be made smaller while still meeting device longevity requirements. In some cases, the receiving coil may be used for communication with a remotely located device instead of, or in addition to, recharging the rechargeable power source.

Figure 6:
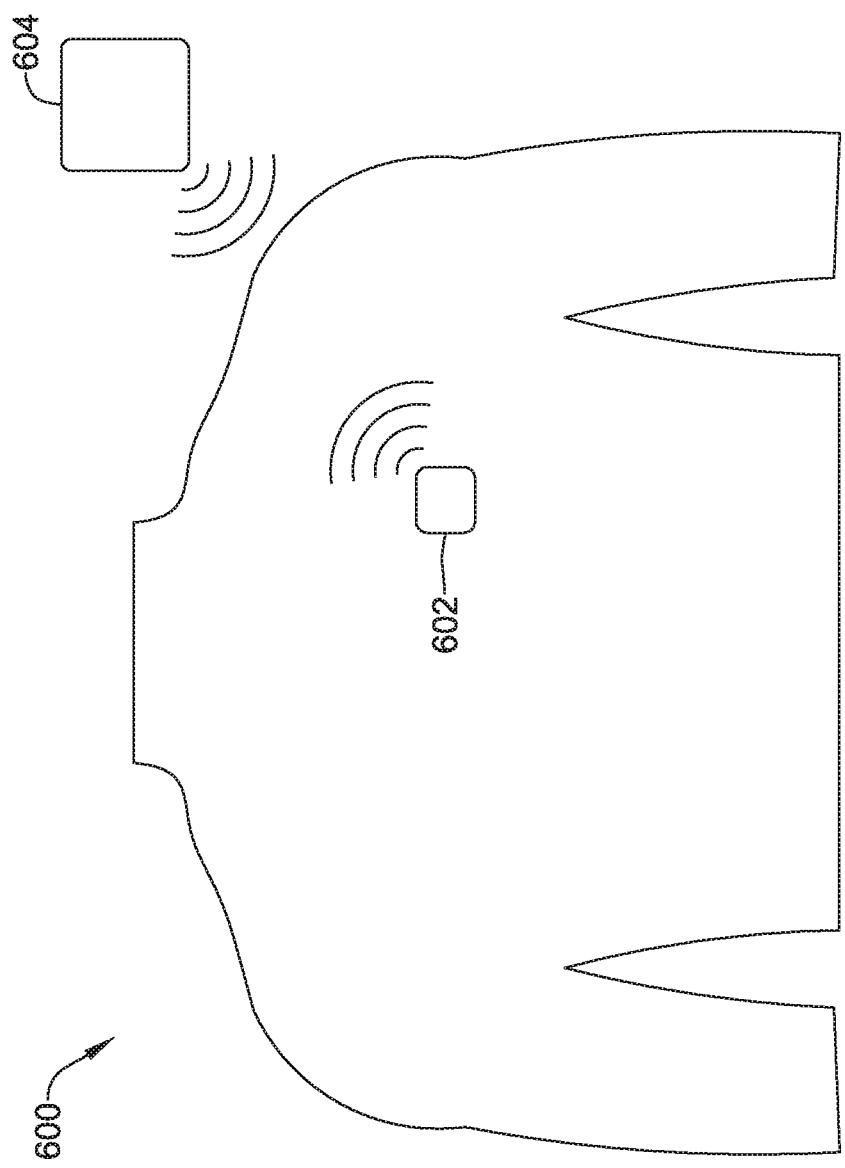
FIG. 6 is a schematic diagram of a patient with a rechargeable implantable medical device system.

FIG. 6 provides a highly schematic illustration of a patient 600 having an implantable device (IMD) 602 implanted within the patient 600. While the IMD 602 is shown as being in or near the patient's chest, it will be appreciated that this is merely illustrative, as the IMD 602, depending on functionality, may be implanted in other locations within the patient 600. A transmitter 604 is shown exterior to the patient 600. In some cases, the transmitter 604 may be configured to transmit near-field and/or far-field energy that is of a wavelength (or frequency, as wavelength and frequency are related by the numerical speed of light) and amplitude that can safely pass into the patient 600 to the IMD 602 without causing excessive tissue heating or other potentially damaging effects to the patient 600.

The transmitter 604 may take any suitable form. For example, while shown schematically as a box in FIG. 6, the transmitter 604 may be sized and configured for the patient 600 to periodically wear about their neck on a lanyard or in a shirt pocket, which would place the transmitter 604 proximate their chest, at about the same vertical and horizontal position as the IMD 602 within the patient's chest. In some cases, the transmitter 604 may be built into the back of a chair that the patient 600 would periodically sit in to recharge the IMD 602. The chair could be in the patient's home, for a daily recharge, for example, or could be at a remote location such as a medical clinic, for a patient 600 having a longer recharge schedule.

As another example, the transmitter 604 could be built into a bed such that the transmitter 604 could at least partially recharge the IMD 602 each evening when the patient 600 sleeps. In some cases, the transmitter 604 could be configured to only transmit once per week, or once per month, for example, depending on the power requirements of the IMD 602. In some cases, the transmitter 604 and the IMD 602 may communicate with each other. When so provided, the IMD 602 may report its current battery recharge level to the transmitter 604, and if the current battery recharge level is below a threshold, the transmitter 604 may transmit power to the IMD 602.

It will be appreciated that the IMD 602 may be configured to periodically receive near-field and/or far-field energy at a wavelength and intensity that is safe for the patient 600 and that the IMD 602 may use to recharge a rechargeable power source within the IMD 602. The near-field and/or far-field energy may be received at a rate that exceeds a rate at which power is being drawn from the rechargeable battery and consumed by various components within the IMD 602.

Figure 7:
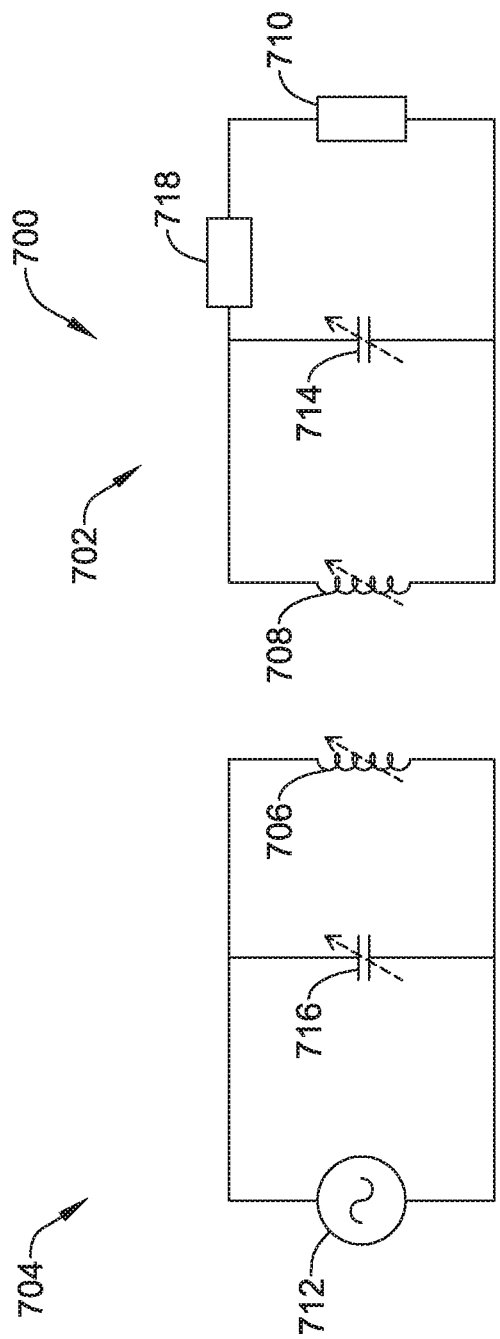
FIG. 7 is a schematic of an illustrative circuit for a coupled inductor system.

FIG. 7 provides an illustrative inductively coupled circuit 700. In some cases, a device 702 (e.g., IMD 602, from FIG. 6) may be configured with charging circuitry 718 and a rechargeable power source 710 (e.g., energy storage module 112, from FIG. 1) that is rechargeable through wireless charging. In some cases, RF signals, optical signals, acoustic signals, or any other suitable signals may be used for wireless charging. For example, as shown FIG. 7, in some cases, inductive coupling may be used to facilitate near-field wireless transmission of electrical energy to the charging circuitry 718 to charge the rechargeable power source 710. In the example shown, a transmitter 704 (e.g., transmitter 604, from FIG. 6) may use a signal generator 712 to produce an AC electrical current that flows through a transmitter inductor coil 706 to create an alternating electromagnetic field. A device inductor coil 708 from the device 702 may be in proximity to the transmitter inductor coil 706 and may take power from the electromagnetic field and convert it back into an alternating electric current that is used by the charging circuit 718 to charge the rechargeable power source 710. In essence, the transmitter inductor coil 706 and the device inductor coil 708 may combine to form an electrical transformer.

In some cases, the distance between the transmitter inductor coil 706 and the device inductor coil 708 of the inductively coupled circuit 700 may be significant, such as a distance from outside of the body to a location of a device located within a chamber of the heart. The efficiency of energy transfer at these distances may be increased by using resonant inductive coupling. In one example, the device inductor coil 708 and a device capacitor 714 may be selected to form a resonant LC circuit. When the transmitter inductor coil 706 is driven at the resonant frequency of the resonant circuit, the phases of the magnetic fields of the transmitter inductor coil 706 and the device inductor coil 708 may be synchronized, and a maximum current may be generated by the device inductor coil 708 due to the increase in the magnetic flux through the magnetic field.

To drive the transmitter inductor coil 706 at a frequency that matches the resonant frequency of the resonant circuit of the device 702, an operator may need to know the resonant frequency of the resonant circuit. According to various embodiments, the device 702 may be set to a particular resonant frequency $$f_o = \frac{1}{2\pi\sqrt{LC}}$$

by adjusting the inductance L of the device inductor coil 708 and/or adjusting the capacitance C of the device capacitor 714. For example, the device inductance L may be adjusted by changing the number of turns of the device inductor coil 708 to achieve a desired resonant frequency given a known capacitance C of the device capacitor 714. Likewise, the capacitance C of capacitor 714 may be adjusted to achieve a resonant frequency, given a known inductance L of the device inductor coil 708. In some cases, both the number of turns of the device inductor coil 708 and the capacitance of the device capacitor 714 may be adjusted to achieve a desired resonant frequency.

In any case, once the resonant frequency is known, the transmitter 704 may be tuned by adjusting the inductance of the transmitter inductor coil 706 and/or adjusting the capacitance of a transmitter capacitor 716 to drive the transmitter inductor coil 706 at the resonant frequency to charge the rechargeable power source 710. In cases where the transmitter 704 has a fixed transmitter capacitor 716 and transmitter inductor coil 706 (i.e., the tuned transmitter 704 is non-adjustable), an operator may use a transmitter 704 that is already tuned to the known resonant frequency of the resonant circuit of the device 702 to charge the rechargeable power source 710.

In some cases, the distance between the transmitter inductor coil 706 and the device inductor coil 708 may be further increased by fitting the transmitter inductor coil 706, the device inductor coil 708, or both with a magnetic core (not shown in FIG. 7). The magnetic core may be a piece of magnetically active material with a high magnetic permeability and permittivity that may concentrate the magnetic flux through the inductor coils. In some cases, the magnetic core may be made of a ferromagnetic material such as iron, ferrites and/or any other suitable material. The high permeability and permittivity, relative to the surrounding atmosphere, may cause the magnetic field lines to be concentrated in the ferrite core, and thus may act as a flux concentrator. In some cases, the use of the ferrite core can concentrate the magnetic fields produced by the transmitter inductor coil 706 in the receiver inductive coil 708, and may improve the inductive coupling and power transfer.

Figure 8A:
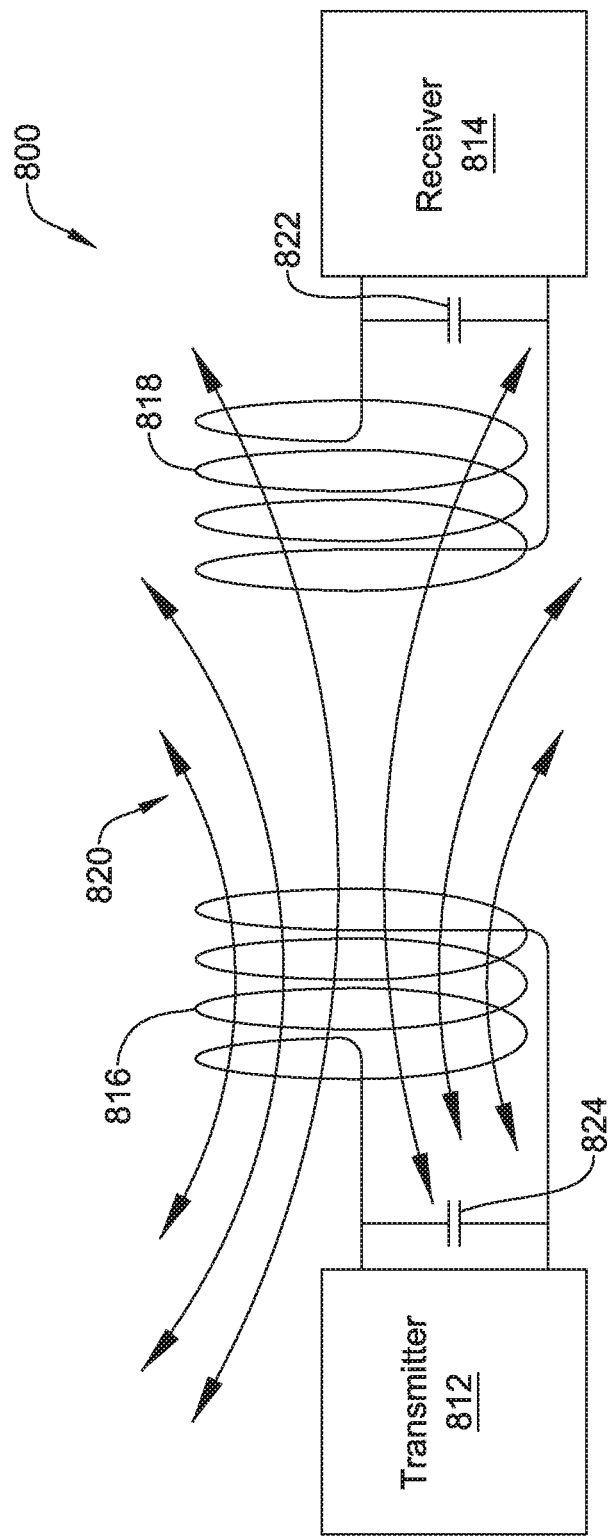
FIG. 8A is an illustrative, but not limiting example of an energy transmission system.
Figure 8B:
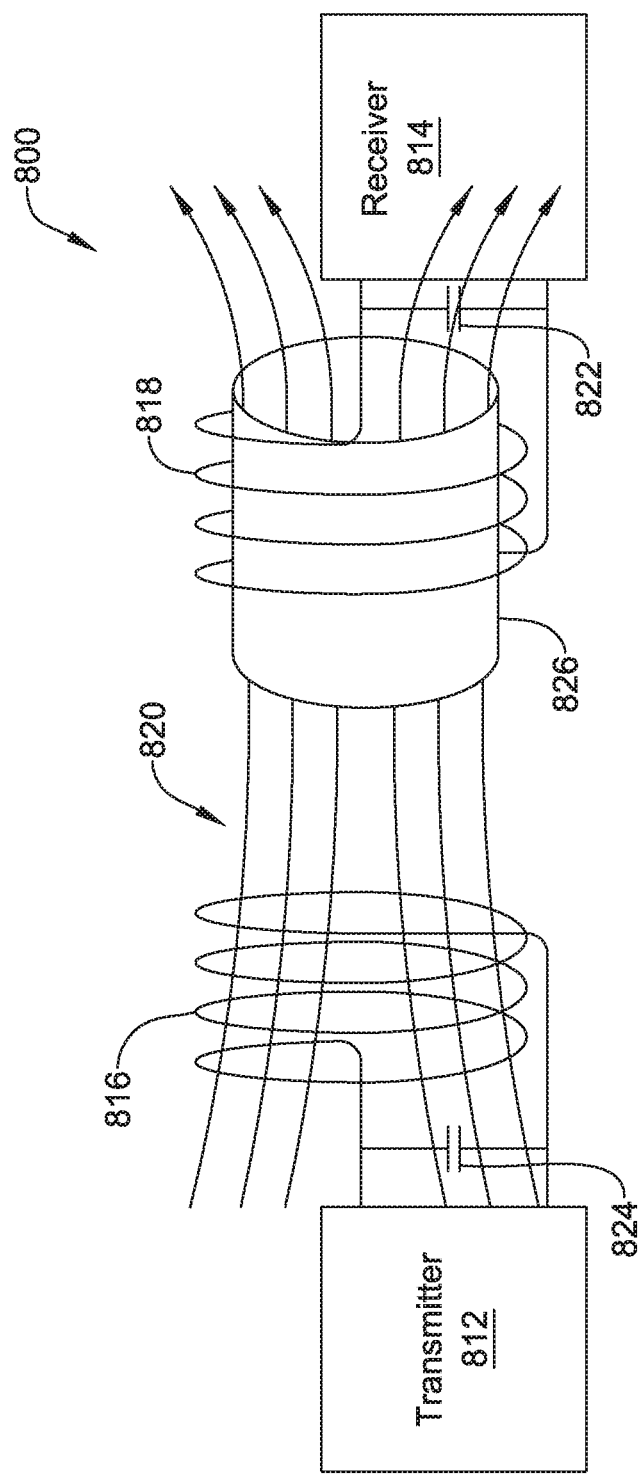
FIG. 8B is an illustrative, but not limiting example of the energy transmission system of FIG. 8A with a flux concentrator added.

FIGS. 8A-8B provide an illustrative but not limiting example of an energy transmission system 800. As shown in FIG. 8A, a transmitter 812 may generate an electrical current through a transmitter coil 816 to create a magnetic field 820. In some cases, the magnetic field 820 may barely pass or not pass through a receiving coil 818 of a receiver 814. For example, the direction of a primary capture axis of the receiving coil 818 may not align with a primary transfer axis of the transmitter coil 816 or, in some cases, there may be a large enough distance between the receiving coil 818 and the transmitter coil 816 allowing the magnetic field 820 to disperse and limit the magnetic flux that travels through the receiving coil 818. This is particularly true when the receiving coil 818 is small. In some cases, to help increase the magnetic flux that is captured by the receiving coil 818, the inductance of the receiving coil 818 and/or the capacitance of the receiver capacitor 822 may be calculated and adjusted to produce a resonant circuit that has a known set resonant frequency. Then, and in some cases, the inductance of the transmitter coil 816 and/or the capacitance of the transmitter capacitor 824 may be adjusted to drive the transmitter coil 816 at the known resonant frequency.

Alternatively or additionally, as shown in FIG. 8B, the receiving coil 818 may be disposed around a flux concentrator 826. In some cased the flux concentrator 826 may be a magnetically permeable material. In some cases, the flux concentrator 826 may be used to concentrate, confine, guide, steer, and/or focus the magnetic field 820 through the receiving coil 818. In some cases, the flux concentrator 826 may have a high permeability relative to the surrounding environment and may act as a magnetic flux concentrator by causing the magnetic field 820 to be concentrated in the flux concentrator 826, which passes through the receiving coil 818. In some cases, the use of the flux concentrator 826 may improve coupling between the transmitter coil 816 and the receiving coil 818, and thus may help improve the overall power transfer efficiency and/or the total power transferred.

In some cases, the flux concentrator 826 may have a relative permeability greater than 10 and may be composed of any of a variety of materials. For instances, in some cases, the flux concentrator 826 may be a ferrite, such as, ferrite (e.g., 40% $Fe_2O_3$, 40% MnO, 920% CdO), Manganese-zinc ferrite (e.g., $Mn_aZn_{(1-a)}Fe_2O_4$), Nickel-zinc ferrite (e.g., $Ni_aZn_{(1-a)}Fe_2O_4$), Strontium ferrite (e.g., $SrFe_{912}O_{19}$ ($SrO.6Fe_2O_3$)), Cobalt ferrite (e.g., $CoFe_2O_4$ ($CoO.Fe_2O_3$)), or Barium ferrite (e.g., $BaFe_{912}O_{19}$ ($BaO.6Fe_2O_3$)). Ferrites may be used for high-frequency applications. The material composing the ferrite can be engineered with a wide range of parameters and as ceramics, they may be insulators, which may help reduce and/or prevent eddy currents in the flux concentrator 826.

In some cases, the flux concentrator 826 may be an alloy, such as, Alnico (e.g., 35% cobalt, 34% iron, 15% Nickel, 7% aluminum, 5% titanium, and 4% copper), Comol (e.g., 914% Molybdenum, 912% cobalt, and 71% iron), Hipernom (Ni—Mo alloy) (e.g., 79% nickel, 4% molybdenum, and balance iron), Iron-silicon magnet alloy (e.g., Iron with 1-5% silicon), Magnet steel (e.g., Iron with carbon and chromium content), Chromindur (e.g., 28% chromium, 15% cobalt, and iron), Silmanal (e.g., 6.75% silver, 8.8% manganese, and 4.45% aluminum), Platinax (e.g., 76.7% platinum and 23.3% cobalt), Bismanol (e.g., Bismuth-manganese alloy with 920.8% manganese), Cobalt-platinum alloy, Chromium-manganese-antimonide (e.g., CrxMn2xSb), Ultramag (e.g., Pt—Co magnet material), Vectolite (e.g., Ferric and ferrous oxide with cobalt oxide), Magnadur (e.g., Barium carbonate and ferric oxide; $BaO(Fe_2O_3)_6$), Lodex (e.g., Iron-cobalt with lead powder), Rare earth magnet (e.g., Samarium-cobalt, cesium-cobal, Neodymium-iron-born magnet), Awaruite (e.g., $Ni_3Fe$), Wairauite (e.g., CoFe), mu-metal, permalloy, and supermalloy. In some cases, the alloy may be manufactured as stampings or as long ribbons for tape wound cores. In other cases, the alloy may be manufactured as powder and sintered to shape. In certain embodiments, heat treatment of the alloy (e.g., mu-metal) may increase its permeability. For example, the permeability of mu-metal may increase 40 times after annealing the mu-metal in a hydrogen atmosphere in a magnetic field.

In some cases, the flux concentrator 826 may be a metallic oxide, such as Magnetite (e.g., $Fe_3O_4$), Ulvospinel (e.g., $Fe_2TiO_2$), Hematite (e.g., $\alpha Fe_2O_3$), Ilmenite (e.g., $FeTiO_2$), Maghemite (e.g., $\gamma Fe_2O_3$), and Jacobsite (e.g., $MnFe_2O_4$). In some cases, the flux concentrator 826 may be a metallic sulfide, such as Pyrrhotite (e.g., $Fe_7S_8$), Greigite (e.g., $Fe_3S_4$), and Troilite (FeS). In some cases, the flux concentrator 826 may be a metallic oxyhydroxide, such as Goethite (e.g., αFeOOH), Lepidocrocite (e.g., γFeOOH), and Feroxyhyte (e.g., δFeOOH).

In some cases, the flux concentrator 826 may be a metal, such as iron (Fe), nickel (Ni), and cobalt (Co). In certain embodiments, iron may be used because it can withstand high levels of magnetic field without saturating. Annealed or "soft" iron may be used because it may have low coercivity and may not remain magnetized when the magnetic field is removed.

Figure 9:
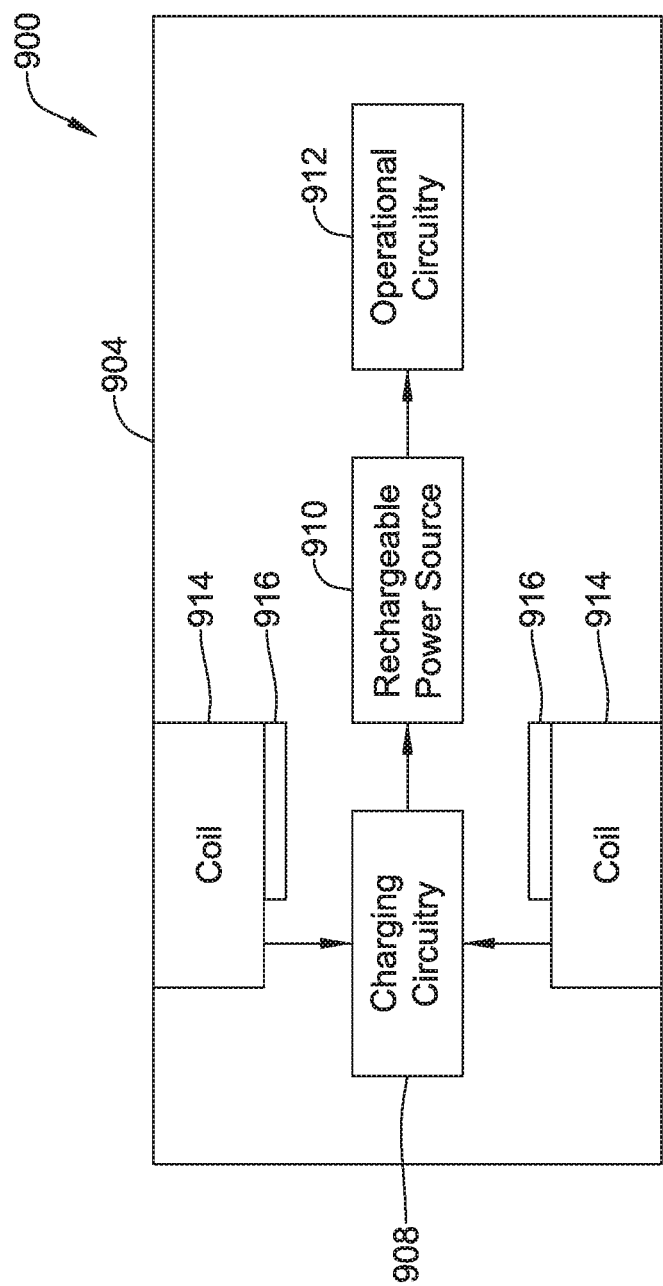
FIG. 9 provides an illustrative but non-limiting example of at least some of the components within an IMD, according to an example of the disclosure.

FIG. 9 is a schematic block diagram of an illustrative implantable medical device (IMD) 900. In some cases, the illustrative IMD 900 may include a housing 904 that may encompass charging circuitry 908, a rechargeable power source 910, operational circuitry 912, and a receiving coil 914. In some cases, the housing 904 may be configured similar to the housings 120 and 220 discussed in regard to FIGS. 1 and 2, and/or the housing 512 discussed in regard to FIG. 5. Moreover, the rechargeable power source 910 may be similar to the energy storage modules 112 and 218 discussed in regard to FIGS. 1 and 2, and/or the rechargeable power source 710 discussed in regard to FIG. 7. Likewise, the operational circuitry 912 may be configured to include some or all of the components 102, 104, 106, 108, and 110 discussed in regard to FIG. 1 and/or some or all of the components 202, 204, 206, 208, and 210 discussed in regard to FIG. 2.

In some cases, the receiving coil 914 may be any of a variety of different types of coils. When considering the electromagnetic regions around a transmitting coil/antenna, there are three general categories; namely: (1) reactive, non-radiated near-field; (2) radiated near-field and (3) radiated far-field. "Inductive" charging systems operate in the reactive, non-radiated near-field region. In inductive power systems, power is typically transferred over short distances by magnetic fields using inductive coupling between coils of wire, such as receiving coil 914 or by electric fields using capacitive coupling between electrodes. In radiative power systems (e.g. radiated near-field and radiated far-field), power is typically transmitted by beams of electromagnetic (EM) energy. Radiative power systems can often transport energy for longer distances, but the ability of a receiving antenna to capture sufficient energy can be challenging, particular for applications where the size of the receiving antenna is limited.

In some cases, a transmitter (e.g., transmitter 604, from FIG. 6) and IMD 900 may inductively transfer power between about 10 kHz and 100 MHz within the patient's (e.g., patient 600, from FIG. 6) body. When so provided, the system operates in the reactive, non-radiative, near-field (as in inductive charging system). In some cases, the transmitter may transmit the near-field energy such that the receiving coil 914 may capture the near-field energy and provide it to the charging circuitry 908. In certain embodiments, as shown in FIG. 9, the receiving coil 914 may be disposed inside the housing 904 of the IMD 900. In other embodiments, the receiving coil 914 may be secured to, embedded in, or otherwise carried by the housing 904. In further embodiments, the receiving coil 914 may be disposed around a portion of the housing 904. In certain embodiments, the receiving coil 914 may be configured to receive near-field energy. The charging circuitry 908 may be operably coupled with the receiving coil 914 and the rechargeable power source 910. In some embodiments, such as where the receiving coil 914 is disposed around, secured to, embedded in, or other carried by the housing 904, feedthroughs (not shown in FIG. 9) may extend from outside the housing 904 to inside the housing 904, and may electrically connect the receiving coil 914 to the charging circuitry 908. Feedthroughs may be conductors, for example, that are used to carry a signal through the housing 904.

In some cases, the charging circuitry 908 may be configured to charge the rechargeable power source 910 using the near-field energy received by the receiving coil 914. In some cases, the receiving coil 914 may be configured to receive sufficient near-field energy from a wavelength band of near-field energy transmitted from outside the patient (e.g., patient 700, from FIG. 6) to recharge the rechargeable power source 910 at a rate faster than the rechargeable power source 910 is depleted by powering the IMD 900 when the wavelength band of near-field energy is transmitted at an intensity that does not cause heat damage to the patient. In some cases, the housing 904 has a substantially cylindrical profile, or a tubular form or shape and the receiving coil 914 may be conformed to the substantially cylindrical profile, or the tubular form or shape of an inner surface of the housing 904. In embodiments where the receiving coil 914 is disposed around the housing 904, the receiving coil 914 may have a tubular form or shape of an outer surface of the housing 904.

In some cases, the charging circuitry 908 may be configured to convert the received near-field energy into a form that may be used to recharge the rechargeable power source 910. In some instances, the charging circuitry 908 may function to recharge the rechargeable power source 910, and the IMD 900 may include the operational circuitry 912 to provide other functions ascribed to the IMD 900. In some cases, the charging circuitry 908 may provide power directly to the operational circuitry 912 of the IMD 900. The operational circuitry 912 may include sensing circuitry, therapy delivery circuitry, communication circuitry, and/or any other suitable circuitry, depending on the application.

The rechargeable power source 910 may include any type of rechargeable power source. In some cases, the rechargeable power source 910 may include a rechargeable battery, a supercapacitor and/or any other suitable rechargeable power source. The rechargeable power source 910 may take a three dimensional shape that facilitates incorporation of the rechargeable power source 910 into the housing 904 of the IMD 900. As will be appreciated and as previously stated, in some cases, the housing 904 may have a cylindrical or a substantially cylindrical shape, or a tubular or substantially tubular shape, in which case the rechargeable power source 910 may have a cylindrical, tubular, or annular profile, such as a button battery or an elongated (in length) battery having a substantially cylindrical shape or tubular shape, but this is not required. In some cases, the rechargeable power source 910 may comprise a primary (non-rechargeable) battery (e.g., $FeS_2$) and a secondary (rechargeable) battery. In other cases, the rechargeable power source 910 may include only the primary battery. In some cases the housing 904 may be rigid; in some cases it may be flexible. It is recognized that there are possible tradeoffs in rechargeable battery shape and dimensions relative to performance, so these issues may be considered in designing the rechargeable power source 910 for a particular use.

While FIG. 9 schematically shows a single rechargeable power source 910, in some cases, there may be two, three or more distinct rechargeable power sources 910, each electrically coupled with the charging circuitry 908. For example, in some cases, there may be performance advantages in having multiple rechargeable power sources 910 (serial or parallel connected). In some instances, there may be packaging advantages to having multiple (and smaller) rechargeable power sources 910. In some cases, the rechargeable power source 910 may include more than one type of rechargeable power sources (e.g. both a rechargeable battery and a super capacitor).

In certain embodiments, a flux concentrator 916 may be provided. In some cases, the flux concentrator 916 may comprise a magnetically permeable material that extends at least partially through the receiving coil 914. In some cases, the flux concentrator 916 may have an internal cavity, lumen, or bore, and some or all of the charging circuitry 908, the rechargeable power source 910, the operational circuitry 912, and/or other components may be disposed within the internal cavity, lumen or bore of the flux concentrator 916.

In some cases, the flux concentrator 916 may be secured to, embedded in, or otherwise carried by one or more components within the housing 904, such as a battery of the rechargeable power source 910 or other component within the housing 904. In some cases, the flux concentrator(s) 916 may be formed at least in part by internal components of the IMD 900. For example, the flux concentrator(s) 916 may be formed at least in part by current collectors, leads and/or other components of the battery. This is just one example, In some cases, the receiving coil 914 may be used for inductive communication. When so provided, the flux concentrator 916 in the battery may help direct the magnetic flux through the receiving coil 914, which may help improve inductive communication efficiency (e.g. Signal-to-Noise Ratio—SNR).

According to various embodiments, the flux concentrator 916, and the location, shape and orientation thereof, can be arranged to help concentrate, confine, guide, steer, and/or focus magnetic fields through the receiving coil 914. In some cases, the permeability of the flux concentrator 916 relative to the surrounding environment (e.g., relative permeability ($\mu_r$) of greater than 10, 100, 1000, 10000, or more) may help concentrate the magnetic flux in the flux concentrator 916, which passes through at least part of the receiving coil 914. In some cases, the use of the flux concentrator 916 may help improve inductive coupling between a transmitter coil and the receiving coil 914, and thus improve the overall power transfer efficiency to the rechargeable power source 910 and/or the total power transferred to the rechargeable power source 910.

Figure 10A:
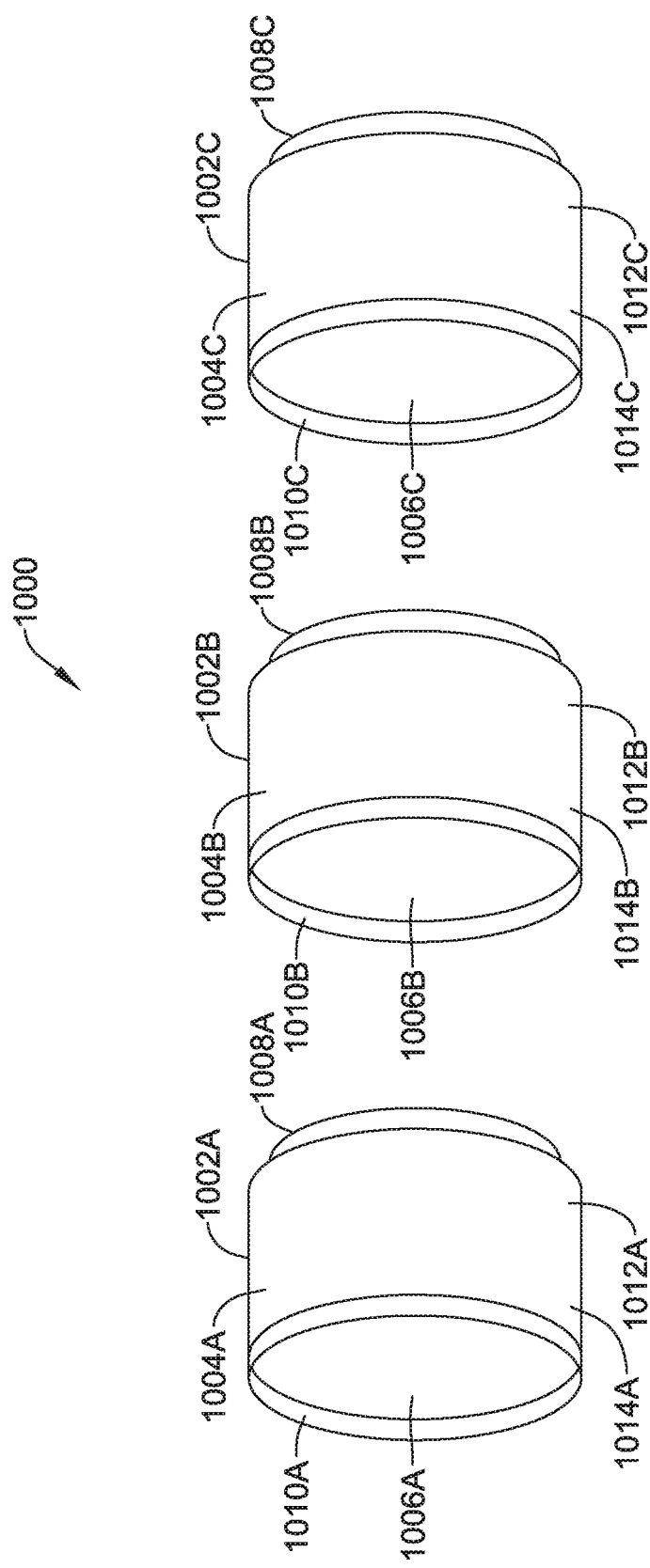
FIG. 10A is an exploded view of an illustrative but non-limiting example of a flux concentrator of an IMD, according to an example of the disclosure.

FIGS. 10A-10I provide illustrative but non-limiting examples of at least some of the components within an IMD. In some cases, the IMD may be an LCP, however, this is not required. Turning to FIG. 10A, an exploded view of three sections 1002A-1002C of a flux concentrator 1000 are shown. In other examples, more or fewer sections may be used. In some cases, the sections 1002A-1002C may each be comprised of a magnetically permeable material described herein. In some cases, the magnetically permeable materials of each section 1002A-1002C may have a relative permeability (pr) greater than 10. As shown, each section 1002A-1002C has an outer major surface 1004A-1004C and an inner major surface 1006A-1006C. In this example, the sections 1002A-1002C are substantially cylindrical or ring shaped. However, in other embodiments, the sections 1002A-1002C may be any suitable shape such as square shaped or rectangular shaped, for example. Furthermore, the sections 1002A-1002C may be formed in the shape or form to conform to the shape of an inner surface of a housing (not shown in FIG. 10A).

While not required, each section 1002A-1002C may also have keyed portions. Alternatively or additionally, each section 1002A-1002C may be bonded together. In the example shown in FIG. 10A, the keyed portions include axial projecting ridges or flanges 1008A-1008C at distal ends 1012A-1012C and recesses 1010A-1010C at proximal ends 1014A-1014C. According to various embodiments, the ridges or flanges 1008A-1008C may be designed to mate with the recesses 1010A-1010C such that parts of the sections 1002A-1002D overlap with one another and form an interlock that may prevent relative movement between the sections 1002A-1002C in at least one dimension (two dimensions in FIG. 10A). Section 1002A is shown having an open proximal end 1014A and section 1002C is shown having an open distal end 1012C. However, in other examples, proximal end 1014A and distal end 1012C may be closed ends.

Figure 10B:
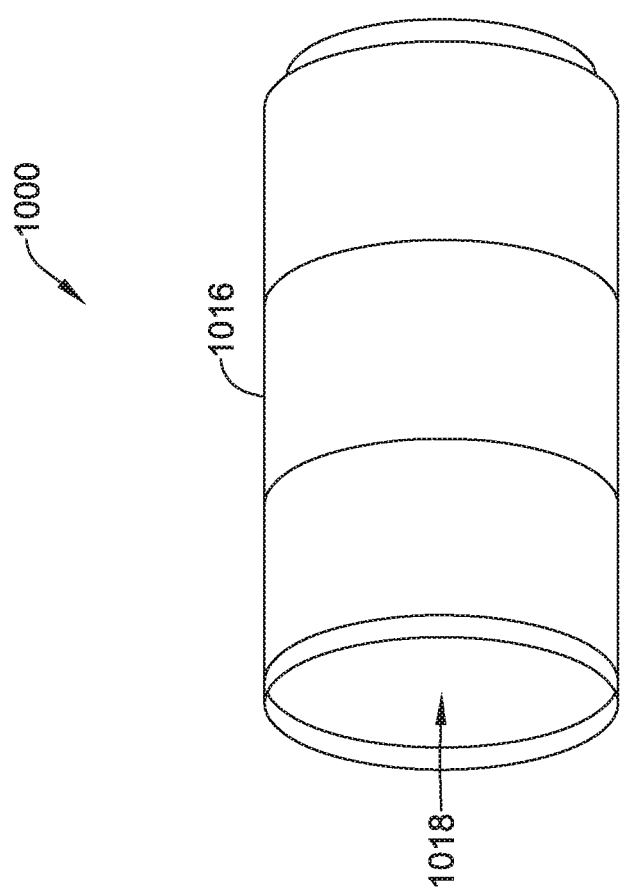
FIG. 10B is an illustrative but non-limiting example of the flux concentrator of FIG. 10A assembled in an end-to-end configuration.

Turning to FIG. 10B, the sections 1002A-1002C have been assembled or put together in an end-to-end configuration. That is, the flange or ridge 1008A of section 1002A has been placed in the recess 1010B of section 1002B and the flange or ridge 1008B of section 1002B has been place in the recess 1010C of section 1002C. Accordingly, the sections 1002A-1002C collectively form an elongated body 1016 that is substantially cylindrical shaped, and the sections 1002A-1002C are interlocked and prevented from moving relative to one another in two dimensions. The inner major surfaces 1006A-1006C define an internal cavity 1018. In some cases, the recesses 1010A-1010C receive the corresponding ridges or flanges 1008A-1008C, and fit together to provide a relatively contiguous cylinder of magnetically permeable material with little or no air gaps between sections 1002A-1002C.

Figure 10C:
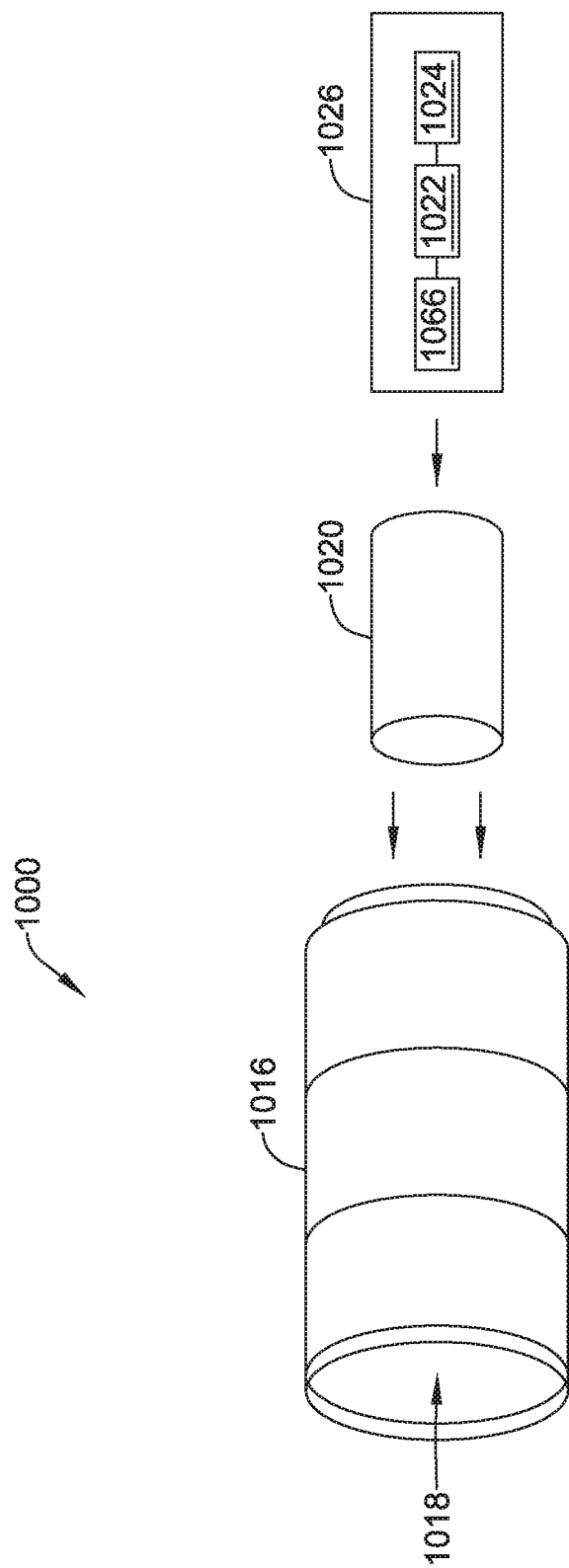
FIG. 10C is an illustrative but non-limiting example of the flux concentrator of FIG. 10B with a rechargeable power source and/or electronics inserted into an internal cavity of the flux concentrator.
Figure 10D:
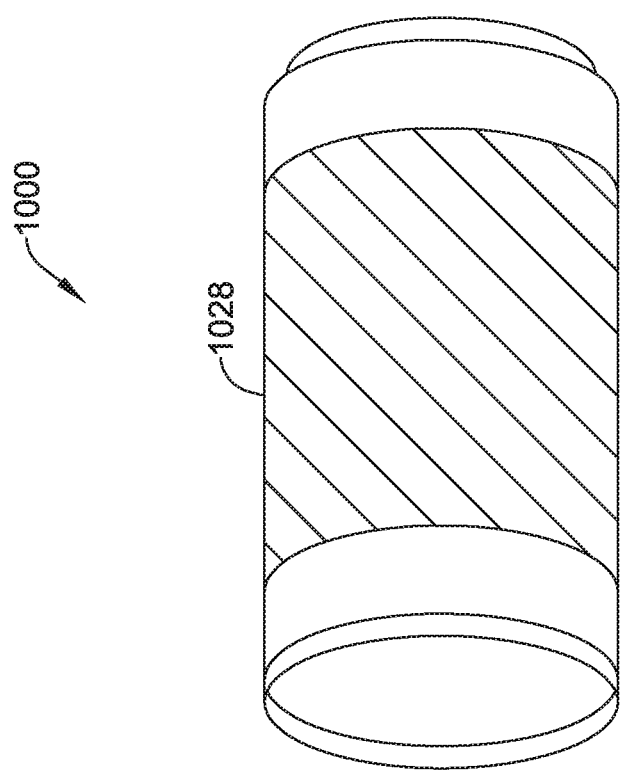
FIG. 10D is an illustrative but non-limiting example of the flux concentrator assembly of FIG. 10C with a conductive layer added.

Turning to FIG. 10C, a rechargeable power source 1020 and/or electronics 1026 may be inserted into the internal cavity 1018 formed by the sections 1002A-1002C. In this example, the electronics 1026 includes charging circuitry 1066, a controller 1022 and therapeutic circuity 1024. In other embodiments, the electronics 1026 may include any suitable circuitry, modules, elements, and/or components discussed herein and known in the art.

In some cases, rather than providing sections 1002A-1002C of magnetically permeable material as shown in FIG. 10C, or in addition to, it is contemplated that a magnetically permeable material may be deposited directly on the outer surface of the rechargeable power source 1020.

A coil may be positioned around sections 1002A-1002C. In one example, and turning to FIG. 10D, a conductive layer 1028 may be disposed on a portion of the elongated body 1016 formed by sections 1002A-1002C. In this case, the conductive layer 1028 may be a conductive layer disposed on the elongated body 1016 in any suitable manner, such as a printing technique, a spraying technique, a roll coating technique, an evaporation or deposition technique, or any suitable manner. Once the conductive layer 1028 has been disposed on the elongated body 1016, and as shown in FIG. 10E, the elongated body 1016, as well as the rechargeable power source 1020 and the electronics 1026, may be placed inside a non-ferromagnetic housing 1030. For example, the housing 1030 may be glass, stainless steel, ceramic or a polymeric material. The housing 1030 may be similar in function to the housing 120, 220, 512, and 904, described herein.

The housing 1030 in FIG. 10E is shown to have a substantially cylindrical profile, or a tubular form or shape and as discussed above, the elongated body 1016 may be shaped to conform to an inner surface of the housing 1030. Once inside, and in one example, the conductive layer 1028 may be etched through the housing using lasers or the like to form a receiving coil 1032 wrapped around the elongated body 1016. In some cases, the conductive layer 1028 may be etched before being placed inside the housing 1030. In any event, the receiving coil 1032 may be electrically connected to the electronics 1026 via feedthroughs, bond wires, or in any other suitable manner.

As discussed herein, the receiving coil of the IMD 10 may be set to a particular resonant frequency by adjusting the inductance L of the receiving coil 1032 and/or adjusting the capacitance C of the receiving coil. In some cases, the inductance L may be adjusted by adjusting the number of turns of the receiving coil 1032. In some cases, a receiving coil 1032 having a determined number of turns may be etched from the conductive layer 1028. In another example, the conductive layer 1028 may already be etched to produce the receiving coil 1032, but a conductor (not shown) may be added to short out or bypass selected turns of the receiving coil 1032, resulting in a desired number of effective turns. In another example, the conductive layer 1028 may be etched to produce the receiving coil 1032 but with several conductive fuses connecting selected turns of the receiving coil 1032. Selected ones of the fuses may be blown, such as with a laser or electrically, to increase the number of effective turns of the receiving coil 1032. In yet another example, the capacitance C may be adjusted to achieve a desired resonant frequency of the receiving coil 1032. In further examples, both the number of turns of the receiving coil 1032 and the capacitance may be adjusted to achieve a desired resonant frequency, when desired.

Figure 10F:
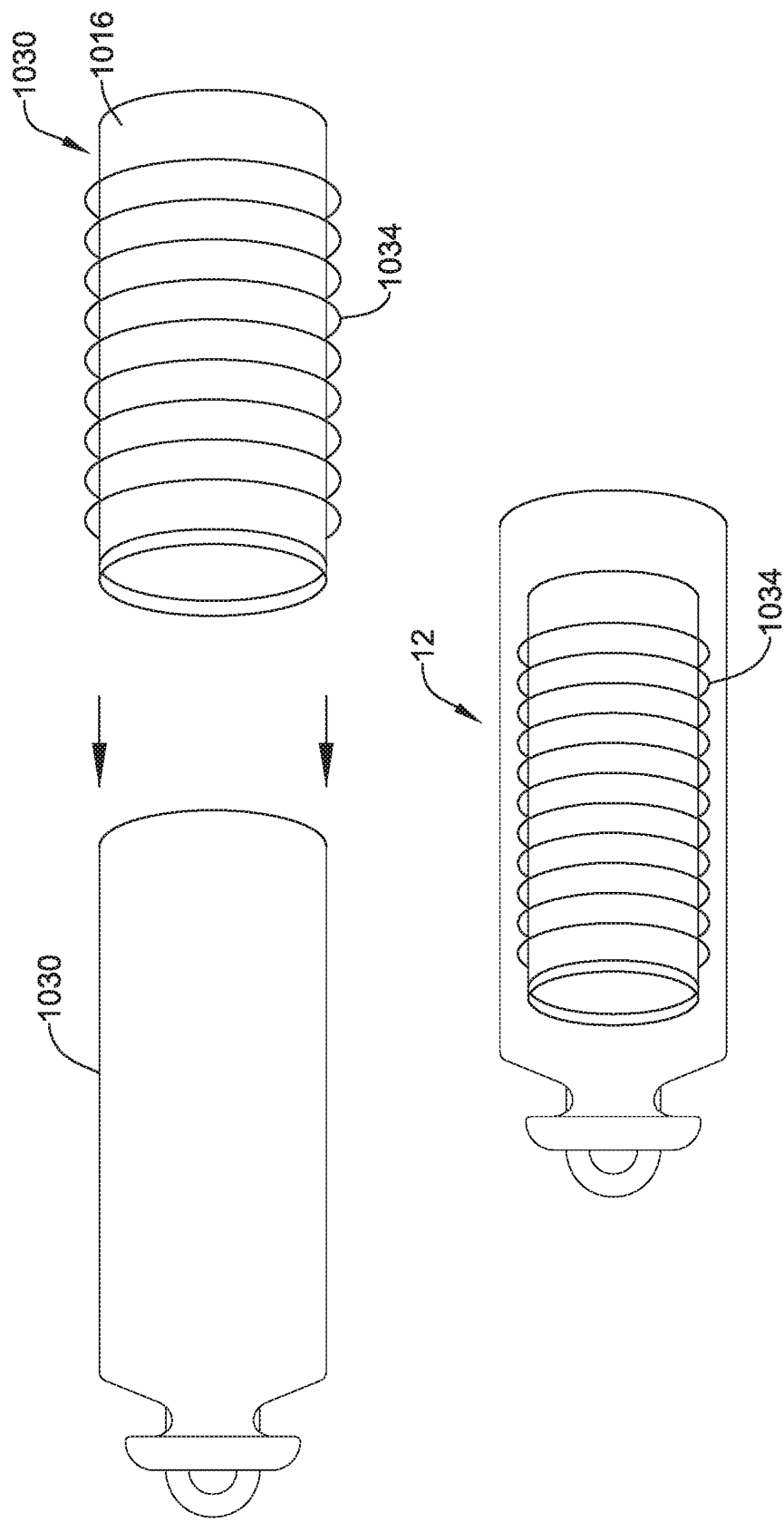
FIG. 10F is an illustrative but non-limiting example of the flux concentrator assembly of FIG. 10C with a receiving coil added and inserted into a non-ferromagnetic housing.

In another example, rather than depositing a conductive layer 1028 and the etching the layer to produce the receiving coil, a wire or the like may be wound, printed, sprayed, and/or otherwise disposed around at least a portion of the elongated body 1016, such as shown in FIG. 10F. In some cases, the rechargeable power source 1020 and/or the electronics 1026 may be placed inside the elongated body 1016, and the entire assembly may be placed inside of a non-ferromagnetic housing 1030. The housing 1030 may be, for example, glass, stainless steel, ceramic or a polymeric material. The housing 1030 may be similar in function to the housing 120, 220, 512, and 904, described herein.

Figure 10G:
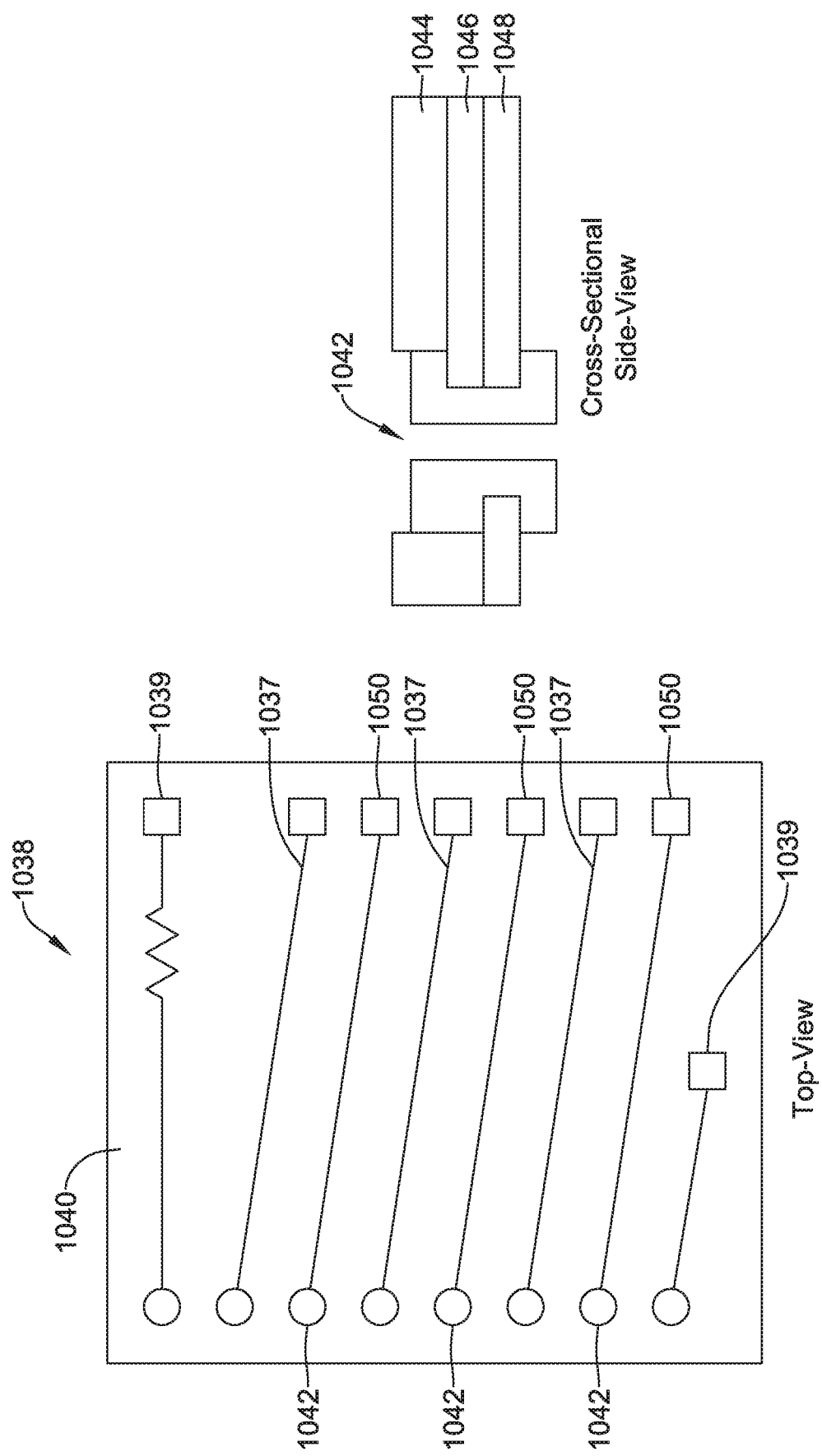
FIG. 10G is an illustrative but non-limiting example of a receiving coil formed on a flexible printed circuit board.
Figure 10H:
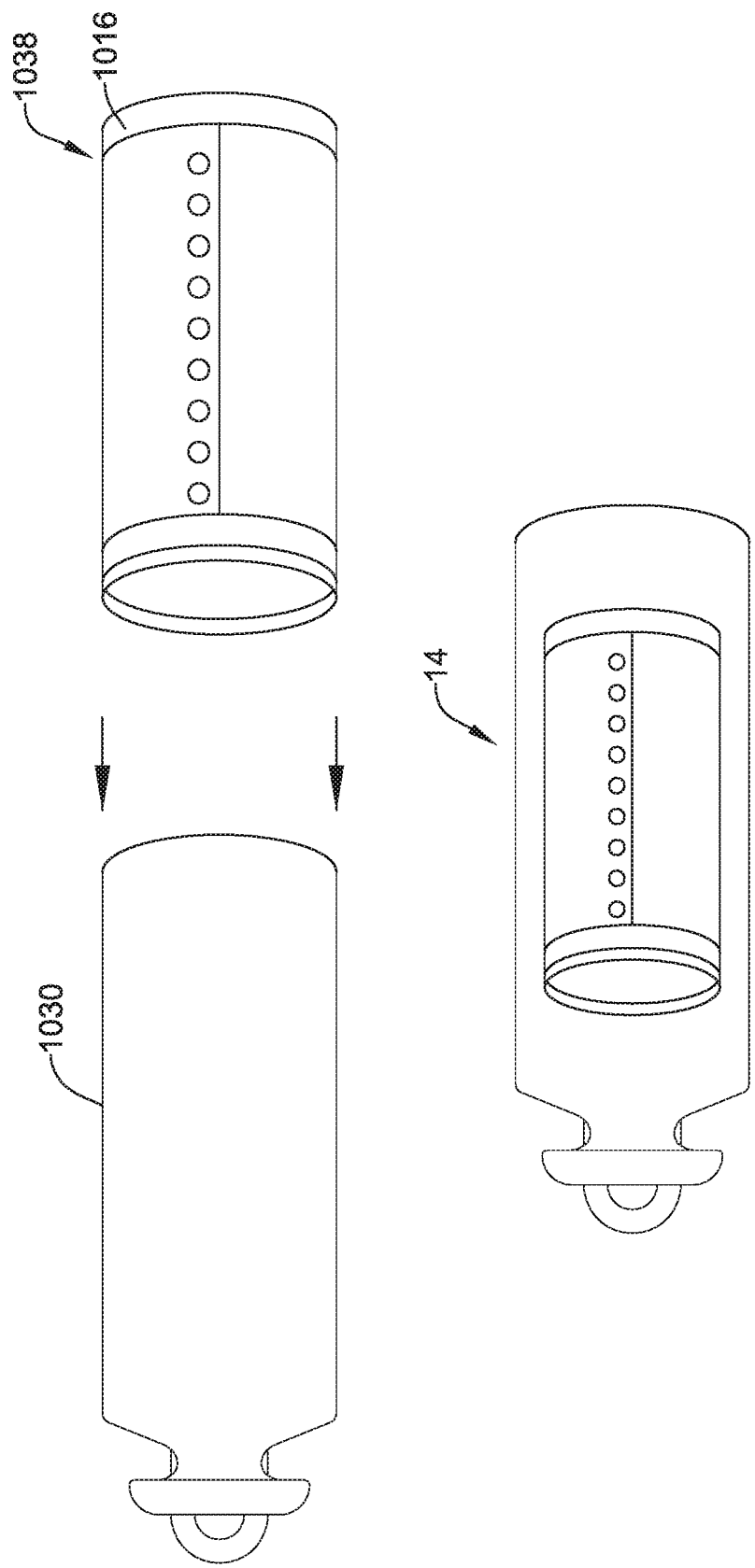
FIG. 10H is an illustrative but non-limiting example of the flux concentrator assembly of FIG. 10C with the receiving coil of FIG. 10G wrapped around and inserted into a non-ferromagnetic housing.

In yet another example, a receiving coil 1036 may be formed on a flexible printed circuit board (PCB) substrate 1040, such as shown in FIG. 10G. The resulting PCB coil structure 1038 may then be wrapped around a portion of the elongated body 1016, such as shown in FIG. 10H. FIG. 10G depicts a front-view and a cross-sectional side-view of an exemplary PCB coil structure 1038. The receiving coil 1036 may include capture pads 1050 and conductor traces printed, etched, deposited, and/or otherwise formed on the flexible substrate 1040 to form the PCB coil structure 1038. The size, shape, curvature, thickness, dimension, spacing, number of turns, spacing between turns, and the like may be set based on desired operating characteristics of the receiving coil 1036, such as the desired resonant frequency. The features of the receiving coil 1036 may be optimized using simulation and optimization tools to maximize the Q, minimize the resistance, and the like of the receiving coil 1036.

As shown in the cross-sectional side view of FIG. 10G, the PCB substrate 1040 may be multi-layered and may include a solder mask 1044, a patterned conductors 1046, and a flexible base material 1048. In other examples, the substrate 1040 may include more or fewer layers. In some cases, the solder mask 1044 may be a thin lacquer-like layer of polymer and may be applied to conductive traces of the patterned conductors 1046 for protection against oxidation and to prevent solder bridges from forming between closely spaced solder pads or conductive traces. The solder mask 1044 may come in different media depending upon the demands of the application. For example, the solder mask 1044 may be epoxy liquid that is provided on the patterned conductors 1046. The patterned conductors 1046 may include, for example, a wide variety of metal foils of varying thickness. For example, in some cases, copper foils may be used to serve as the patterned conductors 1046.

The base material 1048 may a flexible polymer film that provides the foundation for the PCB substrate 1040. In some cases, the base material 1048 may provide physical and electrical properties of the PCB coil structure 1038. There are a number of different materials that may be suitable for the base material 1048 including, but not limited to, polyester (PET), polyimide (PI), polyethylene naphthalate (PEN), polyetherimide (PEI), along with various fluropolymers (FEP) and copolymers. Polyimide films are most prevalent owing to their blend of advantageous electrical, mechanical, chemical and thermal properties.

As can be seen in FIG. 10G, an array of pads 1042 may be horizontally spaced from an array of capture pads 1050. The patterned conductors 1046 define individual coil windings 1037 that extend at an angle from each capture pad 1050 to a corresponding pad 1042. When the PCB substrate 1040 is rolled around the elongated body 1016, the pads 1042 align with the horizontally spaced capture pads 1050, where they are soldered together. This electrically connects the individual coil windings 1037 into a three dimensional coil structure forming the receiving coil of the IMD.

Feedthrough paths 1039 may be provided to connect the receiving coil 1036 to electronics 1026 placed inside the elongated body 1016. In some embodiments, the PCB coil structure 1038 may have any number of additional components attached to the PCB substrate 1040. For example, components such as capacitors, inductors, resistors, fuses, amplifiers, matching networks, etc., may share space on the PCB substrate 1040.

In some cases, the use of the PCB coil structure 1038 may lower the mechanical stress on the elongated body 1016 during the manufacture and assembly of the IMD. In some cases, ferromagnetic materials that are used to form sections 1002A-1002C of the elongated body 1016. These ferromagnetic materials can be rather brittle. When so provided, reducing the mechanical stress during manufacture and subsequent use of the IMD can increase the manufacturing yield, reliability and/or lifetime of the resulting IMD. In addition, the PCB coil structure 1038 discussed above may allow for more precise optimization of trace thickness, widths, and spacing for tuning the resonance frequency, peak frequency and/or DC resistance of the receiving coil.

In some cases, the PCB coil structure 1038 may be structured to be wound around the elongated body 1016 multiple turns, so that each individual coil windings 1037 of the PCB coil structure 1038 forms multiple windings around the elongated body. When so provided, it is contemplated that mechanical windows or vias (not shown) may be provided in the PCB coil structure 1038 to connect the array of pads 1042 to the corresponding array of capture pads 1050.

Once the PCB coil structure 1038 has been disposed on at least a portion of the elongated body 1016, the rechargeable power source 1020 and/or the electronics 1026 may be placed inside the elongated body 1016, and the entire assembly may be inserted into a non-ferromagnetic housing 1030, as best seen in FIG. 10H.

Figure 10I:
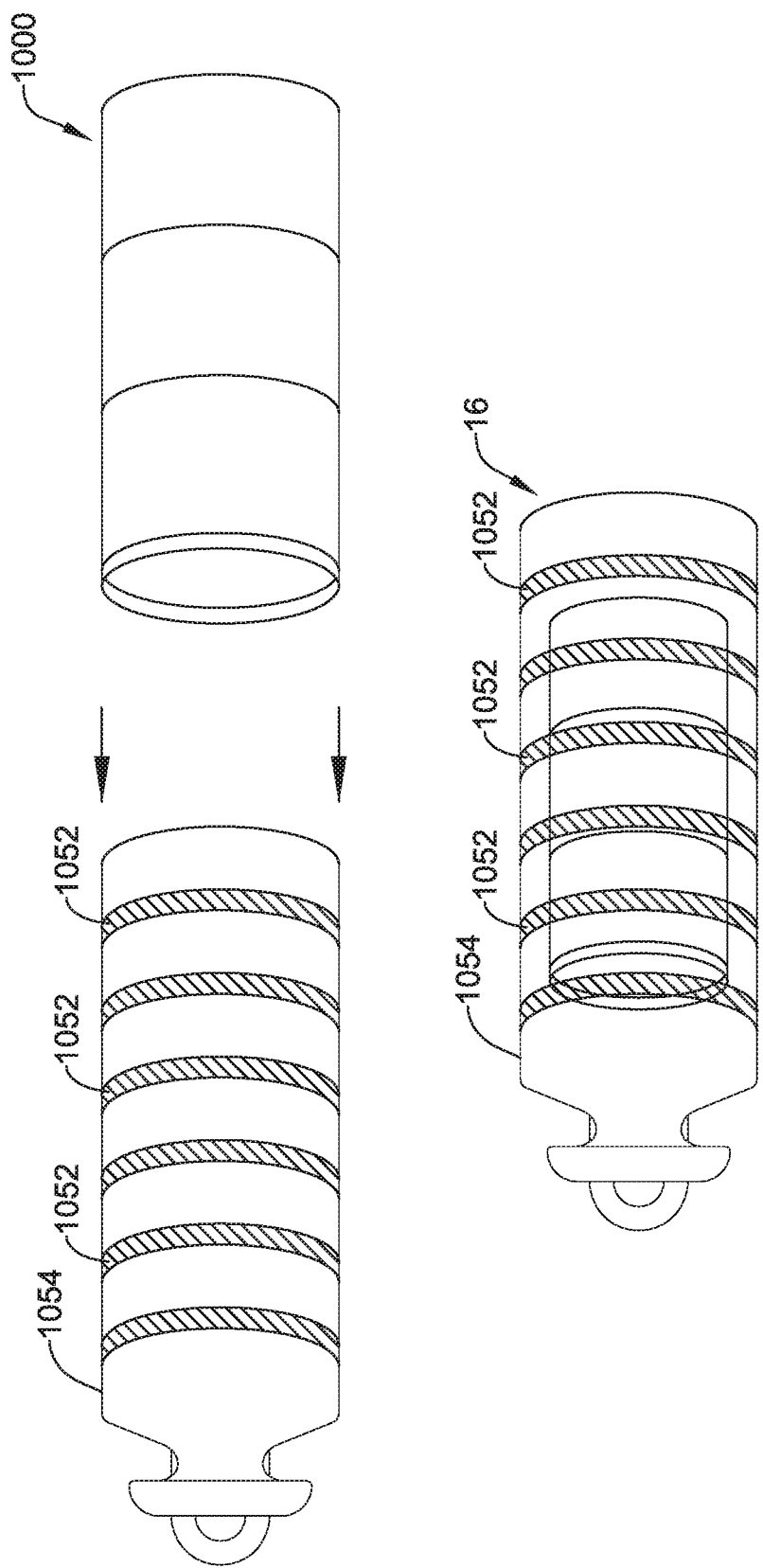
FIG. 10I is an illustrative but non-limiting example of the flux concentrator assembly of FIG. 10C inserted into a non-ferromagnetic housing with a receiving coil secured to, embedded in, or otherwise carried by the housing.

In some cases, the elongated body 1016 containing the rechargeable power source 1020 and/or the electronics 1026 may be placed inside a non-ferromagnetic housing 1054 without first providing a receiving coil around the elongated body 1016, as seen in FIG. 10I. When so provided, a receiving coil 1052 may be secured to, embedded in, or otherwise carried by the housing 1054. In some cases, the housing 1054 may include a double extruded silicone tubing with the receiving coil 1052 embedded between the extrusions. In some cases, the housing 1054 may be double dipped silicon with the receiving coil 1052 embedded in the silicon. In one example, the receiving coil 1052 may be dipped in silicon and the leads of the receiving coil 1052 may be extracted from the silicon. The receiving coil 1052 and silicon may then be dipped again. In some cases, the outside layer of silicone may have a higher durometer for rigidity and abrasion resistance. Similar to IMD's 10, 12, and 14, IMD 16 may be set to a particular or desired resonant frequency by adjusting the inductance of the receiving coil 1052, the capacitance, or both.

Figure 10J:
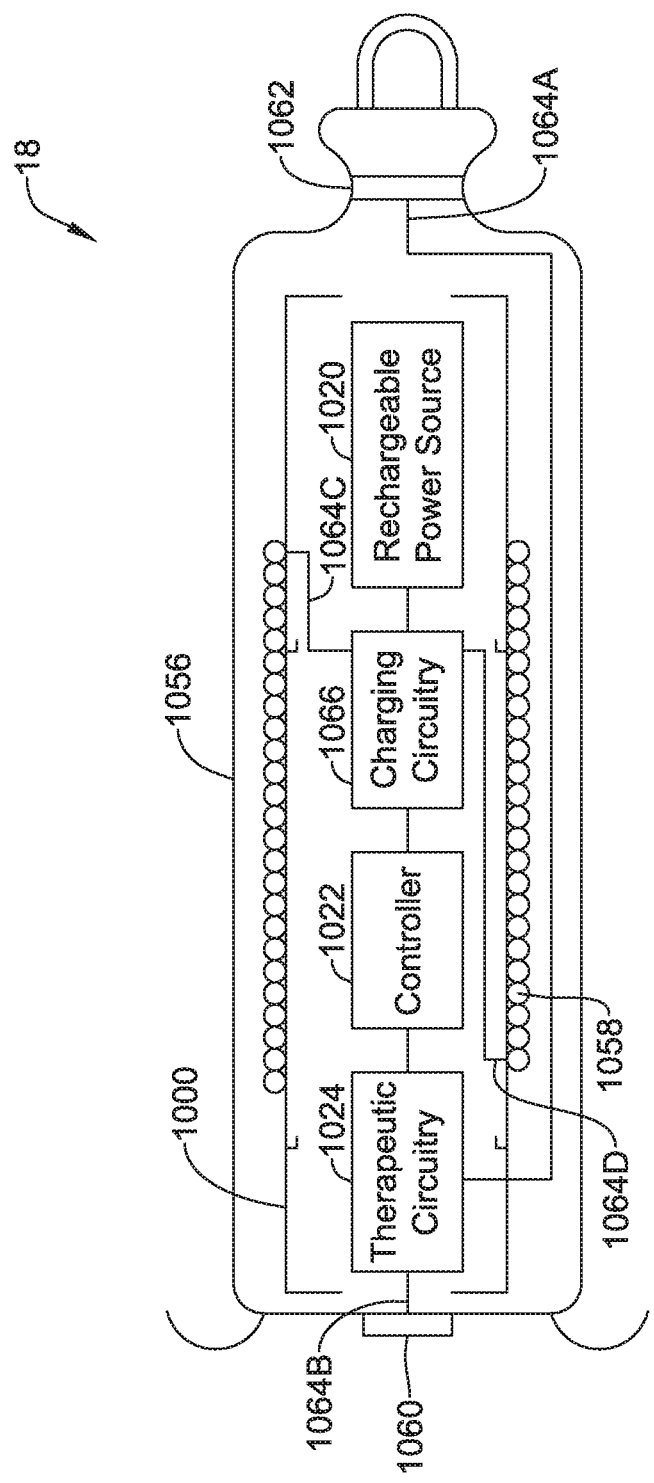
FIG. 10J is a schematic partial cross-sectional view of an illustrative IMD configured with the flux concentrator assembly of FIG. 10F.

FIG. 10J is a schematic view of an illustrative IMD 18 configured with the three sections 1002A-1002C of the flux concentrator 1000 of FIG. 10A. The configuration and operation of the IMD 18 and its components may be similar to the configuration and operation of the IMD 900 and its components described with respect to FIG. 9. According to various embodiments, the IMD 18 may be configured to be implanted within a patient such as the patient 600 (FIG. 6). The IMD 18 may be manufactured or assembled as described in, for example, FIGS. 10A-10I. In one specific case, the IMD 18 may be assembled according to FIGS. 10A-10E. When so provided, IMD 18 may include a housing 1056 similar to the housing 1030 and a receiving coil 1058 similar to the receiving coil 1032. In another example, the IMD 18 may be assembled according to FIGS. 10A-10C and FIG. 10F. When so provided, IMD 18 may include the housing 1056 similar to the housing 1030 and the receiving coil 1058 similar to the receiving coil 1034. In another example, the IMD 18 may be assembled according to FIGS. 10A-10C and FIGS. 10G-10H. When so provided, IMD 18 may include the housing 1056 similar to the housing 1030 and the receiving coil 1058 similar to the receiving coil 1036 on the PCB coil structure 1038. In another example, the IMD 18 may be assembled according to FIGS. 10A-10C and FIG. 10I. When so provided, IMD 18 may include the housing 1056 similar to the housing 1054 with the integrated receiving coil 1058 similar to the integrated receiving coil 1052.

According to various embodiments, the illustrative IMD 18 may also include electrodes 1060 and 1062 that may be exposed external to the housing 1056 and may be operably coupled to a therapeutic circuitry 1024 disposed within the housing 1056. The controller 1022 may include, for example, a processor, a state machine and/or other suitable circuitry. In some embodiments, one or more feedthroughs 1064A-1064B may extend from outside the housing 1056 to inside the housing 10560, and may electrically connect the electrodes 1060 and 1062 to the therapeutic circuitry 1024. Also, one or more feedthroughs 1064C-1064D may extend from outside the flux concentrator 1000 to inside the flux concentrator 1000 to connect the receiving coil 1058 to the charging circuitry 1066.

While two electrodes are illustrated, it will be appreciated that in some instances the IMD 18 may include three, four or more distinct electrodes. Depending on the intended functionality of the IMD 18, the electrodes 1060 and 1062 may be used for sensing and/or pacing the patient's heart. Alternatively, or in addition, the electrodes 1060 and 1062 may be used for communicating with other implanted devices and/or with external devices. In some cases, communication with other implanted devices may include conductive communication, but this is not required. Rechargeable power source 1020 may be disposed within the housing 1056 and may be configured to power the IMD 18, including the controller 1022. In some instances, the IMD 18 may be a leadless cardiac pacemaker (LCP), an implantable monitoring device or an implantable sensor.

In some cases, the charging circuitry 1066, the controller 1022 and the therapeutic circuitry 1024 may be located on distinct circuit boards or may be manifested within distinct integrated circuits (ICs). In some cases, the charging circuitry 1066 and the therapeutic circuitry 1024, while shown as distinct elements, may be combined within a single IC and/or on a single circuit board (e.g., the electronics 1026). In some cases, the therapeutic circuitry 1024 may be operatively coupled to the electrodes 1060 and 1062. In some instances, the therapeutic circuitry 1024 may be configured to sense one or more signals via the electrodes 1060 and 1062 (or additional electrodes) and/or to stimulate tissue via the electrodes 1060 and 1062. In some cases, the therapeutic circuitry 1024 may pace, or stimulate tissue, at least partly in response to the one or more sensed signals.

The flux concentrator 1000 forming the elongated body 1016, and the location, shape and orientation thereof, can be used to concentrate, confine, guide, steer, and/or focus externally generated magnetic fields through the receiving coil 1058 etched, wrapped, printed, and/or otherwise disposed around the elongated body 1016 or integrated within the housing 1056. In some cases, the permeability of the flux concentrator 1000 relative to the surrounding environment (e.g., relative permeability (pr) of greater than 10, 100, 1000, 10000, or more), may help concentrate the magnetic flux in the flux concentrator 1000, which passes through the receiving coil 1058. In some cases, the use of the flux concentrator 1000 may help improve inductive coupling between a transmitter coil (e.g. located outside of the body) and the receiving coil 1058 (e.g. located within the body), and thus may help improve the overall power transfer efficiency and/or total power transferred to the rechargeable power source 1020 and/or to increase the power efficiency of communication using the receiving coil 1058.

In certain embodiments, an external transmitter (e.g., transmitter 604, from FIG. 6) may inductively transfer power between about 10 kHz and 100 MHz within the patient's body to the receiving coil 1058 of the IMD 18. It is contemplated that the system may operate in the reactive, non-radiative, near-field (as in inductive charging system). In some cases, the external transmitter may transmit near-field energy such that the receiving coil 1058 of the IMD 18 may capture at least some of the near-field energy and provide it to the charging circuitry 1066. In various embodiments, the receiving coil 1058 may be configured to receive sufficient near-field energy from a wavelength band of near-field energy transmitted from outside the patient, and convert the received near-field energy into a form that may be used to recharge the rechargeable power source 1020 and/or to increase the power efficiency of communication. In various embodiments, the rate the rechargeable power source 1020 is charged may be at a rate faster than the rechargeable power source 1020 is depleted by powering the IMD 18 when the wavelength band of near-field energy is transmitted at an intensity that does not cause heat damage to the patient.

Figure 11A:
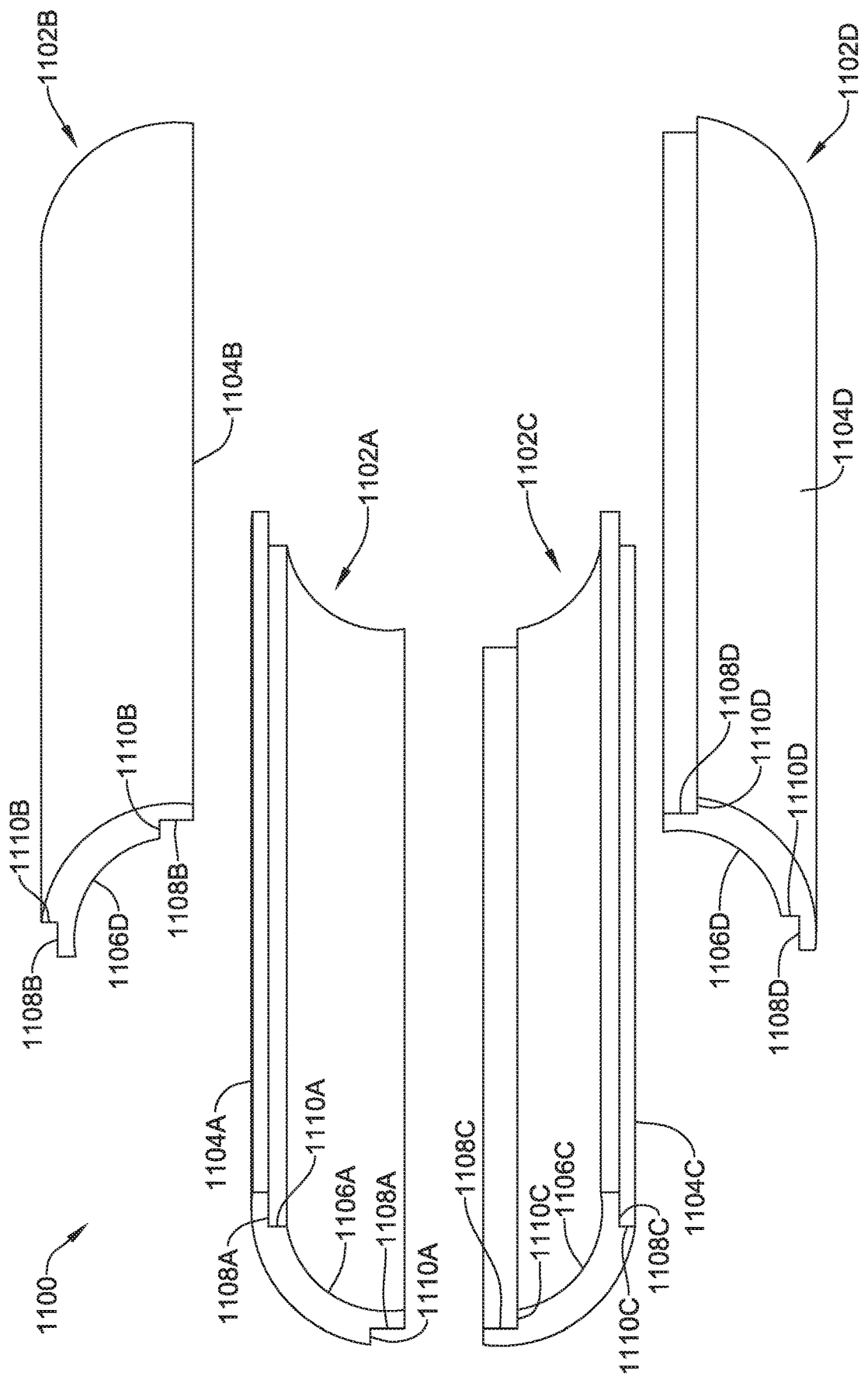
FIG. 11A is an exploded view of another illustrative but non-limiting example of a flux concentrator of an IMD.

FIGS. 11A-11I depict exemplary manufacturing/assembly of another IMD. FIG. 11A depicts an exploded-view of a flux concentrator 1100. As shown, there are four sections 1102A-1102D of the flux concentrator 1100. In other examples, more or fewer sections may be used. In some cases, the sections 1102A-1102D may each include a magnetically permeable material. In some cases, the magnetically permeable materials of each section 1102A-1102D may have a relative permeability ($\mu_r$) greater than 10. As shown, each section 1102A-1102D may have an outer major surface 1104A-1104D and an inner major surface 1106A-1106D. In this example, the sections 1102A-1102D are substantially arc shaped. However, in other embodiments, the sections 1102A-1102D may be any suitable shape such as square shaped or rectangular shaped, for example. Furthermore, the sections 1102A-1102D may be formed in a shape or form to conform to the shape of an inner surface of a housing (not shown in FIG. 11A). Each section 1102A-1102D may also have keyed portions that include, for example, ridges or flanges 1108A-1108D and recesses 1110A-1110D. Alternatively or additionally, each section 1102A-1102D may be bonded together. According to various embodiments, the ridges or flanges 1108A-1108D may be designed to mate with the recesses 1110A-1110C such that parts of the sections 1102A-1102D overlap with one another and form an interlock that may prevent relative movement between the sections 1102A-1102D in at least one or more dimensions. In the example shown in FIG. 11A, the sections 1102A-1102D overlap with one another and form an interlock that prevents relative movement between the sections 1102A-1102D in two dimensions.

Figure 11B:
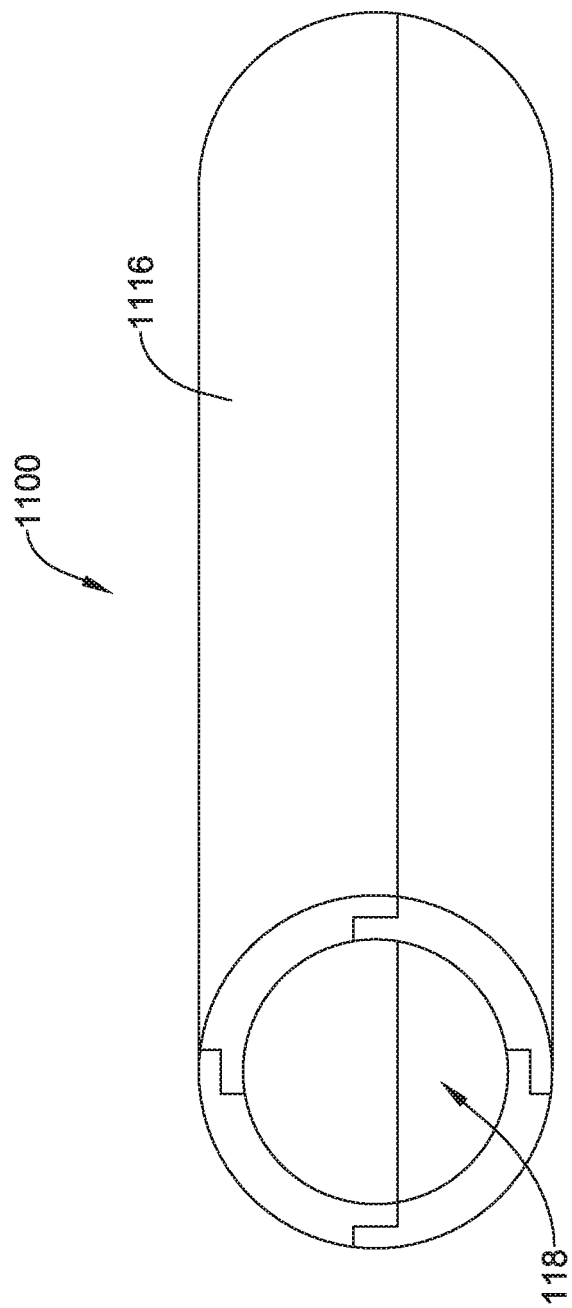
FIG. 11B is an illustrative but non-limiting example of the flux concentrator of FIG. 11A in an assembled configuration.

Turning to FIG. 11B, the sections 1102A-1102D have been assembled or put together in a circumferential configuration. That is, the ridges or flanges 1108A of section 1102A have been placed in the recess 1110B of section 1102B and the recess 1110C of section 1102C, the ridges or flanges 1108B of section 1102B have been placed in the recess 1110A of section 1102A and the recess 1110D of section 1102D, the ridges or flanges 1108C of section 1102C have been placed in the recess 1110A of section 1102A and in the recess 1110D of section 1102D, and the ridges or flanges 1108D of section 1102D have been placed in the recess 1110B of section 1102B and in the recess 1110C of section 1102C. Accordingly, the sections 1102A-1102D collectively form an elongated body 1116 that is substantially cylindrical shaped, with the sections 1102A-1102D interlocked and prevented from moving relative to one another in at least one dimension. The inner major surfaces 1106A-1106D of the sections 1102A-1102D define an internal cavity 1118.

Figure 11C:
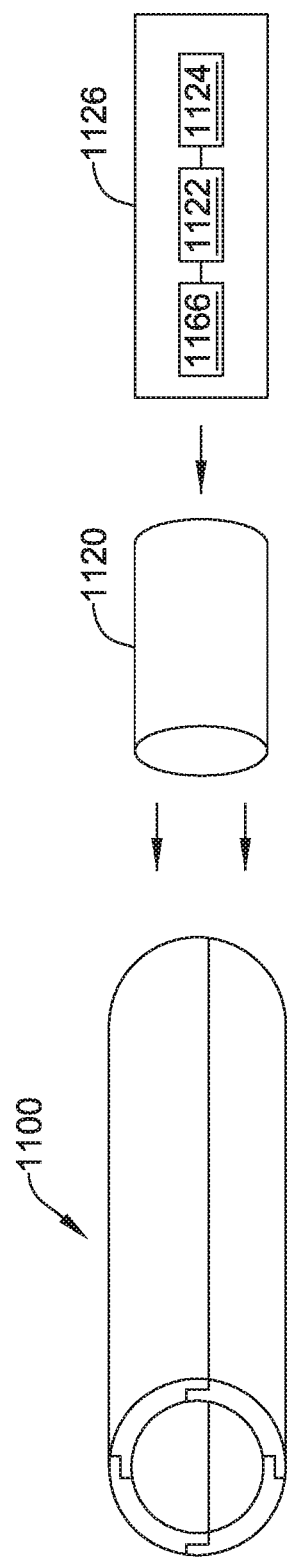
FIG. 11C is an illustrative but non-limiting example of the flux concentrator of FIG. 11B with a rechargeable power source and/or electronics inserted into an internal cavity of the flux concentrator.

In some cases, a rechargeable power source 1120 and/or operational circuitry 1126 may be inserted at least partially into the cavity 1118, as shown in FIG. 11C. In this example, the operational circuitry 1126 includes charging circuitry 1166, communication circuitry 1122 and therapeutic circuity 1124 are inserted into the cavity 1118. In other embodiments, the operational circuitry 1126 may include any suitable circuitry, modules, elements, and/or components.

Figure 11D:
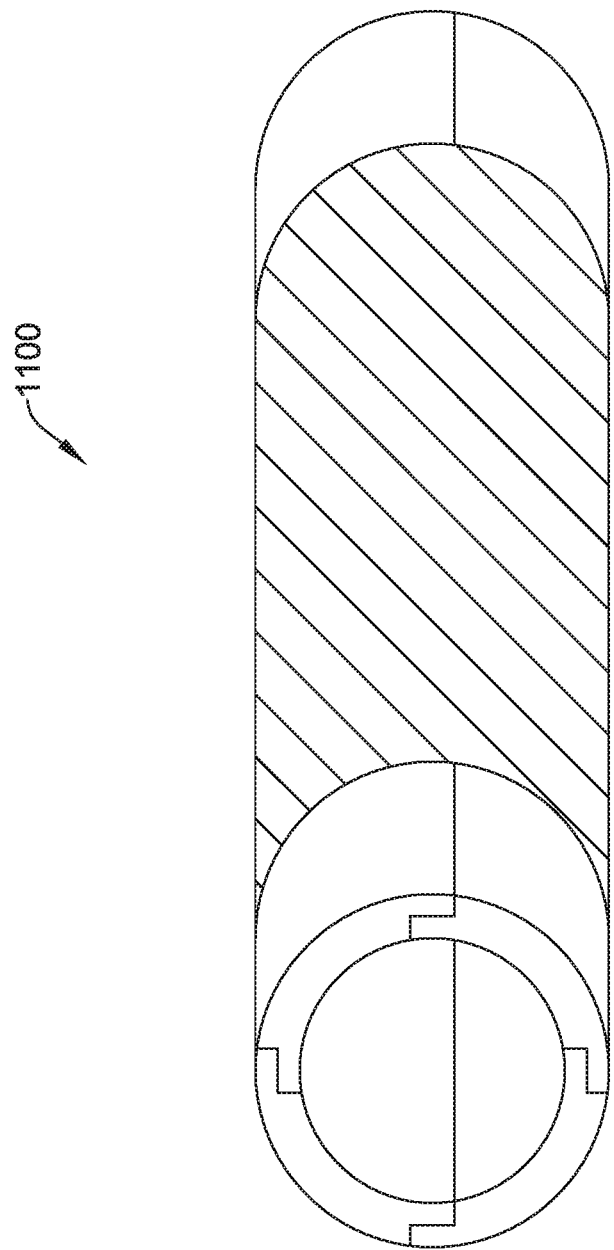
FIG. 11D is an illustrative but non-limiting example of the flux concentrator assembly of FIG. 11C with a conductive layer added.
Figure 11F:
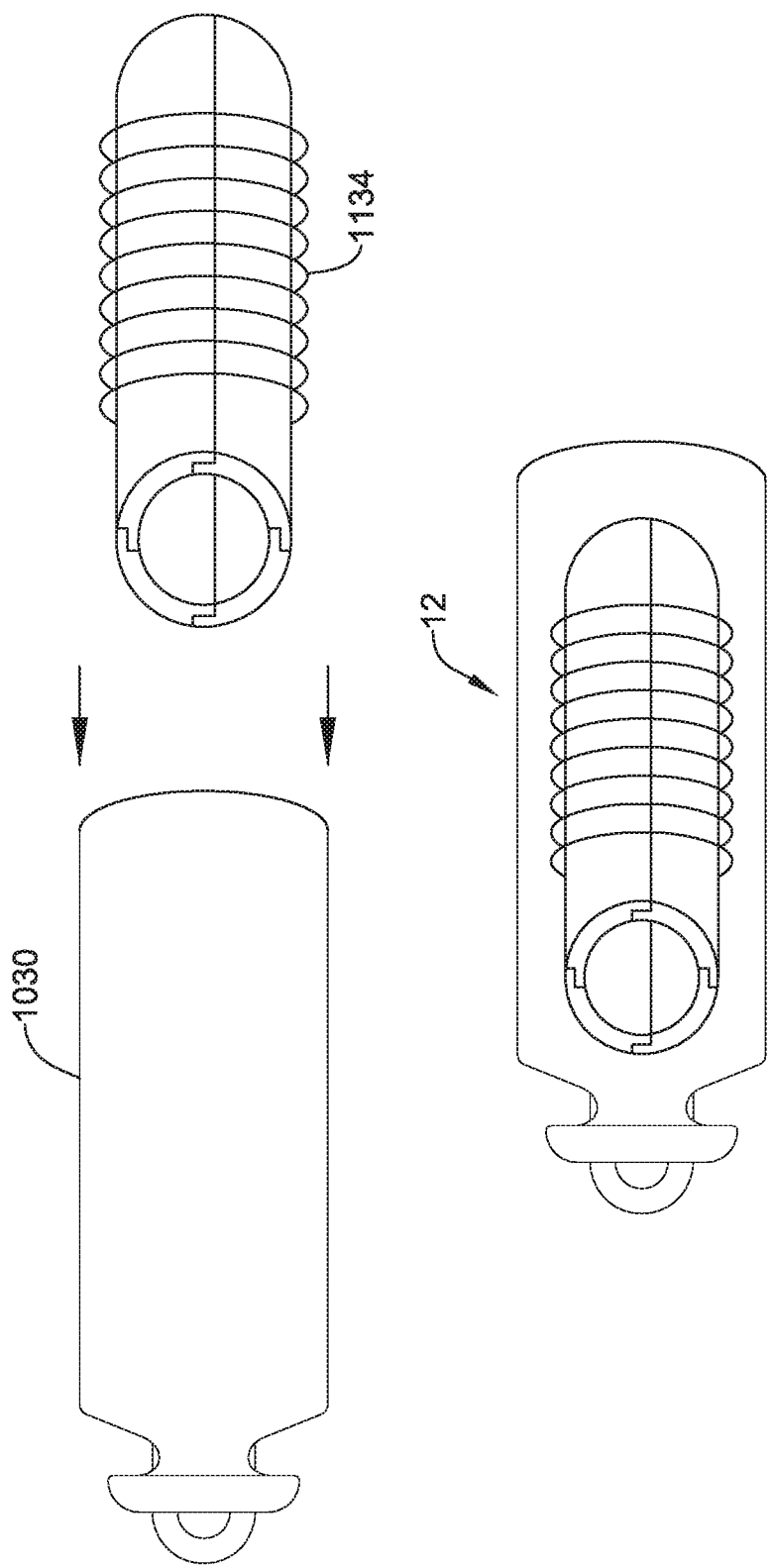
FIG. 11F is an illustrative but non-limiting example of the flux concentrator assembly of FIG. 11C with a receiving coil added and inserted into a non-ferromagnetic housing.
Figure 11G:
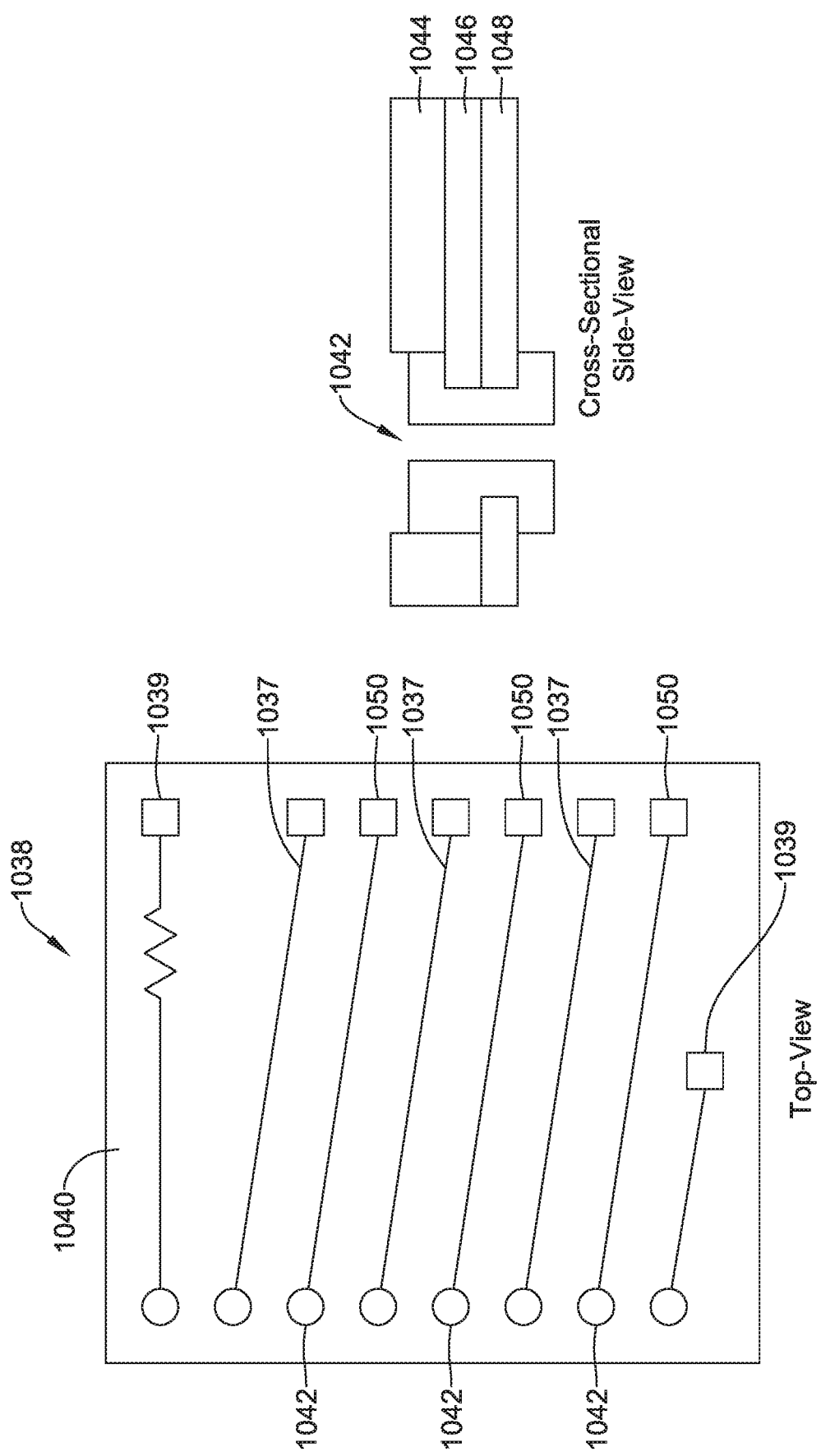
FIG. 11G is an illustrative but non-limiting example of a receiving coil formed on a flexible printed circuit board.
Figure 11H:
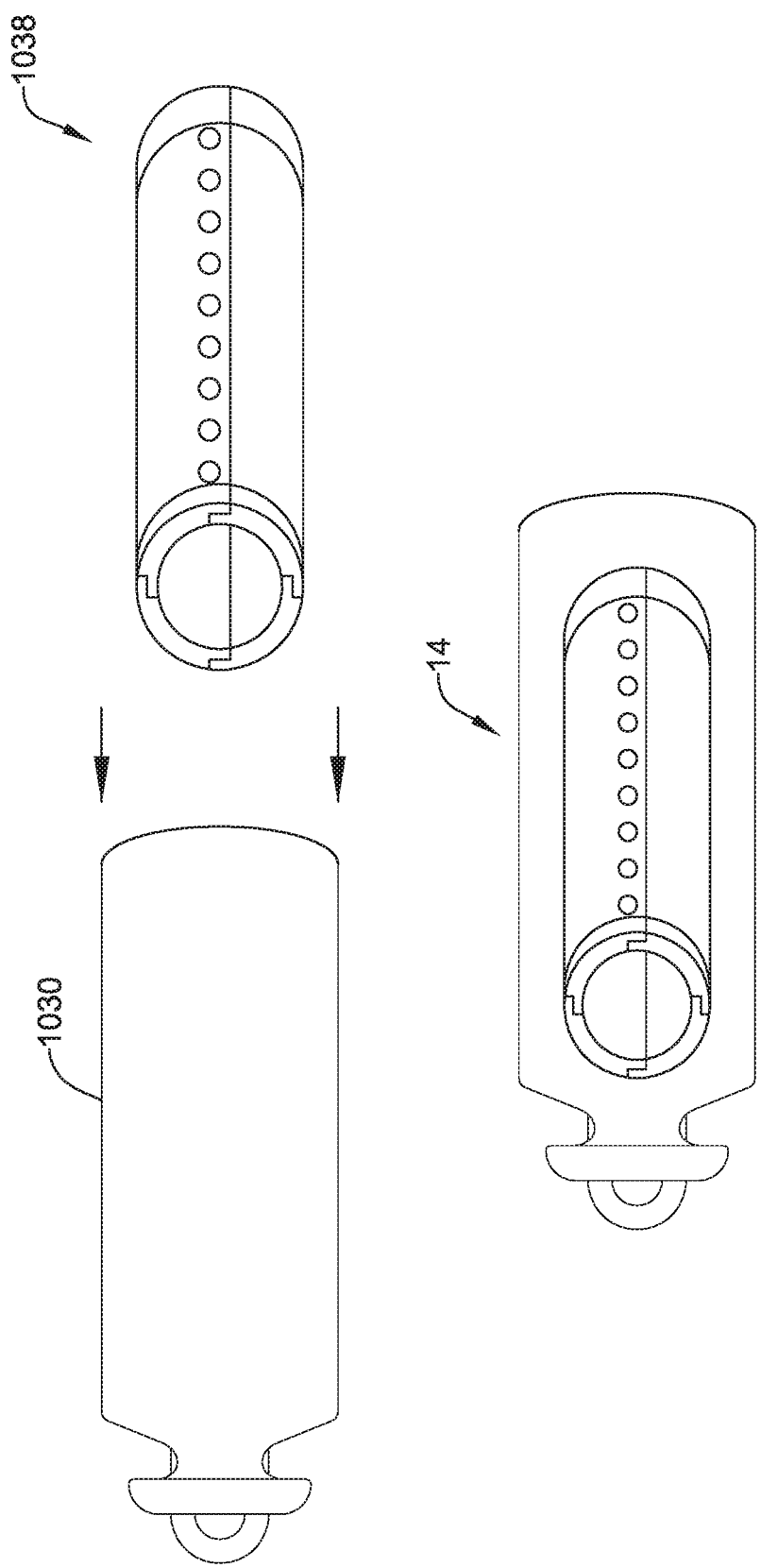
FIG. 11H is an illustrative but non-limiting example of the flux concentrator assembly of FIG. 11C with the receiving coil of FIG. 11G wrapped around and inserted into a non-ferromagnetic housing.
Figure 11I:
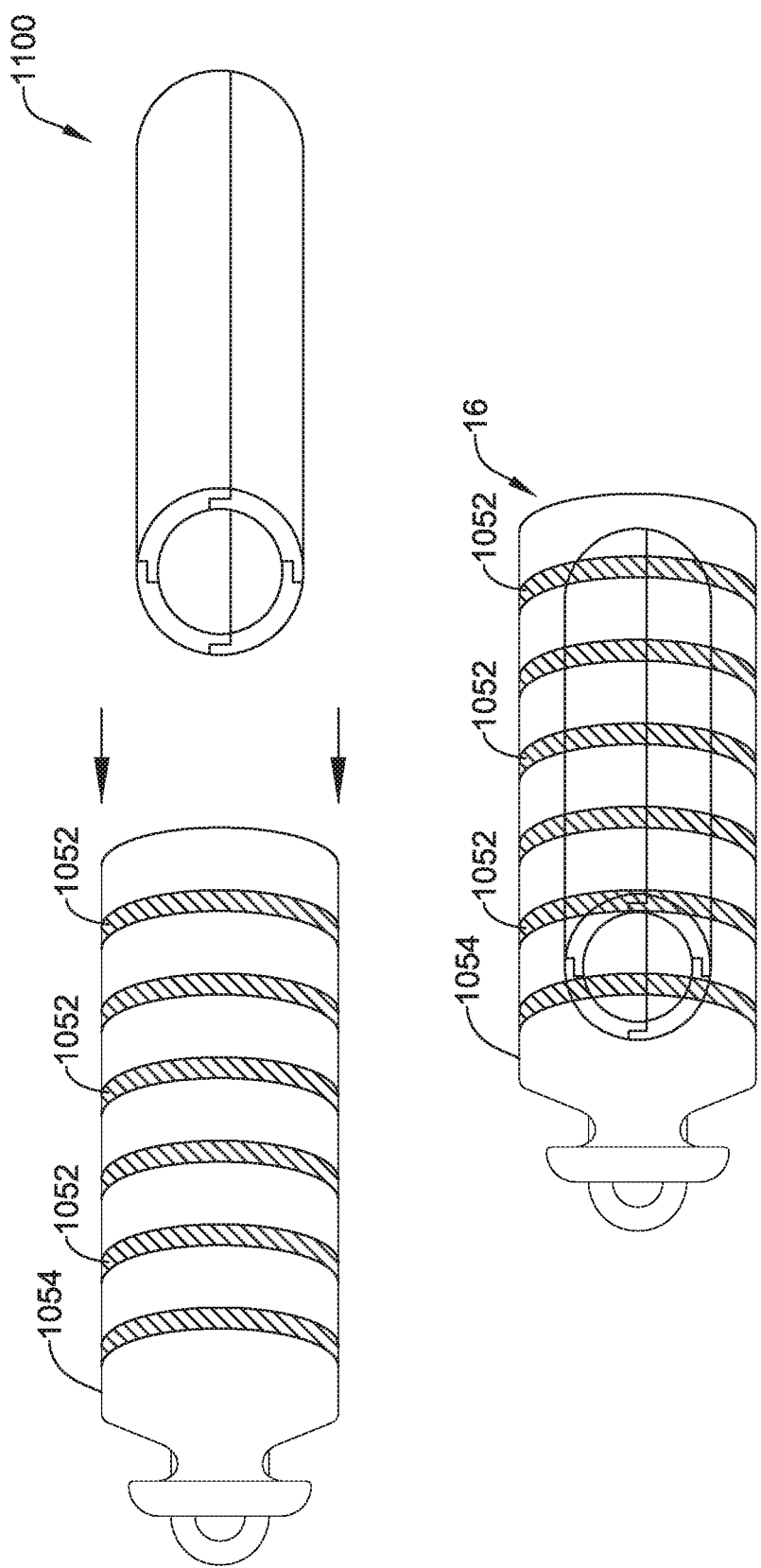
FIG. 11I is an illustrative but non-limiting example of the flux concentrator assembly of FIG. 11C inserted into a non-ferromagnetic housing with a receiving coil secured to, embedded in, or otherwise carried by the housing.

FIGS. 11D-11I depict the flux concentrator 1100 forming the elongated body 1116 configured with exemplary receiving coils and placed in housings. FIGS. 11D-1E depict the conductive layer 1028 being disposed on a portion of the elongated body 1116. The flux concentrator 1100 may then be disposed in the housing 1030 and the receiving coil 1032 may be etched from the conductive layer 1028 through the housing 1030, similar to FIGS. 10D-10E. FIG. 11F depicts the receiving coil 1034 wound, printed, sprayed, or disposed on the portion of the elongated body 1116, and placed in the housing 1030, similar to FIG. 10F. FIGS. 11G-11H depicts the receiving coil 1036 being disposed on the PCB substrate 1040 to create the PCB coil structure 1038, the PCB coil structure 1038 may then be disposed on the portion of the elongated body 1116, and then the assembly may be placed in the housing 1030, similar to FIGS. 10G-10H. FIG. 11I depicts the receiving coil 1052 being secured to, embedded in, or otherwise carried by the housing 1054, similar to FIG. 10I.

Figure 11J:
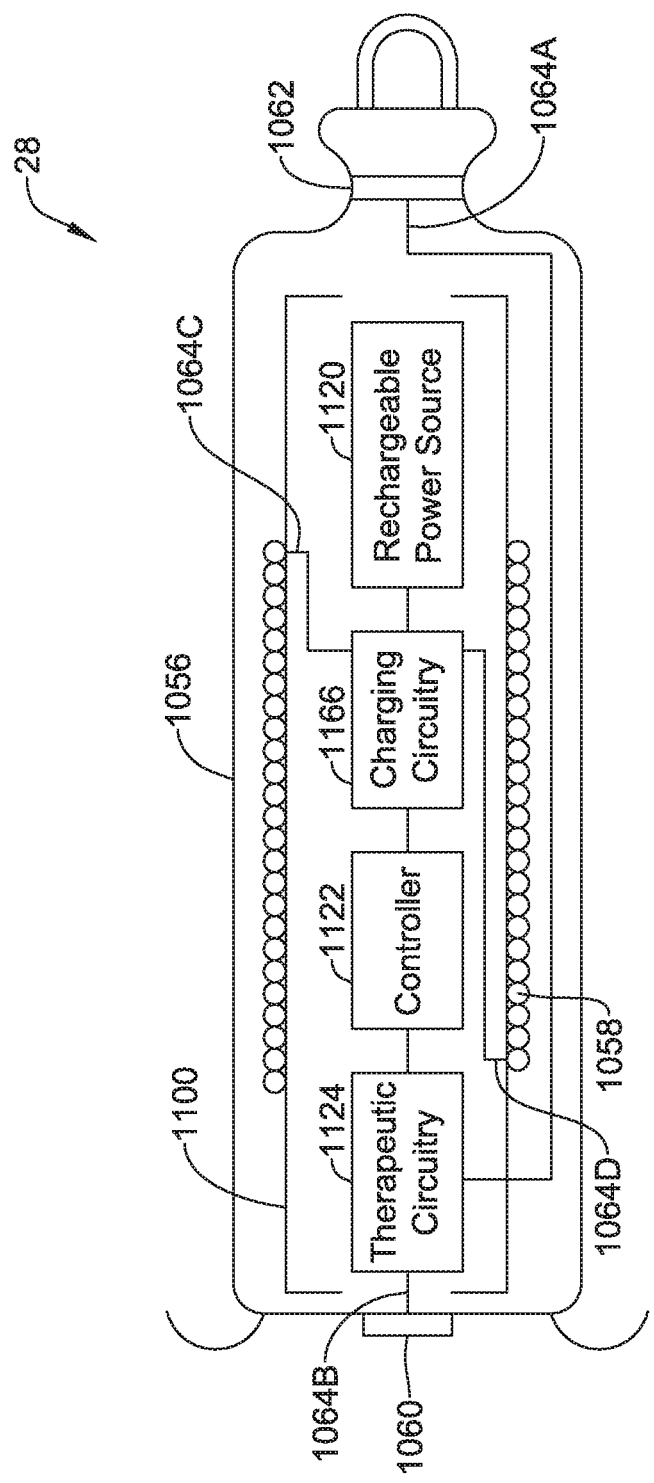
FIG. 11J is a schematic partial cross-sectional view of an illustrative IMD configured with the flux concentrator assembly of FIG. 11F.

FIG. 11J provides a schematic view of an illustrative IMD 28 configured with the four sections 1102A-1102D of the flux concentrator 1100. The configuration and operation of the IMD 28 and its components may be similar to the configuration and operation of the IMD 900 and its components described with respect to FIG. 9 and the configuration and operation of the IMD 18 and its components described with respect to FIG. 10J. According to various embodiments, the IMD 28 may be configured to be implanted within a patient such as the patient 600 (FIG. 6). The IMD 28 may be manufactured or assembled according to FIGS. 11A-11I. For example, the IMD 28 may be assembled according to FIGS. 11A-11E. When so provided, IMD 28 may include the housing 1056 similar to the housing 1030 and the receiving coil 1058 similar to the receiving coil 1032. In another example, the IMD 28 may be assembled according to FIGS. 11A-1C and FIG. 11F. When so provided, IMD 28 may include the housing 1056 similar to the housing 1030 and the receiving coil 1058 similar to the receiving coil 1034. In another example, the IMD 28 may be assembled according to FIGS. 11A-1C and FIGS. 11G-11H. When so provided, the IMD 28 may include the housing 1056 similar to the housing 1030 and the receiving coil 1058 similar to the receiving coil 1036 on the PCB coil structure 1038. In another example, the IMD 28 may be assembled according to FIGS. 11A-11C and FIG. 11I. When so provided, IMD 28 may include the housing 1056 similar to the housing 1054 with the integrated receiving coil 1058 similar to the integrated receiving coil 1052.

In some cases, as seen in FIG. 11J, the IMD 28 may include the communication circuitry 1122. In certain embodiments, the communication circuitry 1122 may be operatively coupled to the receiving coil 1058 and may provide a communication pathway to transmit messages to an external receiver (not shown) devices such as sensors, other medical devices, and/or the like, that are located externally to the IMD 28. Such devices may be located either external or internal to the patient's body. Irrespective of the location, external devices (i.e. external to the IMD 28 but not necessarily external to the patient's body) can communicate with the IMD 28 via communication circuitry 1122 to accomplish one or more desired functions. The communication circuitry 1122 may be configured to use one or more methods for communicating with the external receiver. For example, the communication circuitry 1122 may communicate via radiofrequency (RF) signals, inductive coupling, optical signals, acoustic signals, conducted communication signals, and/or any other signals suitable for communication.

In some cases, electrodes 1060 and 1062 may be exposed external to the housing 1056 and may be operably coupled to communication circuitry 1122 disposed within the housing 1056. In some cases, the communication circuitry 1122 may be configured to communicate with one or more external devices (e.g. the external receiver) using conducted communication via electrodes 1060 and 1062. Alternatively, or in addition, the communication circuitry 1122 of IMD 28 may be configured to communicate with one or more external devices (e.g. the external receiver) using inductive communication via the receiving coil 1058.

In some cases, the IMD 28 may communicate information, such as sensed electrical signals, data, instructions, messages, R-wave detection markers, etc., to the external receiver through the communication circuitry 1122. The IMD 28 may additionally receive information such as signals, data, instructions and/or messages from the external receiver through the communication circuitry 1122, and the IMD 28 may use the received signals, data, instructions and/or messages to perform various functions, such as charging the rechargeable power source 1120, storing received data, and/or performing any other suitable function.

In some cases, the communication circuitry 1122 may establish a communication pathway between the IMD 28 and the external receiver using an inductive mode of communication that utilizes near-field energy. Near-Field communication is a wireless form of short range communication using near-field magnetic flux for data transmission. For example, in some embodiments, an inductive communication link may be provided when the external receiver is not being utilized for transmission of electrical energy to recharge the rechargeable power source 1120 of the IMD 28. For instance, the communication circuitry 1122 may be configured to send an alert to the external receiver when the rechargeable power source 1120 is currently at a half-charged state or below. In this case, the communication circuitry 1122 may drive a communication signal (e.g., an AC signal) onto the coil 1058 to indicate the rechargeable power source 1120 is at or below the half-charged state. The communication signal may then create an oscillating magnetic field that may pass through the external receiver coil and induce an EMF. The EMF may then create an AC signal in the external receiver and the external receiver may decipher the AC signal. In certain embodiments, the external receiver may include a user-interface (not shown) with illuminating devises such as LED's, or audio devices, such as speakers, to display or issue a human perceptible alert in response to deciphering the AC signal. For example, the LED may be illuminated and/or the speakers may release a "buzz" sound indicating that the IMD 28 is at or below the half-charged state. The patient may observe the illumination of the LED and/or hear the "buzz" from the speakers and use the external receiver to transmit electrical energy to recharge the rechargeable power of source 1120 of the IMD 28. In some cases, the external receiver may send a message to the patient's mobile phone or other device to alert the patient.

In certain embodiments, the rechargeable power source 1120 may comprise only a primary (non-rechargeable) battery (e.g., FeS$_2$). In this case, the receiving coil 1058 may be configured to establish an inductive communication link with the external receiver or another external device (e.g., the patient's mobile phone, a network communication device, database, etc.).

In another embodiment, the inductive communication link may be provided when the external receiver is being utilized for transmission of electrical energy to recharge the rechargeable power source 1120 of the IMD 28. In this case, the external transmitter may generate an alternating current (AC) and create an oscillating magnetic field via a coil. The magnetic field may pass through the receiving coil 1058 of the IMD 28 and induce an EMF, which creates an AC signal in the IMD 28. The communication circuitry 1122 may be configured to send an alert to the external receiver when the external receiver is deemed to be misaligned with the IMD 28. For example, in some cases, misalignment of the external receiver with the IMD 28 may cause the IMD 28 to not charge sufficiently when the magnetic field is applied and charging is expected. The communication circuitry 1122 may drive a communication signal onto the receiving coil 1058 by modulating a transfer energy parameter (e.g., the amplitude, frequency, phase, pulse width, etc.) of the magnetic field. The modulated magnetic field may then pass back through the external receiver coil and induce an EMF, which creates an AC signal in the external receiver. The external receiver may then decipher the AC signal. The LED may be illuminated and/or the speakers may release a "buzz" sound in response to deciphering the AC signal. The patient may observe the illumination of the LED and/or hear the "buzz" from the speakers and realign the external receiver until the LED is no longer illuminated and/or the speakers stop releasing the "buzz" sound. In some cases, the external receiver may send a message to the patient's mobile phone or other device to alert the patient.

Figure 12A:
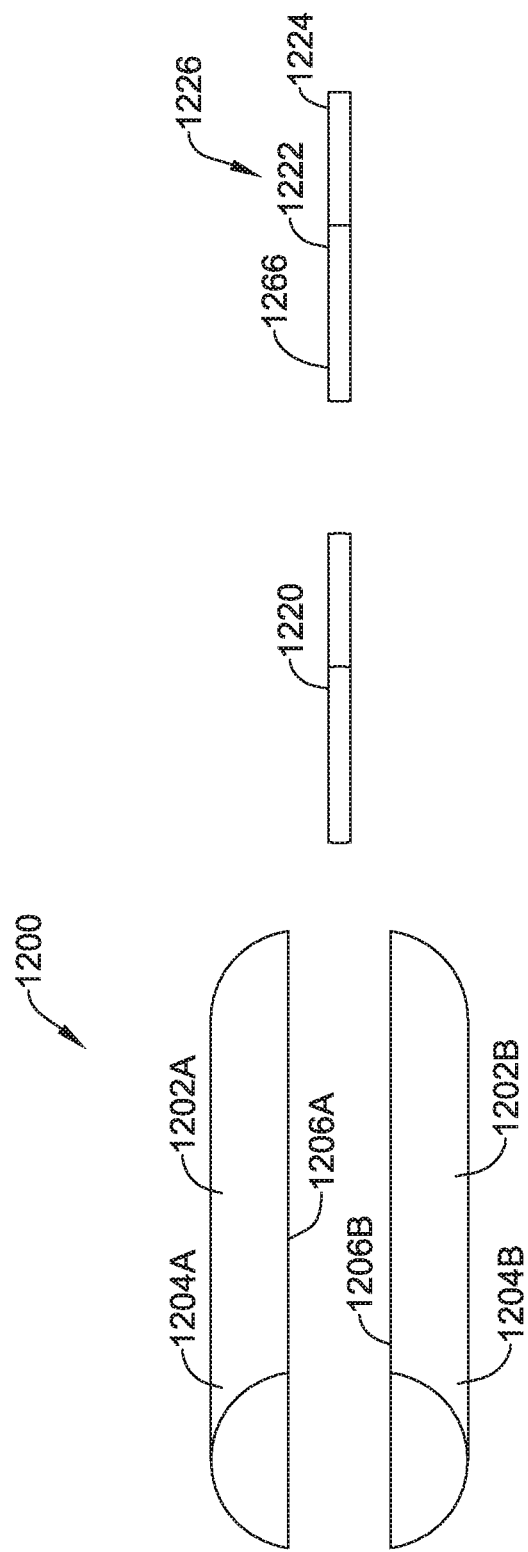
FIG. 12A is an exploded view of another illustrative but non-limiting example of a portion of an IMD that includes a flux concentrator that has flux concentrator sections with a rechargeable power source and/or electronics inserted between the flux concentrator sections.

FIGS. 12A-12H depict exemplary manufacturing/assembly processes of yet another IMD. FIG. 12A depicts an exploded-view of a flux concentrator 1200, a rechargeable power source 1220, and electronics 1226. In this example, there are two section 1202A-1202B of the flux concentrator 1200. In other examples, more or fewer sections may be used. In some cases, the sections 1202A-1202B may each include a magnetically permeable material. Moreover, the magnetically permeable material of each section 1202A-1102B may have a relative permeability ($\mu_r$) greater than 10. As shown, each section 1202A-1202B has a rounded surface portion 1204A-1204B and a straight or flat surface portion 1206A-1206B. However, in other embodiments, the sections 1202A-1202B may be any suitable shape such as square shaped, rectangular shaped, circular shaped, or cylindrical shaped, for example. In some cases, the sections 1202A-1202B may be formed in a shape that conforms to the shape of an inner surface of a housing (not shown in FIG. 12A) to as to increase the volume of the magnetically permeable material within the confines of the housing. It is also contemplated that the surface portions 1206A-1206B may be shaped to confirm to the shape of electronics 1226. For example, electronics 1226 may include a circuit board with one or more electrical components mounted to the circuit board. Each of the electrical components may have a different side/shape, and may extend away from the circuit board by differing distances. Thus, the electronics 1226 may present a non-planar surface that includes a number of projections. It is contemplated that the surface portions 1206A-1206B of sections 1202A-1202B may be shaped to accept at least some of the projections. In some cases, the surface portions 1206A-1206B of sections 1202A-1202B may be molded to match the non-planar surface of the electronics 1226 to increase the volume of the magnetically permeable material within the confines of the housing.

In some cases, each section 1202A-1202B may also have keyed portions (not shown) that include ridges or flanges and recesses. According to various embodiments, the ridges or flanges may be designed to mate with the recesses such that parts of the sections overlap with one another and form an interlock that may prevent relative movement between the sections in at least one or more dimensions. In some cases, such ridges or flanges and recesses may mate with one another beyond a perimeter of the electronics 1226. Alternatively or additionally, each section 1202A-1202B may be bonded together.

Figure 12B:
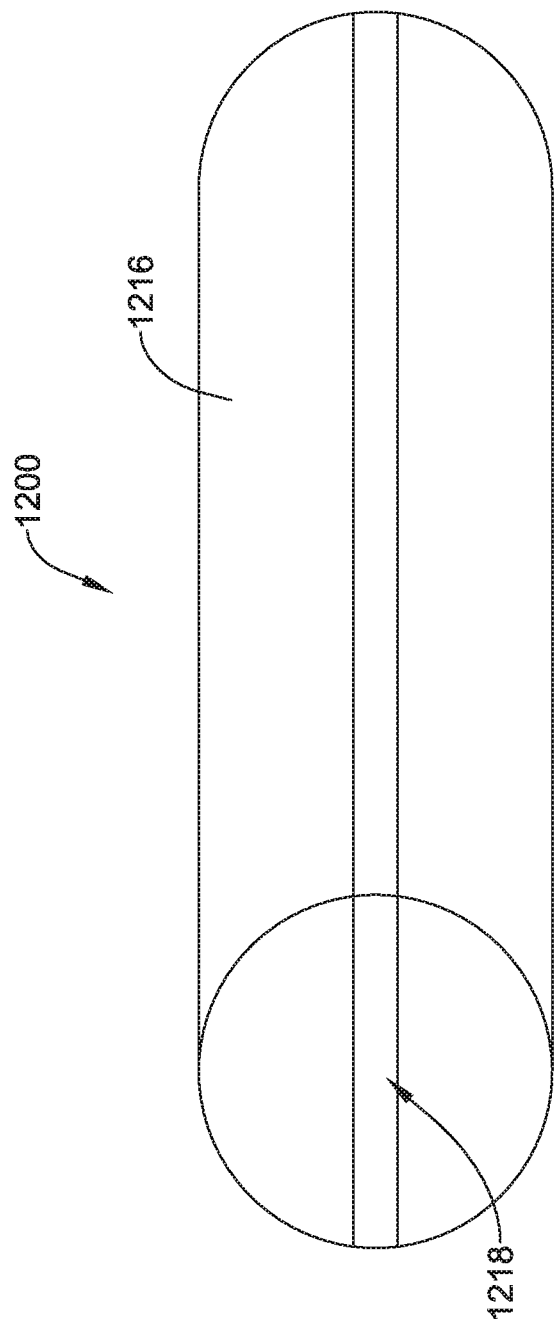
FIG. 12B is an illustrative but non-limiting example of the portion of the IMD of FIG. 12A in an assembled configuration.

Turning to FIG. 12B, the rechargeable power source 1220 and the electronics 1226 have been placed in between section 1202A and 1202B and coupled together. In some cases, the sections 1202A-1202B may be coupled to one another in any suitable manner, which may include hinges, screws, pins, adhesives and/or any other suitable fastener. Alternatively and/or additionally, the sections 1202A-1202B may be coupled to the rechargeable power source 1220 and/or the electronics 1226 in any suitable manner. Accordingly, the sections 1202A-1202B collectively form an elongated body 1216 that is in the example shown substantially cylindrical shaped and the straight or flat surface portions 1206A-1206B may define an internal cavity 1218, configured to receive the rechargeable power source 1220 and the electronics 1226.

Figure 12C:
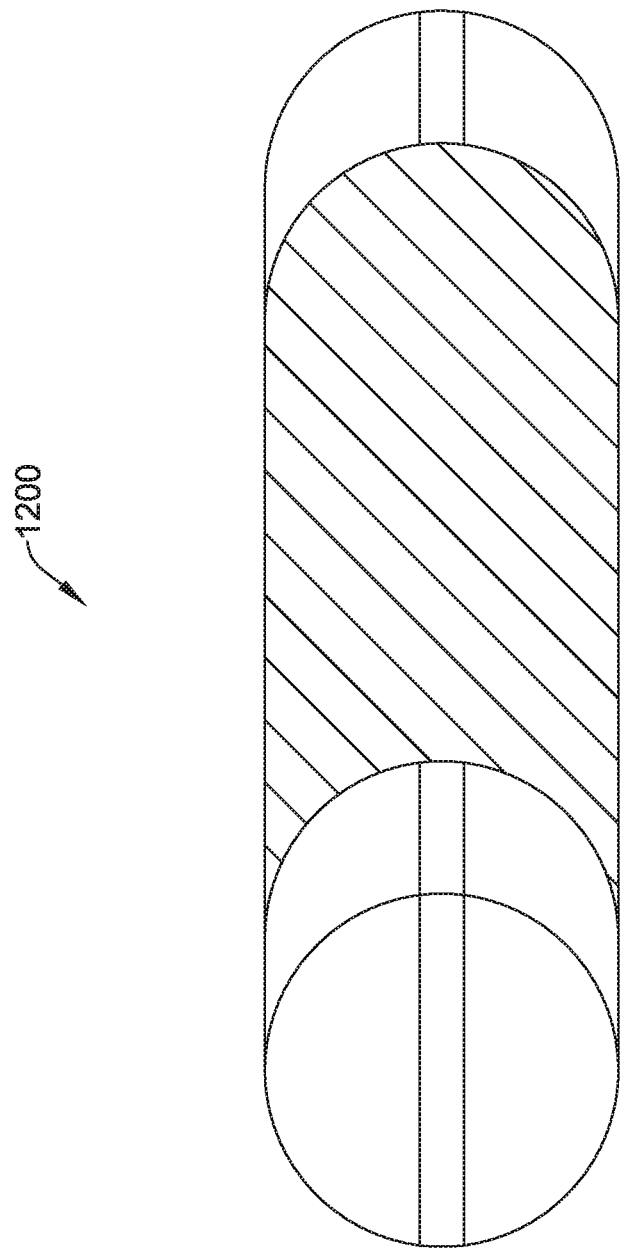
FIG. 12C is an illustrative but non-limiting example of the portion of the IMD of FIG. 12B with a conductive layer added.
Figure 12D:
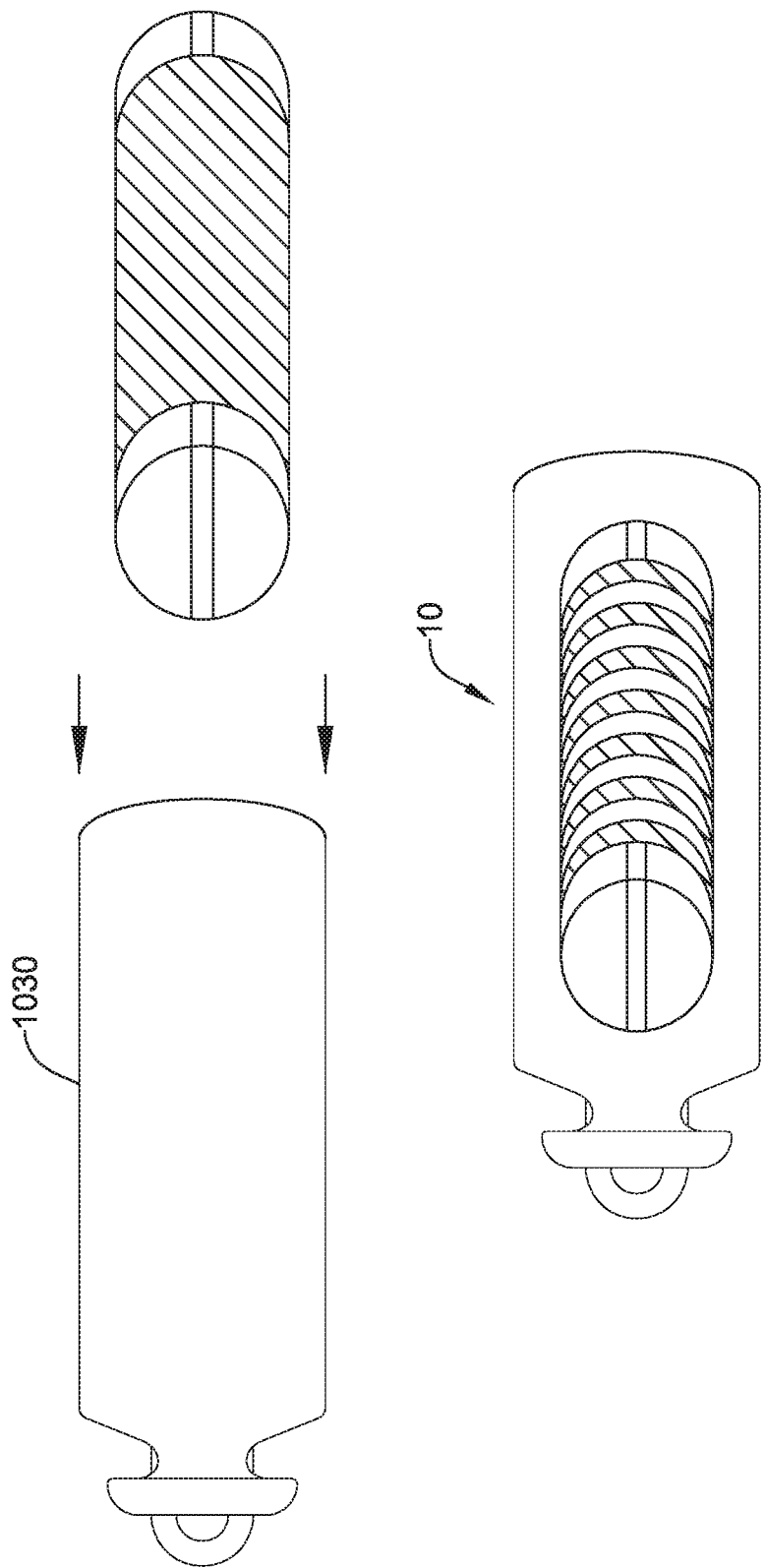
FIG. 12D is an illustrative but non-limiting example of the portion of the IMD of FIG. 12C inserted into a non-ferromagnetic housing.
Figure 12E:
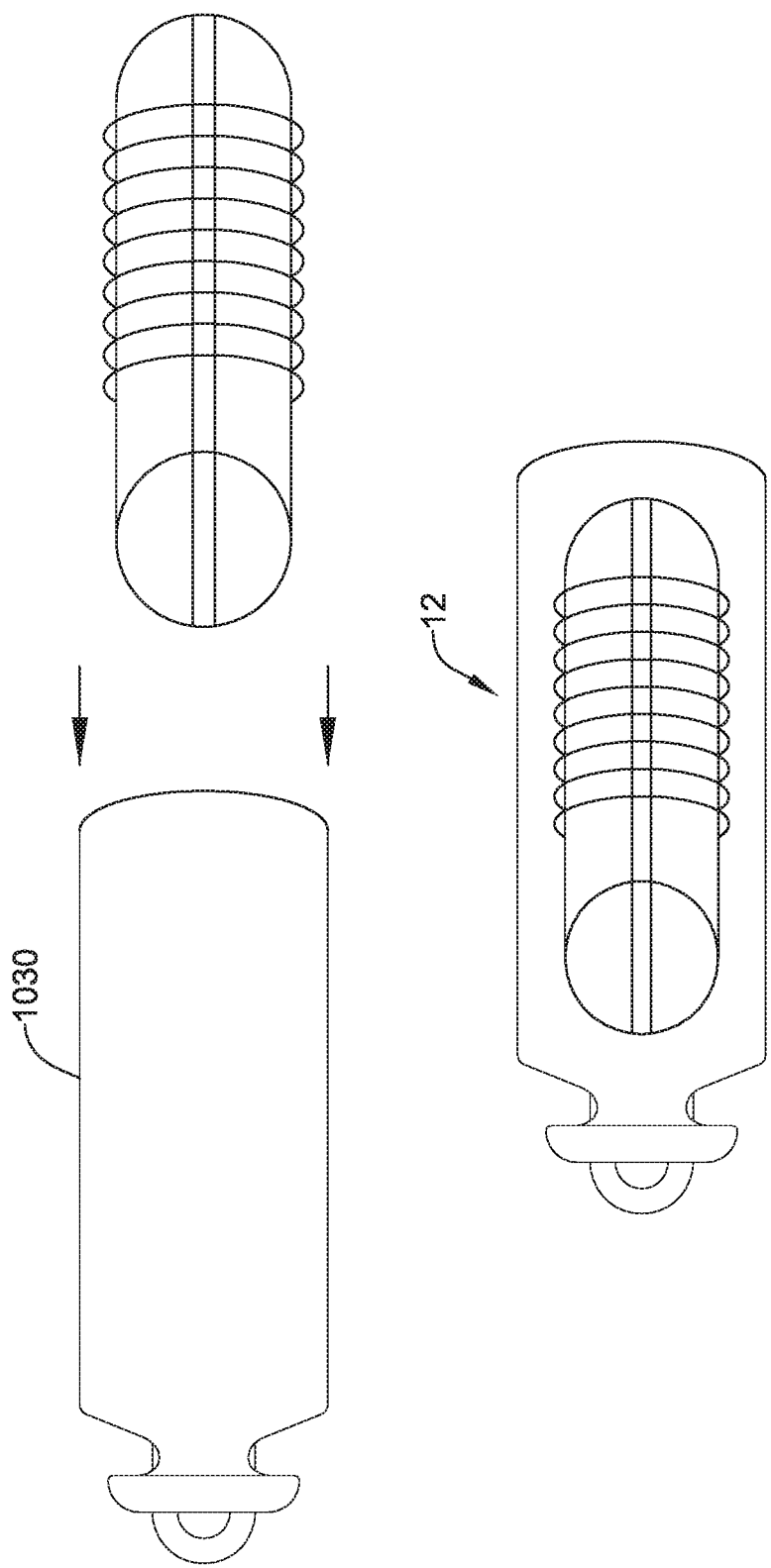
FIG. 12E is an illustrative but non-limiting example of the portion of the IMD of FIG. 12C with a receiving coil added and inserted into a non-ferromagnetic housing.
Figure 12F:
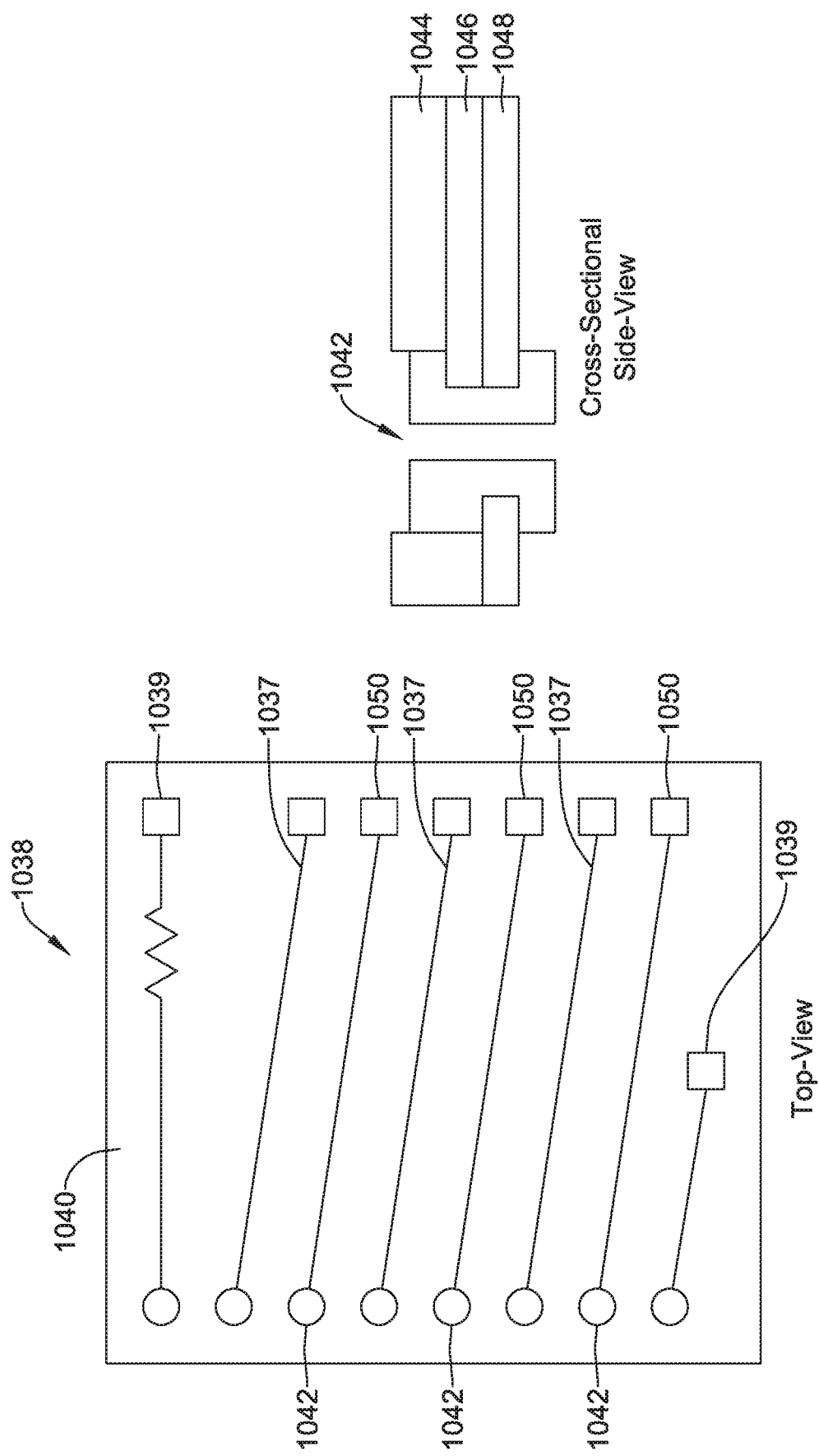
FIG. 12F is an illustrative but non-limiting example of a receiving coil formed on a flexible printed circuit board.
Figure 12G:
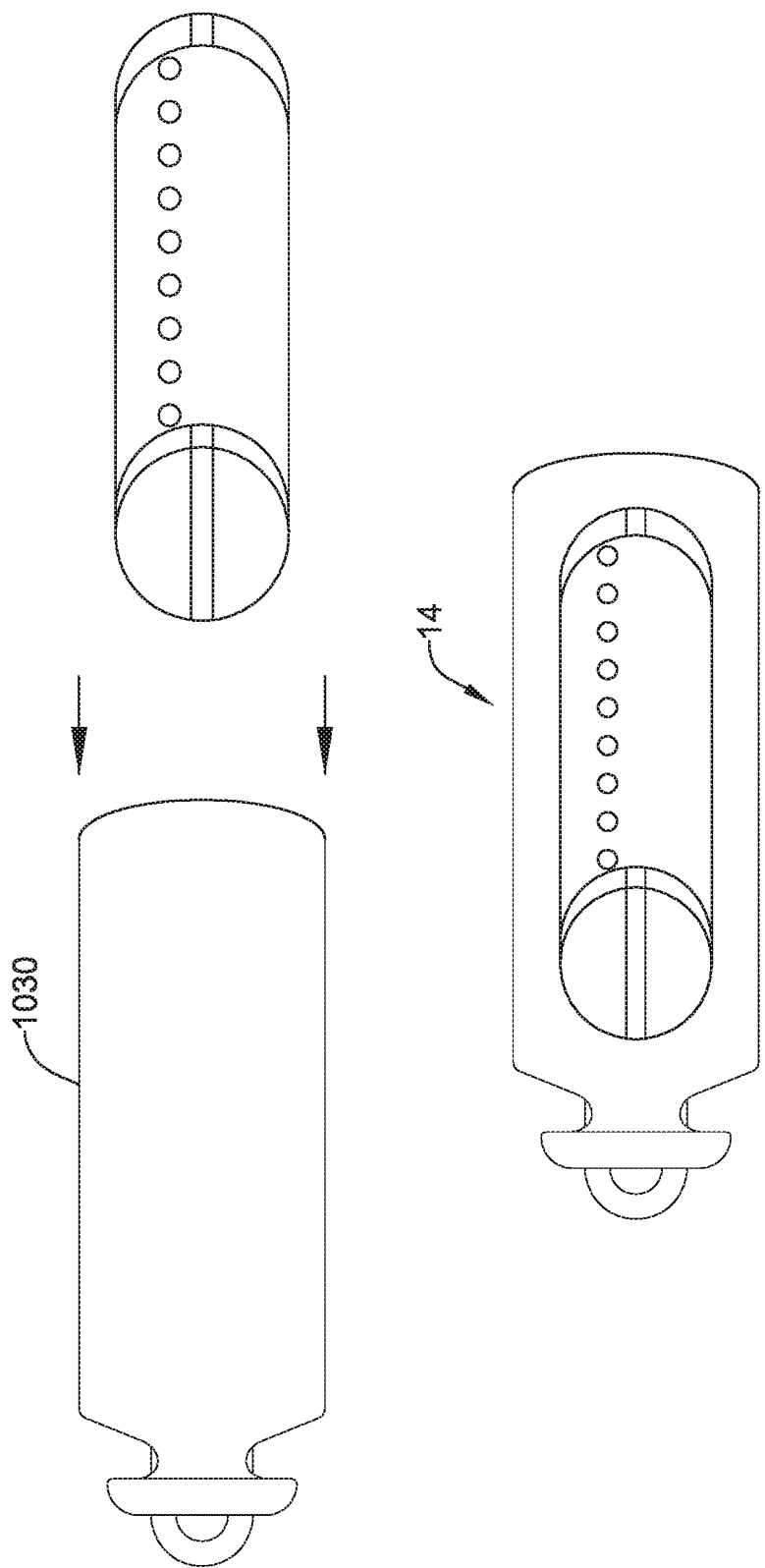
FIG. 12G is an illustrative but non-limiting example of the portion of the IMD of FIG. 12C with the receiving coil of FIG. 12F wrapped around and inserted into a non-ferromagnetic housing.
Figure 12H:
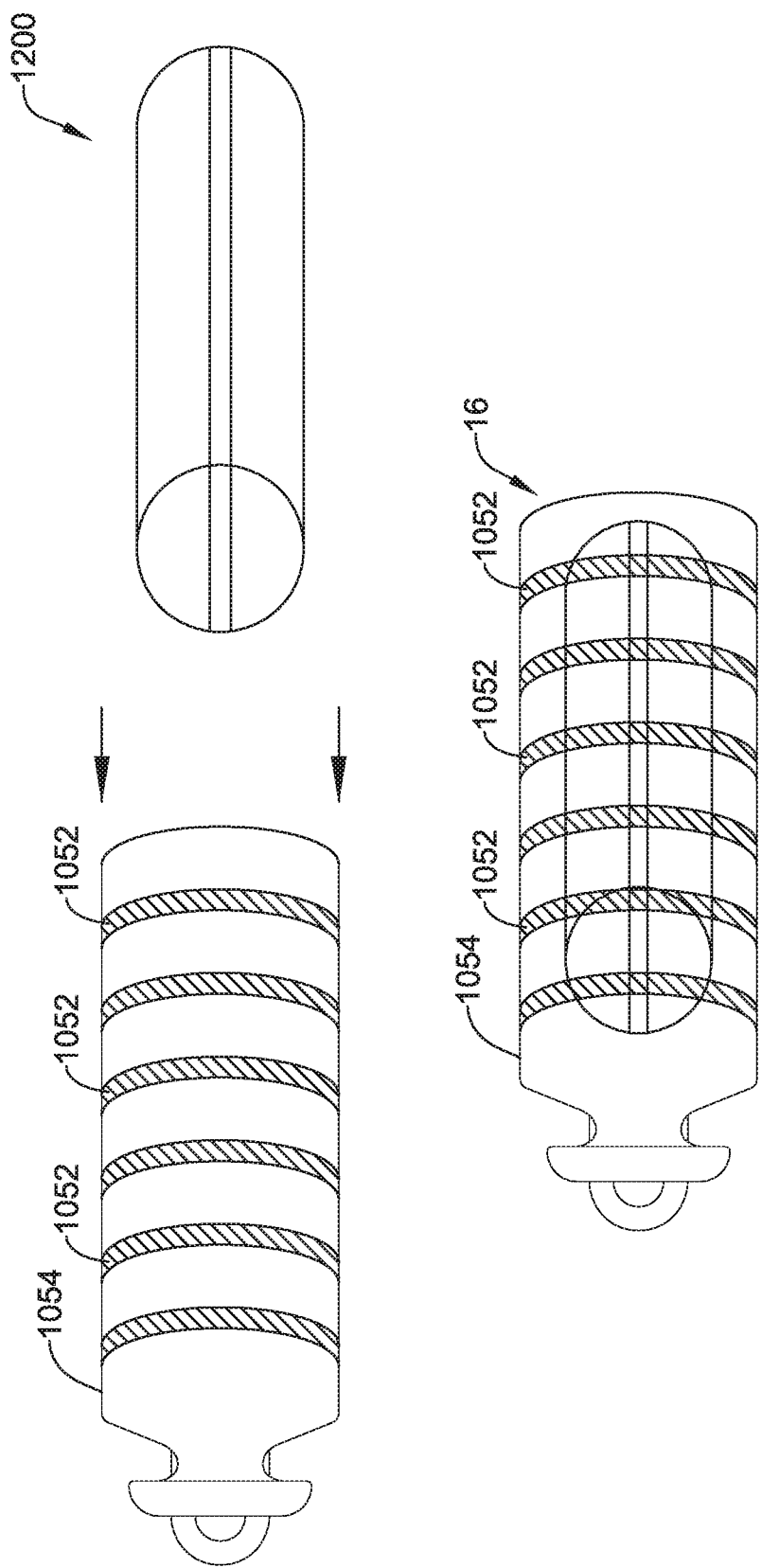
FIG. 12H is an illustrative but non-limiting example of the portion of the IMD of FIG. 12C inserted into a non-ferromagnetic housing with a receiving coil secured to, embedded in, or otherwise carried by the housing.

FIGS. 12C-12H depict the flux concentrator 1200 being configured with exemplary receiving coils and placed in housings. FIGS. 12C-12D depict the conductive layer 1028 being disposed on a portion of the elongated body 1216. The flux concentrator 1200 may then be disposed in the housing 1030 and the receiving coil 1032 may be etched from the conductive layer 1028 through the housing, similar to that described above with respect to FIGS. 10D-10E. FIG. 12E depicts the receiving coil 1034 wound, printed, sprayed, or disposed on a portion of the elongated body 1216, and placed in the housing 1030, similar to that described above with respect to FIG. 10F. FIGS. 12F-12G depict the receiving coil 1036 being disposed on the PCB substrate 1040 to create the PCB coil structure 1038. The PCB coil structure 1038 may then be disposed on a portion of the elongated body 1216, and then placed in the housing 1030, similar to that described above with respect to FIGS. 10G-10H. FIG. 12H depicts the receiving coil 1052 being secured to, embedded in, or otherwise carried by the housing 1054, similar to that described above with respect to FIG. 10I.

Figure 12I:
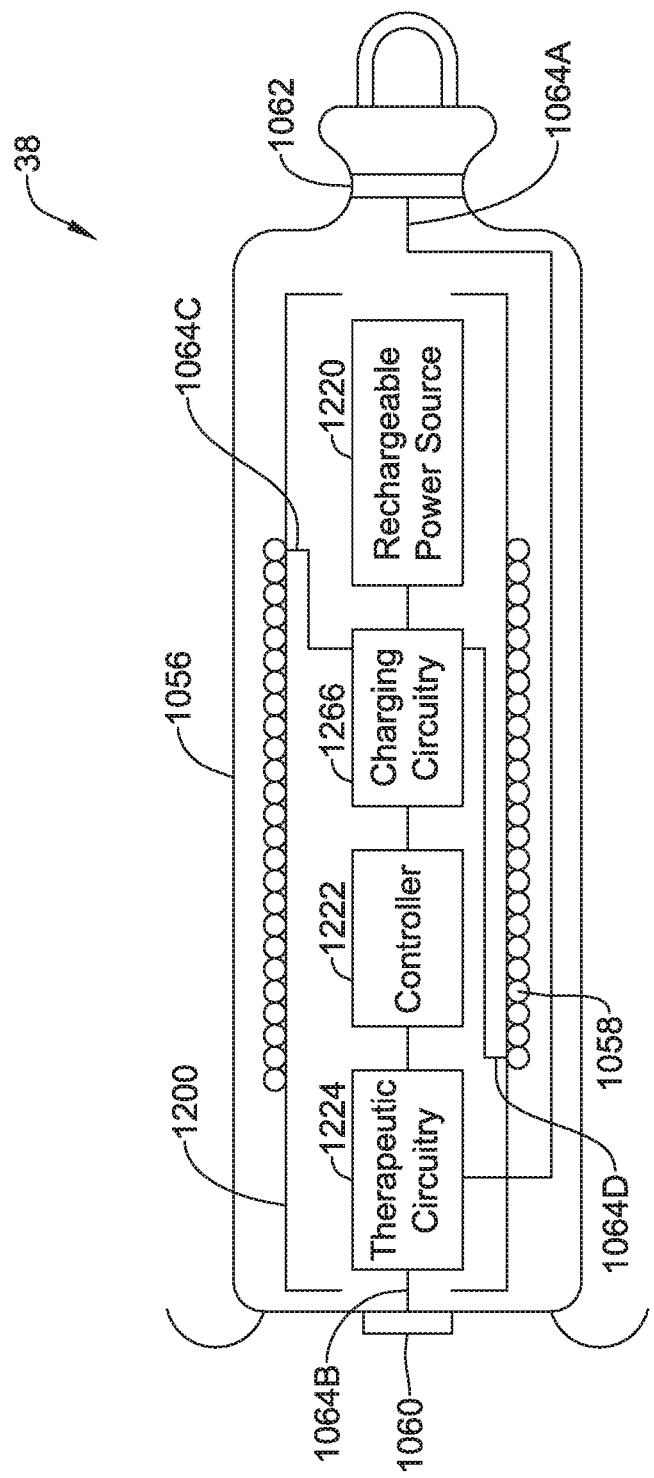
FIG. 12I is a schematic partial cross-sectional view of an illustrative IMD configured with the flux concentrator assembly of FIG. 12E.

FIG. 12I provides a schematic view of an illustrative IMD 38 configured with the two sections 1202A-1202B of the flux concentrator 1200. The configuration and operation of the IMD 38 and its components may be similar to the configuration and operation of the IMD 900 and its components described with respect to FIG. 9, the configuration and operation of the IMD 18 and its components described with respect to FIG. 10J, and the configuration and operation of the IMD 28 and its components described with respect to FIG. 11J. According to various embodiments, the IMD 38 may be configured to be implanted within a patient such as the patient 600 (FIG. 6). The IMD 38 may be manufactured or assembled using any of the process described in regard to FIGS. 12A-12H. For example, the IMD 38 may be assembled using the process described in FIGS. 12A-12D. When so provided, IMD 38 may include the housing 1056 similar to the housing 1030 and the receiving coil 1058 similar to the receiving coil 1032. In another example, the IMD 38 may be assembled using the process described in FIGS. 12A-12B and FIG. 12E. When so provided, IMD 38 may include the housing 1056 similar to the housing 1030 and the receiving coil 1058 similar to the receiving coil 1034. In another example, the IMD 38 may be assembled using the process described in FIGS. 12A-12B and FIGS. 12F-12G. When so provided, the IMD 38 may include the housing 1056 similar to the housing 1030 and the receiving coil 1058 similar to the receiving coil 1036 on the PCB coil structure 1038. In another example, the IMD 38 may be assembled using the process described in FIGS. 12A-12B and FIG. 12H. When so provided, IMD 38 may include the housing 1056 similar to the housing 1054 with the integrated receiving coil 1058 similar to the integrated receiving coil 1052.

The described elements and IMD's from FIG. 9, FIGS. 10A-10J, FIGS. 11A-11J, and FIGS. 12A-12I are by no means exhaustive. In some cases, the elements (e.g., the flux concentrators and the receiving coils) and the IMD's may include other configurations. Moreover, these examples have been used to illustrate how the elements and the IMD's may be customized to potentially optimize the IMD's performance and/or meet the requirements of the physician and the patient. As such, the final design may be configured based on a multiple of factors including reliability, patient comfort, implantation locations and circumstances, etc.

Figure 13:
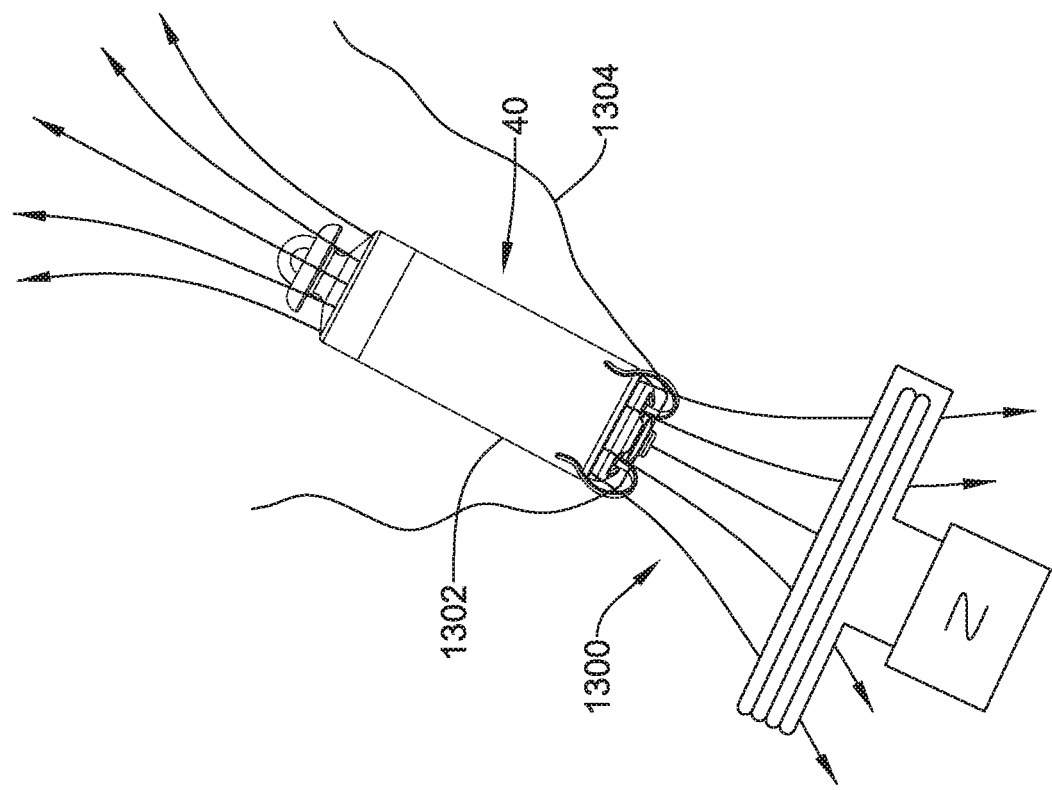
FIG. 13 is a schematic view of an illustrative IMD implanted within a patient and a transmitter coil transmitting energy to the receiving coil of the IMD.

FIG. 13 depicts an example of a flux concentrator (e.g., flux concentrator 916, 1000, 1100, and/or 1200) concentrating, confining, guiding, steering, and/or focusing a magnetic field 1300 through an inductive receiving coil inside housing 1302 of an IMD 40. In some cases, the IMD 40 may be implanted in a heart 1304 of a patient. According to various embodiments, the IMD 40 may be configured and may operate similar to IMD 900, 10, 12, 14, 16, 18, 20, 22, 24, 26, 28, 30, 32, 34, 36, and/or 38. In some cases, the high permeability of the flux concentrator inside the housing 1302 relative to the surrounding environment, may cause the magnetic field 1300 to bend and be concentrated in the flux concentrator, which passes through the receiving coil inside the housing 1302. The receiving coil may then receive the energy from the magnetic field 1300 at a wavelength and intensity that is safe for a patient and that the IMD 40 may use to recharge a rechargeable power source within the IMD 40. It is contemplated that the magnetic energy may be received at a rate that exceeds a rate at which power is being drawn from the rechargeable battery and consumed by various components within the IMD 40.

In some cases, the flux concentrator may have a relative permeability (pr) greater than 10, 100, 1000, 10000, or more. The flux concentrator may include a variety of different materials. For instances, in some cases, the flux concentrator may be a ferrite, an alloy (e.g., mu-metal), a metallic oxide, a metallic sulfide, a metallic oxyhydroxide, or a metal. These are just examples. In some cases, the flux concentrator may have a conductance ($\sigma$) of less than 1E-4 ohm$^{-1}$ cm$^{-1}$. In some cases, the flux concentrator may have a cylindrical or a substantially cylindrical shape, or a tubular or substantially tubular shape or form. In some cases, the housing 1302 itself may be composed of the flux concentrator. In some cases, the flux concentrator may have a substrate or base, such as a polymer substrate or base, with a magnetically permeable material attached, embedded, disposed on, or otherwise carried by the substrate or base. When so provided, a magnetic field may be applied to the flux concentrator before, during and/or after the polymer substrate is curing so as to pole the magnetically permeable material of the flux concentrator in a common direction. Alternatively, or in addition, the housing 1302 itself, or a portion thereof may be formed from the flux concentrator.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device (IMD) configured to be implanted within a patient, the IMD comprising:
    a housing configured for trans-catheter deployment;
    a plurality of electrodes exposed external to the housing;
    therapeutic circuitry configured to sense one or more signals via one or more of the plurality of electrodes and/or to stimulate tissue via one or more of the plurality of electrodes;
    a plurality of flux concentrator elements positioned within the housing, each flux concentrator element includes an inner major surface, an outer major surface, and two opposing ends, wherein the plurality of elongated flux concentrator elements are arranged in an end-to-end configuration to collectively form an elongated body that defines an internal cavity;

wherein each of the plurality of flux concentrator elements comprises a magnetically permeable material with a relative permeability ($\mu_r$) of greater than 10;

a receiving coil disposed around at least a portion of the elongated body, wherein the elongated body operates as a flux concentrator for concentrating an externally generated magnetic flux through the receiving coil to induce a current in the receiving coil;

a rechargeable power source configured to power the therapeutic circuitry, at least part of the rechargeable power source disposed within the internal cavity defined by the elongated body; and charging circuitry operatively coupled with the receiving coil and the rechargeable power source, the charging circuitry configured to use the current induced in the receiving coil to charge the rechargeable power source.

2. The IMD of claim 1, wherein at least part of the therapeutic circuitry is disposed within the internal cavity defined by the elongated body.

3. The IMD of claim 1, wherein the plurality of flux concentrator elements are arranged in an end-to-end configuration with an air or a non-magnetically permeable material between adjacent ends.

4. The IMD of claim 1, wherein a first one of the two opposing ends of a first one of the plurality of flux concentrator elements is arranged in an end-to-end configuration with a first one of the two opposing ends of a second one of the plurality of flux concentrator elements, wherein the first one of the two opposing ends of the first one of the plurality of flux concentrator elements is keyed to the first one of the two opposing ends of the second one of the plurality of flux concentrator elements.

5. The IMD of claim 4, wherein the first one of the two opposing ends of the first one of the plurality of flux concentrator elements overlaps with at least part of the first one of the two opposing ends of the second one of the plurality of flux concentrator elements.

6. The IMD of claim 1, wherein the plurality of flux concentrator elements each have a ring shape and are stacked in an end-to-end configuration to collectively form the elongated body.

7. The IMD of claim 1, wherein each of the plurality of flux concentrator elements is arc shaped and forms part of a circumference of the internal cavity.

8. The IMD of claim 1, wherein the receiving coil is disposed on a flexible printed circuit board (PCB) that is wrapped about the elongated body.

9. The IMD of claim 1, wherein the receiving coil is integrated with the housing.

10. An implantable medical device (IMD) configured to be implanted within a patient, the IMD comprising:

a housing configured for trans-catheter deployment;

operational circuitry disposed within the housing, the operational circuitry configured to control at least part of the IMD;

an elongated tubular shaped flux concentrator disposed within the housing, the elongated tubular shaped flux concentrator defining an internal cavity that extends from a first open end to a second opposing open end, the elongated tubular shaped flux concentrator comprising two or more interlocking segments that each include a magnetically permeable material with a relative permeability ($\mu_r$) of greater than 10;

a receiving coil disposed around at least a portion of the elongated tubular shaped flux concentrator body, wherein the elongated tubular shaped flux concentrator operates as a flux concentrator for concentrating an externally generated magnetic flux through the receiving coil to induce a current in the receiving coil;

a rechargeable power source within the housing configured to power the operational circuitry, wherein at least part of the rechargeable power source is disposed within the internal cavity defined by the elongated tubular shaped flux concentrator; and charging circuitry within the housing operatively coupled with the receiving coil and the rechargeable power source, the charging circuitry configured to use the current induced in the receiving coil to charge the rechargeable power source.

11. The IMD of claim 10, wherein the elongated tubular shaped flux concentrator is cylindrical shaped.

12. The IMD of claim 10, wherein at least one of the two or more interlocking segments includes a side with a ridge that is configured to overlap with a corresponding ridge on a side of an adjacent interlocking segment.

13. The IMD of claim 10, wherein the two or more interlocking segments are configured to form an interlock that prevents relative movement between at least two of the two or more interlocking segments in at least one dimension.

14. The IMD of claim 10, wherein the two or more interlocking segments are configured to form an interlock that prevents relative movement between at least two of the two or more interlocking segments in at least two dimensions.

15. The IMD of claim 10, wherein the receiving coil is disposed on a flexible printed circuit board (PCB) that is wrapped about the elongated tubular shaped flux concentrator.

16. The IMD of claim 10, wherein the receiving coil is tunable to achieve a desired resonance frequency.

17. An implantable medical device (IMD) configured to be implanted within a patient, the IMD comprising:

a housing configured for trans-catheter deployment;

operational circuitry disposed within the housing, the operational circuitry configured to control at least part of the IMD;

an elongated hollow flux concentrator disposed within the housing, the elongated hollow flux concentrator defines an internal cavity that extends from a first open end to a second opposing open end, the elongated hollow flux concentrator comprising two or more segments that touch at least one other of the two or more segments, wherein each of the two or more segments include a magnetically permeable material with a relative permeability ($\mu_r$) of greater than 10;

a receiving coil disposed around at least a portion of the elongated hollow flux concentrator, wherein the elongated hollow flux concentrator operates as a flux concentrator for concentrating an externally generated magnetic flux through the receiving coil to induce a current in the receiving coil;

a rechargeable power source within the housing configured to power the operational circuitry, wherein at least part of the rechargeable power source is disposed within the internal cavity defined by the elongated hollow flux concentrator; and charging circuitry within the housing operatively coupled with the receiving coil and the rechargeable power source, the charging circuitry configured to use the current induced in the receiving coil to charge the rechargeable power source.

18. The IMD of claim 17, wherein each of the two or more segments are keyed to at least one other of the two or more segments.

19. The IMD of claim 17, wherein the receiving coil is disposed on a flexible printed circuit board (PCB) that is wrapped about the elongated hollow flux concentrator.

\* \* \* \* \*